(12) United States Patent
Nam et al.

(10) Patent No.: US 9,147,849 B2
(45) Date of Patent: Sep. 29, 2015

(54) ELECTRON TRANSPORT MATERIAL AND ORGANIC ELECTROLUMINESCENT DEVICE USING THE SAME

(71) Applicant: Alpha Chem Co., Ltd., Suwon-si (KR)

(72) Inventors: Hyun-Goog Nam, Suwon-si (KR); Dae Won Lim, Incheon (KR); Je-yong Kim, Gwangmyeong-si (KR); Sang-mi Park, Siheung-si (KR); Seung-hee Jang, Suwon-si (KR); Sang Youn Lee, Hwaseong-si (KR); Juseok Ham, Seoul (KR); Kyu-oh Cho, Yongin-si (KR); Hyun-don Kim, Anyang-si (KR)

(73) Assignee: Alpha Chem Co., Ltd., Gyeonggi-do (KR)

( * ) Notice: Subject to any disclaimer, the term of this patent is extended or adjusted under 35 U.S.C. 154(b) by 0 days.

(21) Appl. No.: 13/772,439

(22) Filed: Feb. 21, 2013

(65) Prior Publication Data

US 2014/0054561 A1  Feb. 27, 2014

(30) Foreign Application Priority Data

May 10, 2012 (KR) .......... 10-2012-0057154
Oct. 30, 2012 (KR) .......... 10-2012-0120910

(51) Int. Cl.
| | | |
|---|---|---|
| C07D 239/70 | (2006.01) | |
| H01L 51/00 | (2006.01) | |
| C07D 403/12 | (2006.01) | |
| C07D 401/14 | (2006.01) | |
| C07D 413/14 | (2006.01) | |
| C07D 401/04 | (2006.01) | |
| C07D 401/12 | (2006.01) | |
| C07D 409/10 | (2006.01) | |
| C07D 409/14 | (2006.01) | |
| C07D 498/04 | (2006.01) | |
| C07D 513/04 | (2006.01) | |
| H01L 51/50 | (2006.01) | |

(52) U.S. Cl.
CPC .......... H01L 51/0072 (2013.01); C07D 239/70 (2013.01); C07D 401/04 (2013.01); C07D 401/12 (2013.01); C07D 401/14 (2013.01); C07D 403/12 (2013.01); C07D 409/10 (2013.01); C07D 409/14 (2013.01); C07D 413/14 (2013.01); C07D 498/04 (2013.01); C07D 513/04 (2013.01); H01L 51/0058 (2013.01); H01L 51/0067 (2013.01); H01L 51/0068 (2013.01); H01L 51/0074 (2013.01); H01L 51/0052 (2013.01); H01L 51/0054 (2013.01); H01L 51/0071 (2013.01); H01L 51/5072 (2013.01)

(58) Field of Classification Search
CPC ............ H01L 51/0072; H01L 51/0067; H01L 51/072
USPC .............................. 544/249; 257/40
See application file for complete search history.

(56) References Cited

U.S. PATENT DOCUMENTS

| | | |
|---|---|---|
| 5,645,948 A | 7/1997 | Shi et al. |
| 8,012,602 B2 | 9/2011 | Schafer et al. |

FOREIGN PATENT DOCUMENTS

| | | | |
|---|---|---|---|
| JP | 2010215759 | * | 9/2010 |
| JP | 2011084531 | * | 4/2011 |
| KR | 1020120117693 A | | 10/2012 |
| WO | 2004039786 A1 | | 5/2004 |
| WO | WO 2011024976 | * | 3/2011 |

* cited by examiner

Primary Examiner — Paul V Ward
(74) Attorney, Agent, or Firm — The Webb Law Firm

(57) ABSTRACT

Provided are a new electron transport material and an organic electroluminescent device including the same. The electron transport material according to the present invention may have the excellent luminescence property and reduce the driving voltage to increase the power efficiency, such that the organic electroluminescent device using less consumption power may be manufactured.

7 Claims, 2 Drawing Sheets

ELECTRON TRANSPORT MATERIAL AND ORGANIC ELECTROLUMINESCENT DEVICE USING THE SAME

CROSS-REFERENCE TO RELATED APPLICATIONS

This application claims priority under 35 U.S.C. §119 to Korean Patent Application No. 10-2012-0057154, filed on May 10, 2012 and No. 10-2012-0120910 filed on Oct. 30, 2012 in the Korean Intellectual Property Office, the disclosure of which is incorporated herein by reference in its entirety.

TECHNICAL FIELD

The following disclosure relates to a new electron transport material and an organic electroluminescent device using the same.

BACKGROUND

An organic electroluminescent device is a device emitting light while electrons and holes disappear after being coupled in pairs when an electron charge is injected into an organic film formed between an electron injection electrode (cathode) and a hole injection electrode (anode). The organic electroluminescent device has advantages in that the device may be formed on a flexible transparent substrate made of, for example, plastic material, driven at a low voltage (10V or less) as compared with a plasma display panel or an inorganic electroluminescent (EL) display, has relatively low power consumption and excellent color sensation.

Generally, the organic electroluminescent device has a structure consisting of a substrate, an anode, a hole injection layer receiving a hole from the anode, a hole transport layer transporting the hole, a luminescent layer emitting light while the hole and an electron are bonded, an electron transport layer receiving the electrode from a cathode to transport the electron to the luminescent layer, and the cathode. In some cases, the luminescent layer may be configured by applying a small amount of a fluorescent or phosphorescent dye to the electron transport layer or the hole transport layer without a separate luminescent layer. In the case of using a polymer, generally, one polymer may entirely serve as the hole transport layer, the luminescent layer, and the electron transport layer. Organic thin film layers between two electrodes may be formed by a method such as a vacuum deposition method, a spin coating method, an inkjet printing method, a roll coating method, or the like, and for effective injection of the electron from the cathode, a separate electron injection layer may be inserted.

In the case in which an interface between the electrode and an organic material is stabilized, or in the case of the organic material, since there is a large difference in a movement rate between the hole and the electron, an appropriate hole transport layer and electron transport layer are used, the hole and the electron may be effectively transported to the luminescent layer. In addition, in order to balance the hole and the electron densities in the luminescent layer to increase luminescence efficiency, the organic electroluminescent device is manufactured to have a multi-layer thin film structure.

Meanwhile, as a representative example of the existing electron transport material, there are aluminum complex and beryllium complex such as Alq3 (tris(8-hydroxyquinoline) aluminum(III)) and Bebq (bis(10-hydroxybenzo-[h]quinolinato)beryllium). However, in the case in which these materials are used in a blue electroluminescent device, color purity may be decreased due to luminescence caused by exciton diffusion.

In addition, TPBI, which was reported by Kodak in 1996 disclosed in U.S. Pat. No. 5,645,948, (See the following structure), is known to be a representative material for electron transport layer having an imidazole group. This material contains three N-phenyl benzimidazole groups at 1, 3, and 5 substitution positions of benzene, and has a function of blocking holes from a luminescent layer as well as transporting electrons. However, stability of TPBI is too low to be actually used in the device.

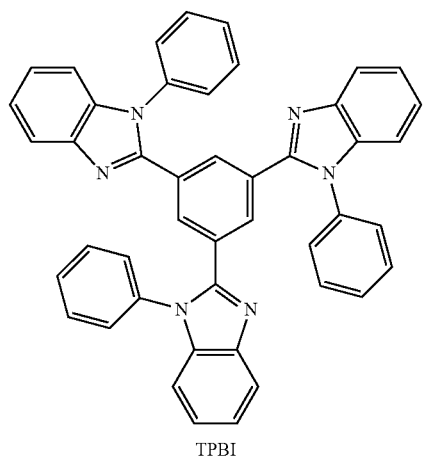

TPBI

In the case of the electron transport material according to the related art, unlike the reported contents, actually, the material may slightly improve only a driving voltage, or there are problems such as significant deterioration of a device driving lifespan or negative properties such as variation in the device lifespan according to the color, and deterioration of thermal stability, or the like.

In addition, a fluorescent material was used in the organic electroluminescent device according to the related art, but gradually, phosphorescent material has been mainly used in the organic electroluminescent device. Therefore, in the electron transport material, which is a common material of the organic electroluminescent device, electron mobility appropriate for the phosphorescent material, low driving voltage, and a hole blocking property have been required.

RELATED ART DOCUMENT

Patent Document (Patent Document 1) U.S. Pat. No. 5,645,948

SUMMARY

An embodiment of the present invention is directed to providing a new electron transport material capable of significantly improving luminescence efficiency, stability and a lifespan of a device.

In addition, an embodiment of the present invention is directed to providing an organic electroluminescent device capable of having an excellent luminescence property by using the new electron transport material and decreasing consumption power by decreasing driving voltage to induce increase in power efficiency.

In one general aspect, there are provided an electron transport material represented by the following Chemical Formula 1, and an organic electroluminescent device containing the same. The electron transport material according to the present invention is used, such that excellent luminescence property may be obtained, and an increase in power efficiency is induced by decreasing driving voltage, such that the organic electroluminescent device using less consumption power may be manufactured.

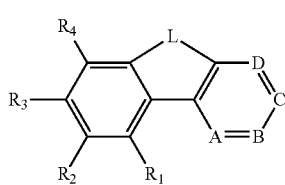

[Chemical Formula 1]

[In Chemical Formula 1,

A, B, C, and D each are independently C-($L_1$)$_m$-$Ar_1$ or N, but two of A, B, C, and D are N, the other two are C-($L_1$)$_m$-$Ar_1$, and each of -($L_1$)$_m$-$Ar_1$ may be the same as or different from each other, but two -($L_1$)$_m$-$Ar_1$ are not hydrogen at the same time;

L is (C1-C20)alkylene or (C2-C20)alkenylene, a carbon atom (—CH2-) of alkylene of L may be substituted with a heteroatom selected from NR(R is (C1-C30)alkyl), O, and S, and a carbon atom (=CH—) of alkenylene of L may be substituted with N;

$R_1$ to $R_4$ each are independently hydrogen, (C1-C30)alkyl, (C3-C30)cycloalkyl, (C6-C30)aryl, or (C3-C30)heteroaryl;

$L_1$(s) each are independently a single bond, (C6-C30) arylene, or (C3-C30)heteroarylene;

m is an integer of 1 to 3, and in the case in which m is an integer of 2 or more, $L_1$(s) each are the same as or different from each other;

$Ar_1$(s) each are independently hydrogen, (C1-C30)alkyl, (C6-C30)aryl, or (C3-C30)heteroaryl;

alkyl, cycloalkyl, aryl, heteroaryl of $R_1$ to $R_4$, alkylene or alkenylene of L, arylene and heteroarylene of $L_1$, and aryl and heteroaryl of $Ar_1$ may be substituted with at least one selected from a group consisting of (C1-C30)alkyl, halo(C1-C30) alkyl, halogen, cyano, (C3-C30)cycloalkyl, (C1-C30)alkoxy, (C6-C30)aryloxy, (C6-C30)aryl, (C6-C30)ar(C1-C30)alkyl, (C1-C30)alkyl(C6-C30)aryl, (C3-C30)heteroaryl, (C3-C30) heteroaryl substituted with (C1-C30)alkyl, (C3-C30)heteroaryl substituted with (C6-C30)aryl, mono or di(C1-C30) alkylamino, mono or di(C6-C30)arylamino, tri(C1-C30) alkylsilyl, di(C1-C30)alkyl(C6-C30)arylsilyl, tri(C6-C30) arylsilyl, nitro, and hydroxy; and Heteroarylene and heteroaryl contains at least one hetero atom selected from B, N, O, S, P(=O), Si and P.

The terms "alkyl", "alkoxy" and other substituents including an "alkyl" part described in the present invention include both of the straight chain type and the branched chain type, and the term "cycloalkyl" includes polycyclic hydrocarbon such as substituted or unsubstituted adamantyl or substituted or unsubstituted (C7-C30)bicycloalkyl as well as monocyclic ring system. The term "aryl" described herein, which is an organic radical derived from aromatic hydrocarbon by the removal of one hydrogen atom, may include a single ring or a fused ring containing, preferably 4 to 7 ring atoms, and more preferably 5 or 6 ring atoms, and include rings in which two or more aryl groups are combined through a single bond(s). Specific examples of aryl include phenyl, naphthyl, biphenyl, terphenyl, anthryl, indenyl, fluorenyl, phenanthryl, triphenylenyl, pyrenyl, perylenyl, chrysenyl, naphtacenyl, fluoranthenyl, and the like. The term "heteroaryl" described herein means an aryl group containing 1 to 4 hetero atom(s) selected from B, N, O, S, P(=O), Si, and P for the aromatic cyclic backbone atoms, and carbon atom(s) for remaining aromatic cyclic backbone atoms. The heteroaryl may be a 5- or 6-membered monocyclic heteroaryl or a polycyclic heteroaryl which is fused with one or more benzene ring(s), and may be partially saturated. In addition, the "heteroaryl" in the present invention may include the structures having one or more heteroaryl group(s) bonded through a single bond. The heteroaryl groups may include divalent aryl groups of which the heteroatoms are oxidized or quarternized, for example, to form N-oxides, quaternary salts, or the like. Specific examples of the heteroaryl group include monocyclic heteroaryl groups such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, or the like; polycyclic heteroaryl groups such as benzofuranyl, benzothiophenyl, isobenzofuranyl, benzimidazolyl, benzothiazolyl, benzisothiazolyl, benzisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, phenanthridinyl, benzodioxolyl, dibenzofuranyl, dibenzothiophenyl, or the like; and corresponding N-oxides (for example, pyridyl N-oxide, quinolyl N-oxide); quaternary salts thereof, and the like.

Further, '(C1-C30)alkyl' described herein may be preferably (C1-C20)alkyl, more preferably, (C1-C10)alkyl, and '(C6-C30)aryl' described herein may be preferably (C6-C20) aryl. '(C3-C30)heteroaryl' may be preferably (C3-C20)heteroaryl. '(C3-C30)cycloalkyl' may be preferably (C3-C20) cycloalkyl, more preferably (C3-C7)cycloalkyl.

More specifically, the electron transport material according to the present invention may be represented by the following Chemical Formula 2 or 3.

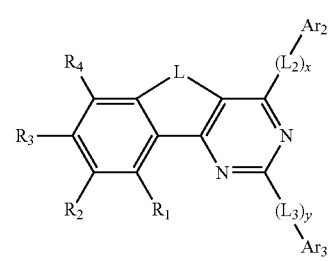

[Chemical Formula 2]

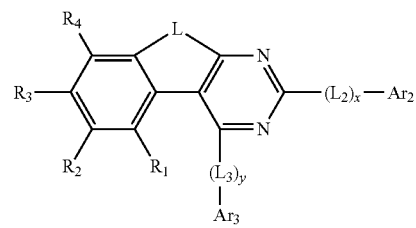

[Chemical Formula 3]

[In Chemical Formulas 2 and 3, $R_1$ to $R_4$ and L each has the same definition in Chemical Formula 1;

$L_2$ and $L_3$ each are independently a single bond, (C6-C30) arylene, or (C3-C30)heteroarylene;

x and y each are independently an integer of 1 to 3, wherein when x is an integer of 2 or more, $L_2$(s) are the same as or different from each other, and when y is an integer of 2 or more, $L_3$(s) are the same as or different from each other;

$Ar_2$ and $Ar_3$ each are independently hydrogen, (C1-C30)alkyl, (C6-C30)aryl, or (C3-C30)heteroaryl;

Arylene and heteroarylene of $L_2$ and $L_3$, and aryl and heteroaryl of $Ar_2$ and $Ar_3$ may be substituted with at least one selected from a group consisting of (C1-C30)alkyl, halo(C1-C30)alkyl, halogen, cyano, (C3-C30)cycloalkyl, (C1-C30)alkoxy, (C6-C30)aryloxy, (C6-C30)aryl, (C6-C30)ar(C1-C30)alkyl, (C1-C30)alkyl(C6-C30)aryl, (C3-C30)heteroaryl, (C3-C30)heteroaryl substituted with (C1-C30)alkyl, (C3-C30)heteroaryl substituted with (C6-C30)aryl, mono or di(C1-C30)alkylamino, mono or di(C6-C30)arylamino, tri(C1-C30)alkylsilyl, di(C1-C30)alkyl(C6-C30)arylsilyl, tri(C6-C30)arylsilyl, nitro, and hydroxy; and $-(L_2)_x-Ar_2$ and $-(L_3)_y-Ar_3$ are not hydrogen at the same time.]

More specifically, the electron transport material according to the present invention may be represented by the following Chemical Formulas 4 to 9.

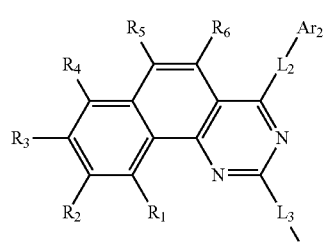

[Chemical Formula 4]

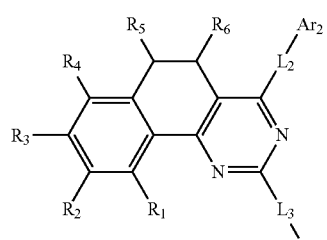

[Chemical Formula 5]

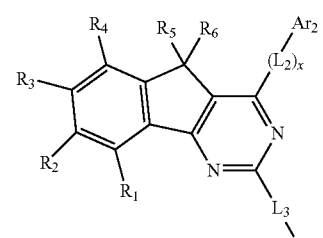

[Chemical Formula 6]

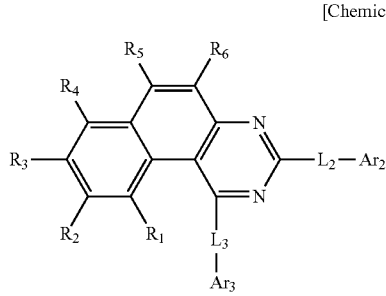

[Chemical Formula 7]

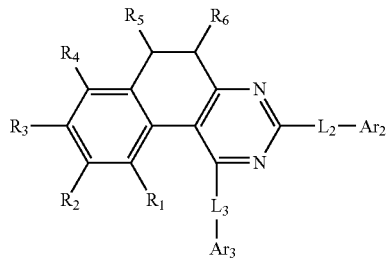

[Chemical Formula 8]

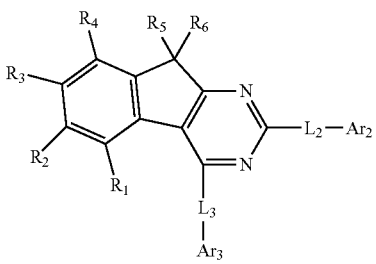

[Chemical Formula 9]

[In Chemical Formulas 4 to 9, $R_1$ to $R_6$ each are independently hydrogen, (C1-C30)alkyl, (C3-C30)cycloalkyl, (C6-C30)aryl, or (C3-C30)heteroaryl;

$L_2$ and $L_3$ each are independently a single bond, (C6-C30)arylene, or (C3-C30)heteroarylene;

x is an integer of 1 to 3, and when x is an integer of 2 or more, $L_1$(s) each are the same as or different from each other, $Ar_2$ and $Ar_3$ each are independently hydrogen, (C1-C30)alkyl, (C6-C30)aryl, or (C3-C30)heteroaryl; and arylene of $L_2$ and $L_3$ and aryl and heteroaryl of $Ar_2$ and $Ar_3$ may be further substituted with at least one selected from a group consisting of (C1-C30)alkyl, (C6-C30)aryl, (C6-C30)ar(C1-C30)alkyl, (C1-C30)alkyl(C6-C30)aryl, and (C3-C30)heteroaryl.]

In the electron transport material of Chemical Formula 1, $L_2$ and $L_3$ each are a single bond, phenylene, biphenylene, 9,9-dimethylfluorenylene, naphthylene, anthrylene, pyridinylene, or pyrimidinylene; $Ar_2$ and $Ar_3$ each are independently hydrogen, (C1-C30)alkyl, or selected from the following structure; and

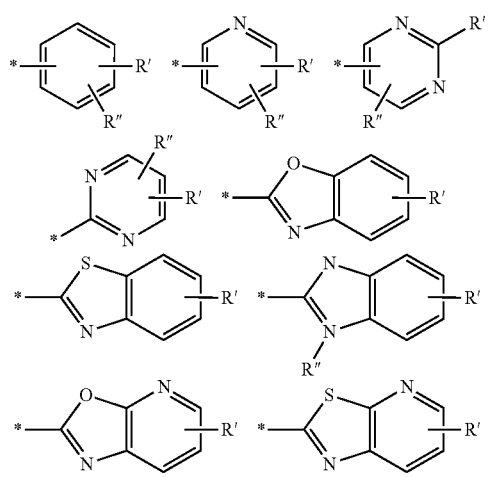

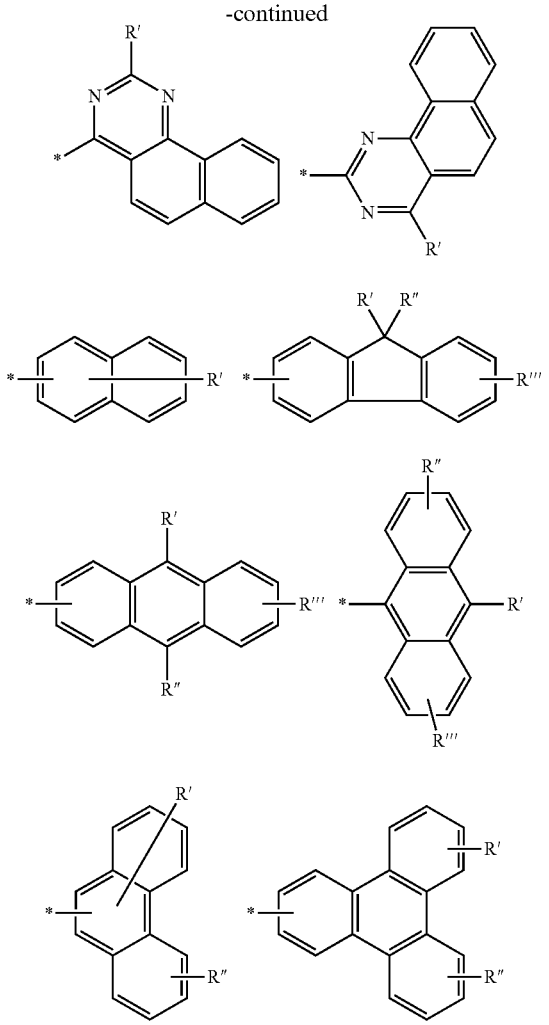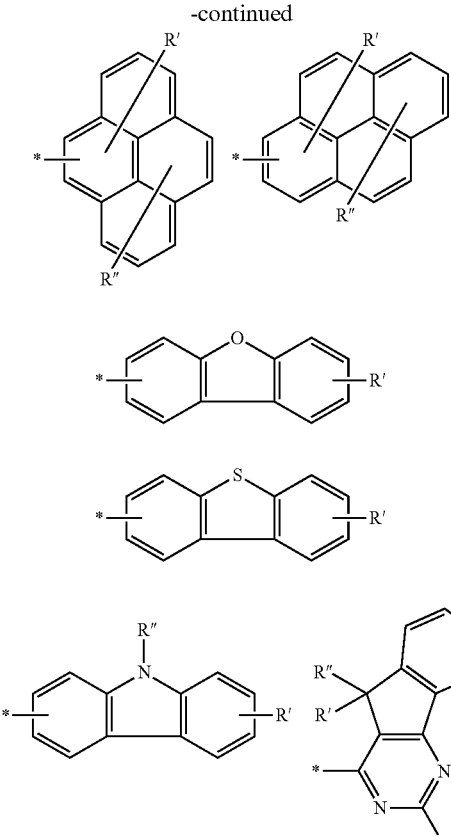
R', R", and R'" each may be independently hydrogen, (C1-C30)alkyl, (C6-C30)aryl, (C3-C30)heteroaryl, or (C1-C30)alkyl(C6-C30)aryl.
The electron transport material may be, for example, the following compounds, but is not limited thereto.
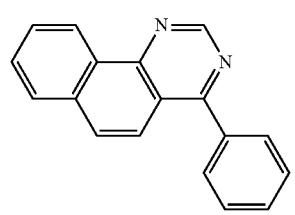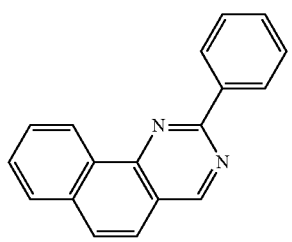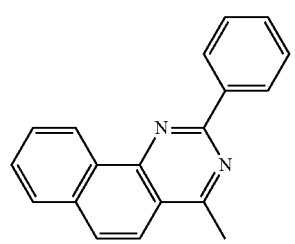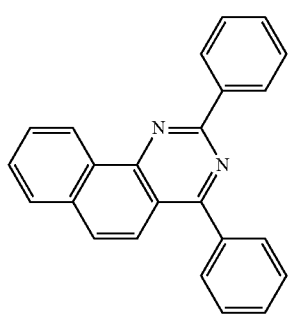

5
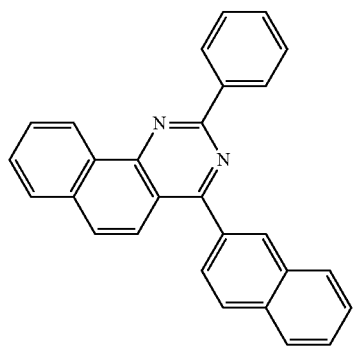
6
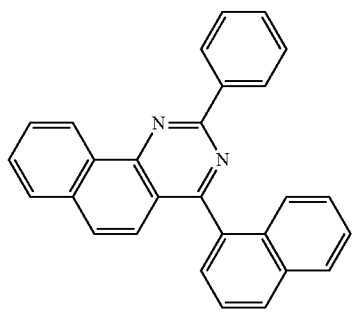
7
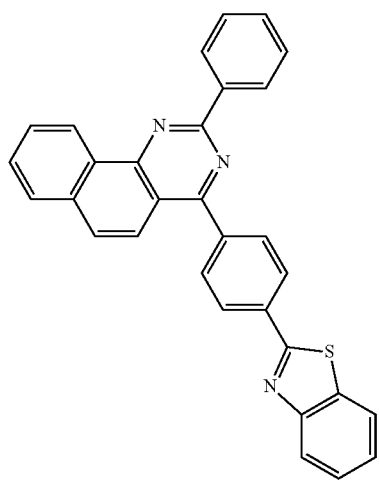
8
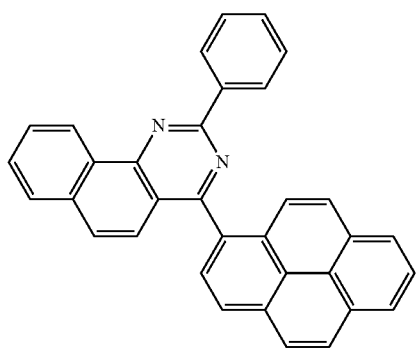
9
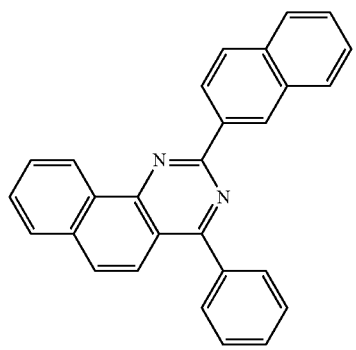
10
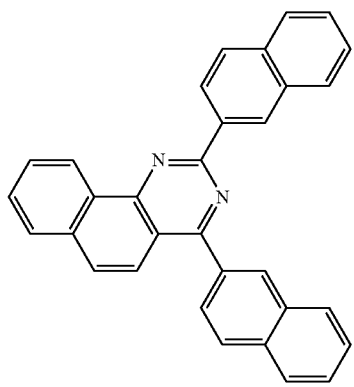

11
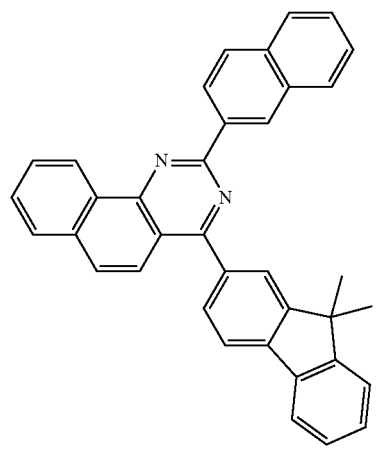
12
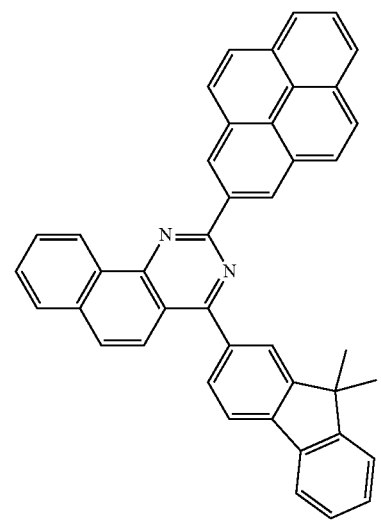
13
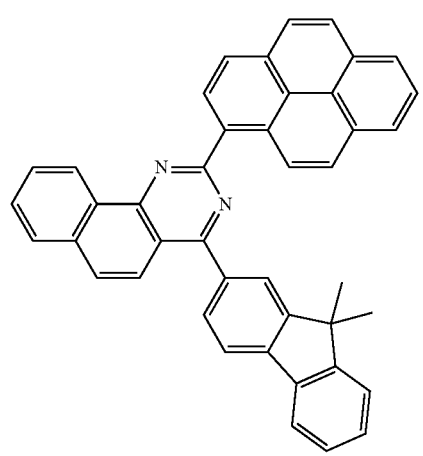
14
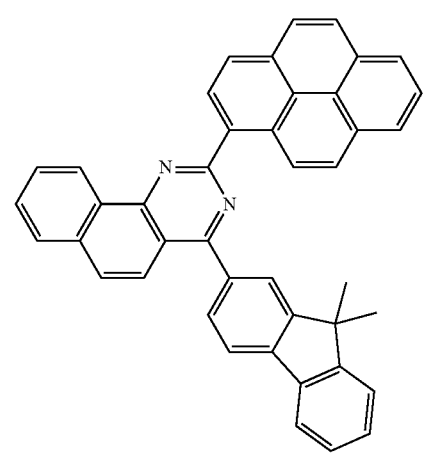
15
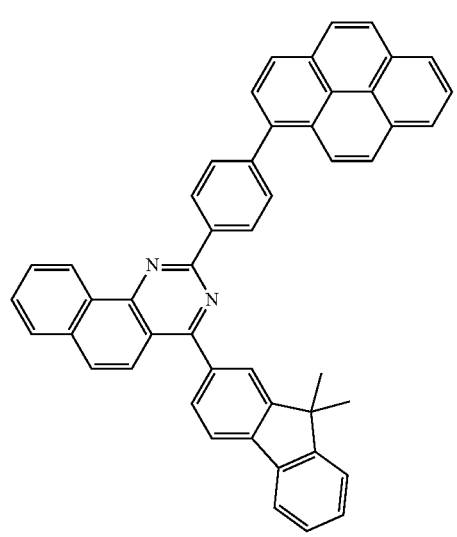
16
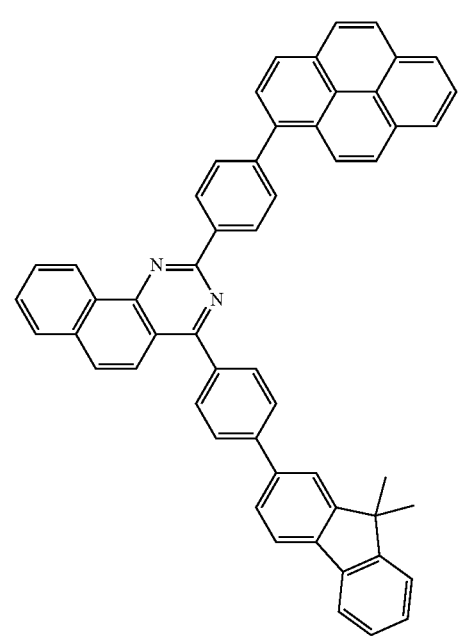

-continued
17
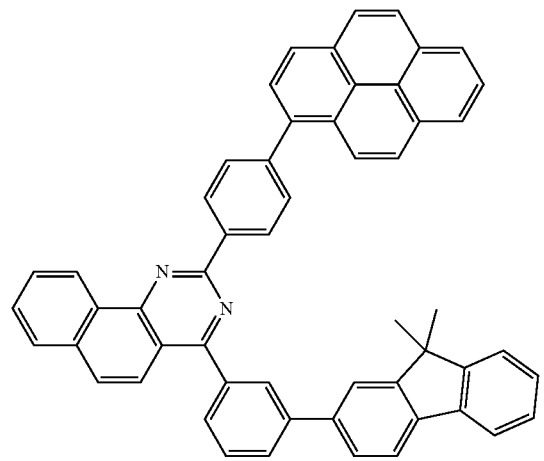
18
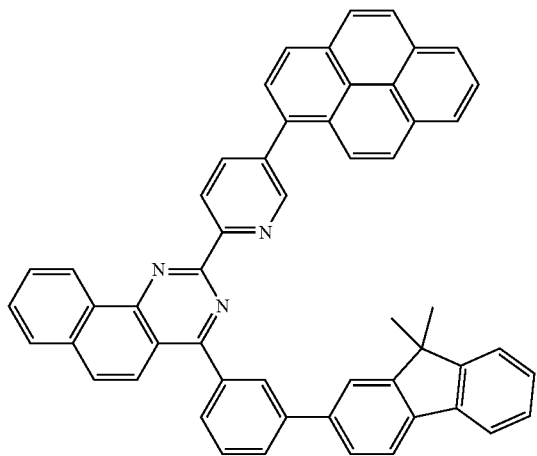
19
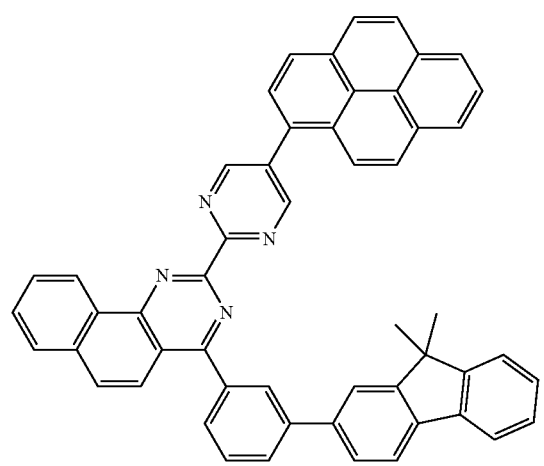
20
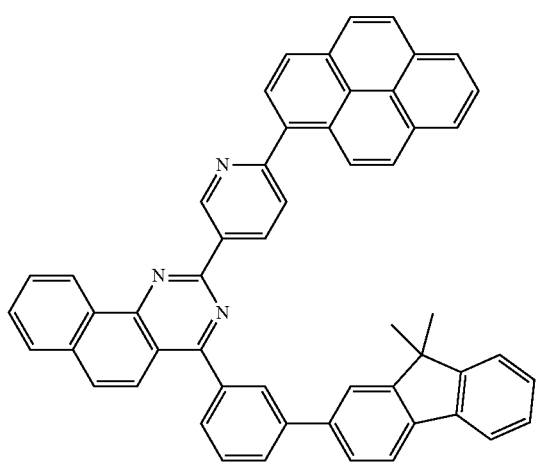
21
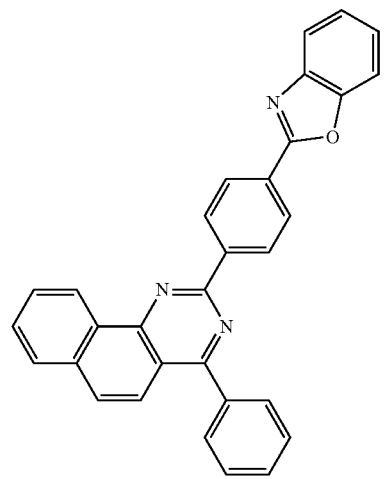
22
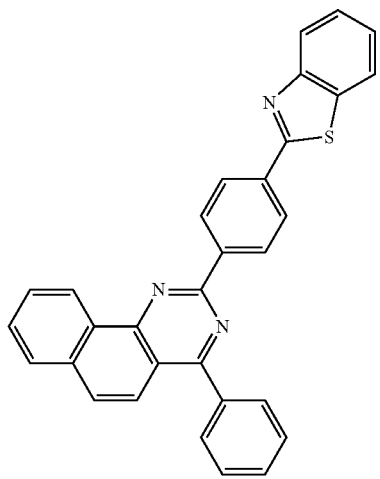

23 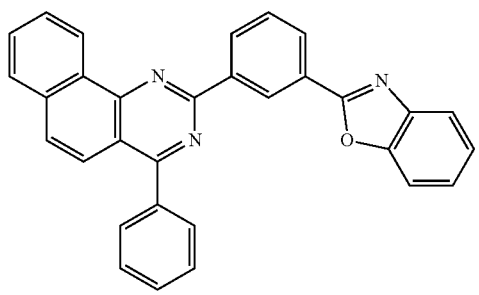
24 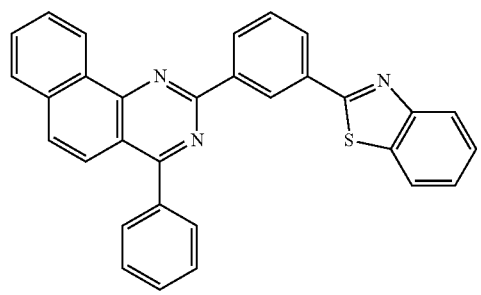
25 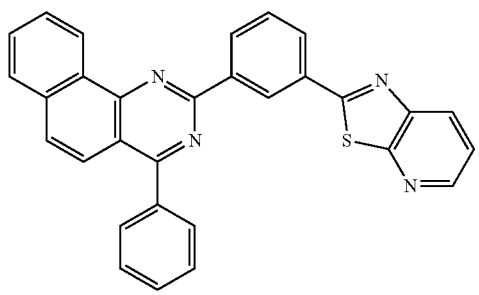
26 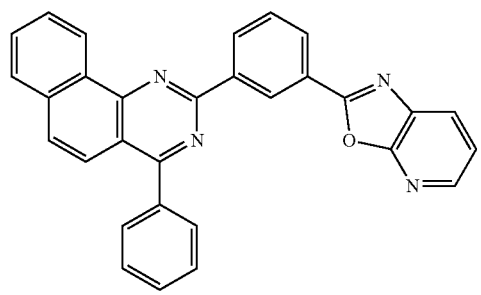
27
28 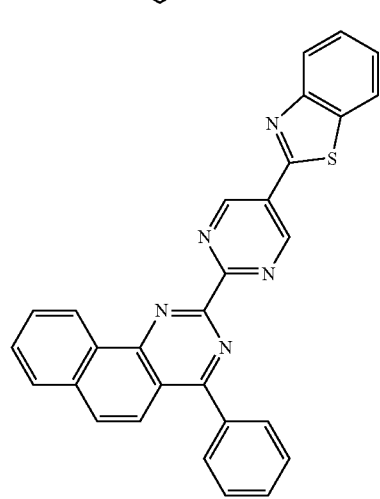
29 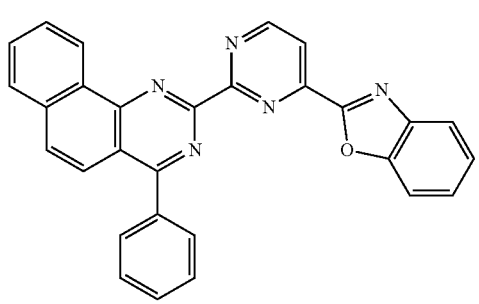
30 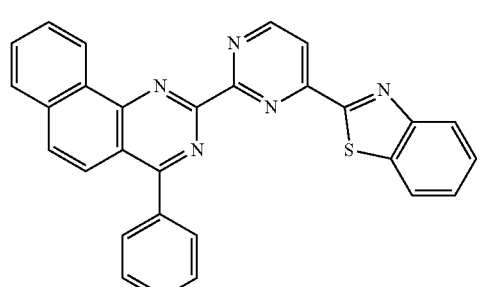
31 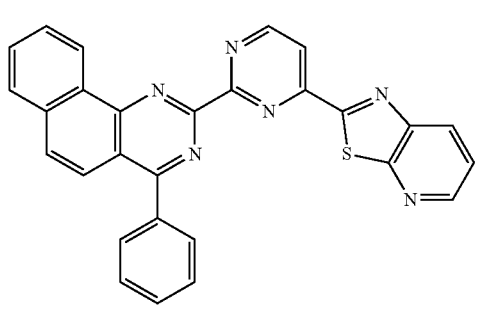
32 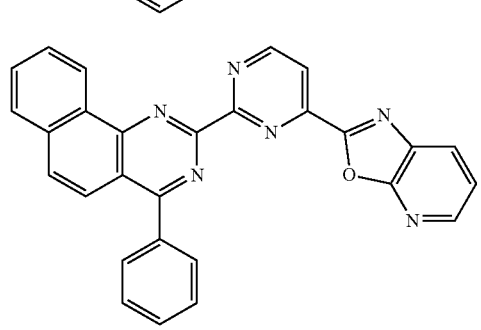

-continued
33
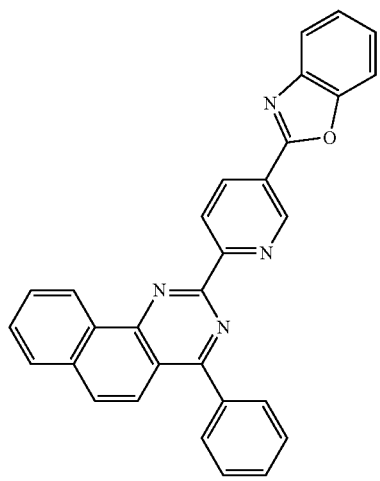
34
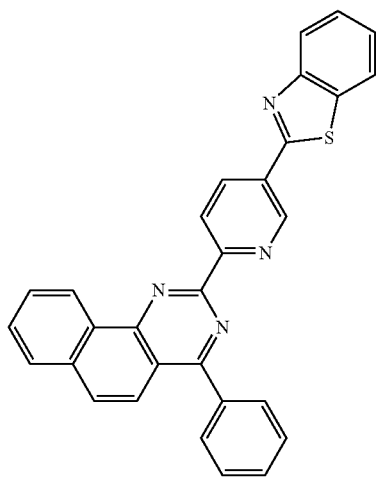
35
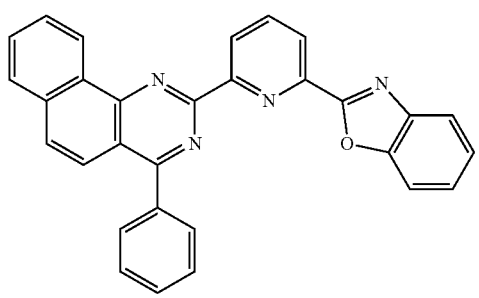
36
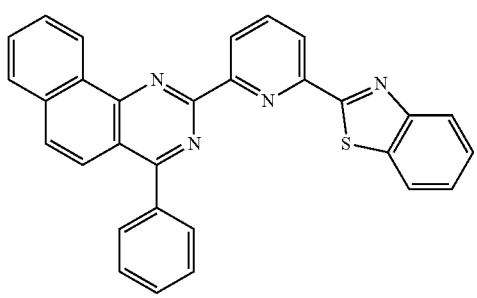
37
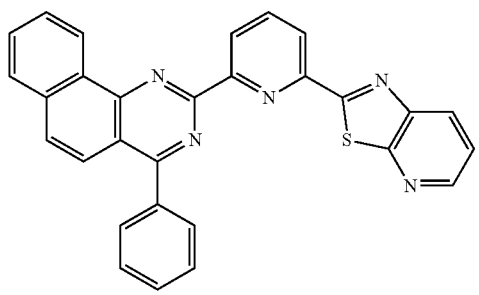
38
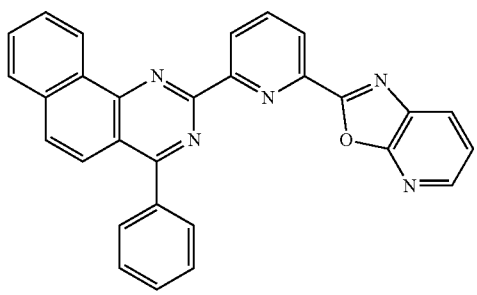
39
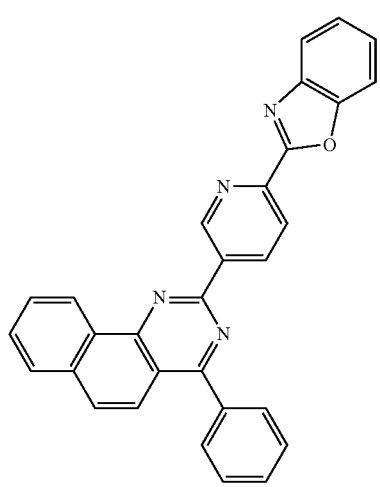
40
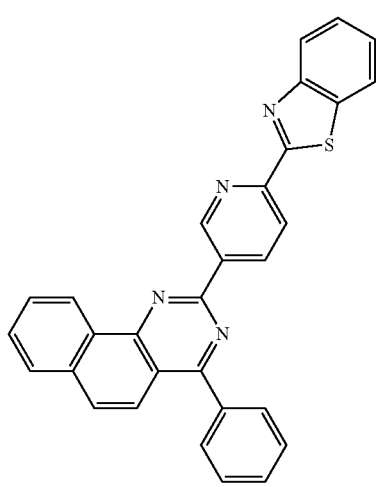

-continued
41
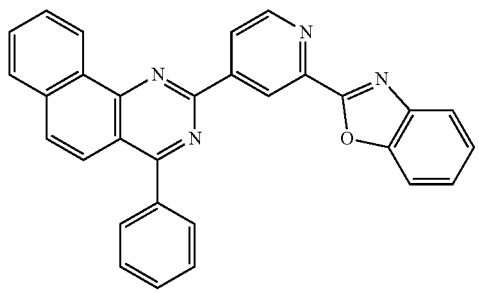
42
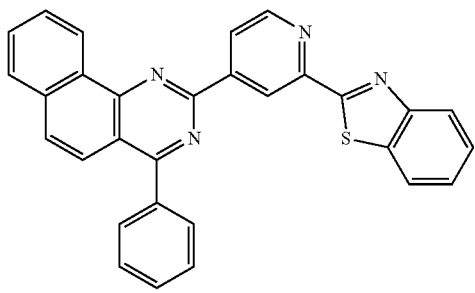
43
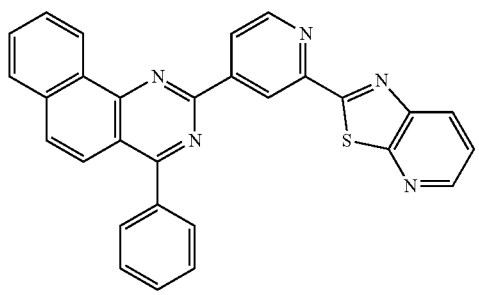
44
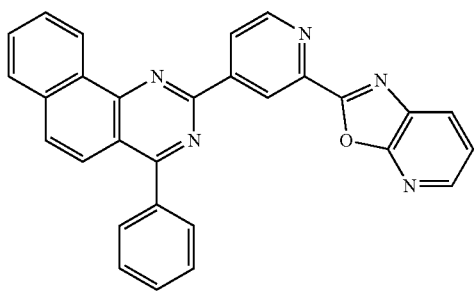
45
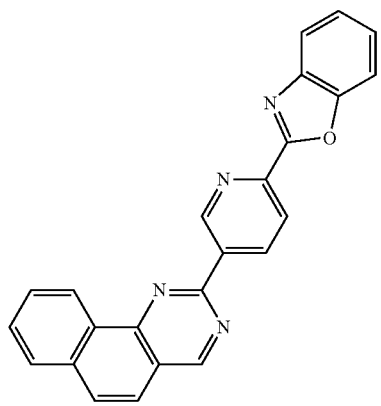
46
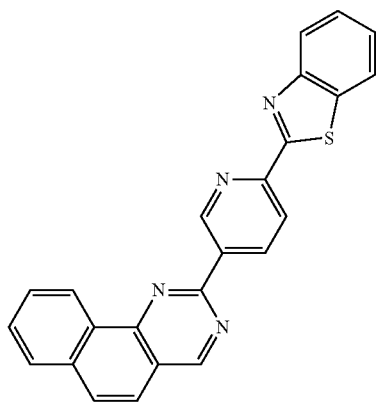
47
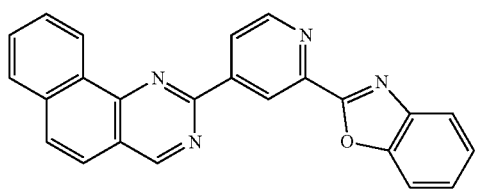
48
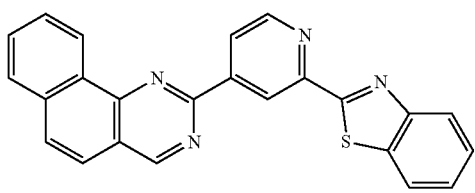
49
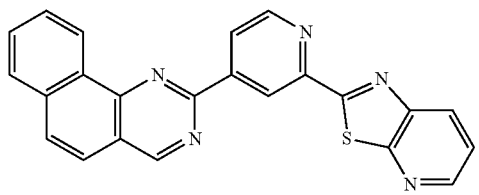
50
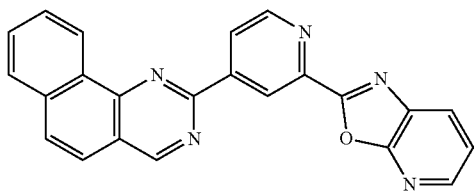

-continued
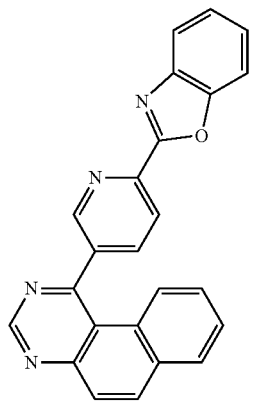
51
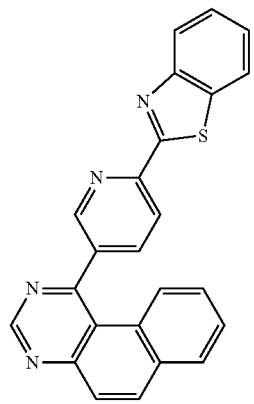
52
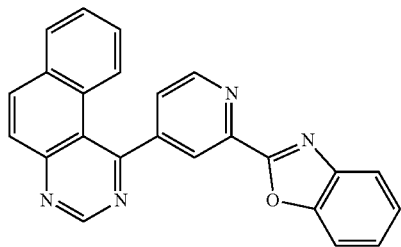
53
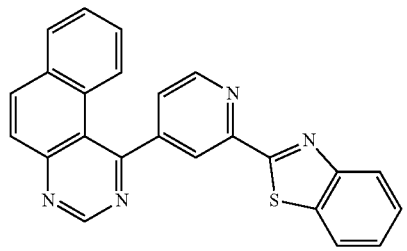
54
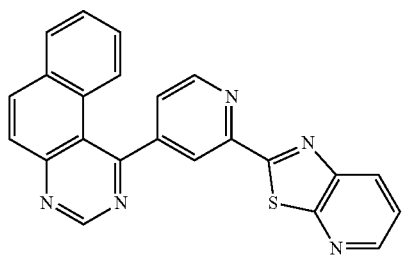
55
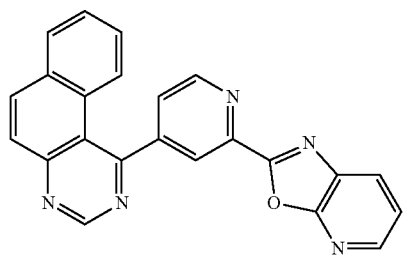
56
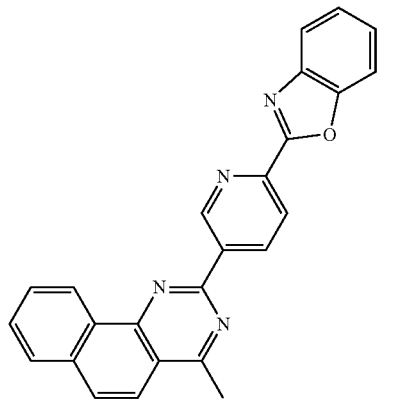
57
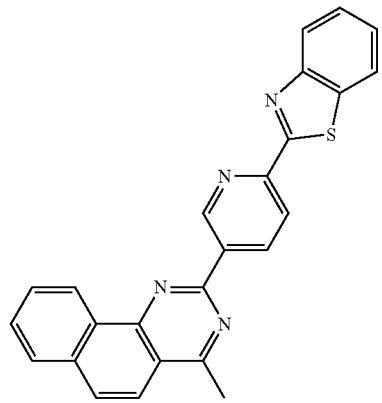
58
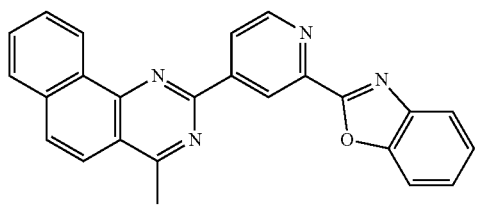
59
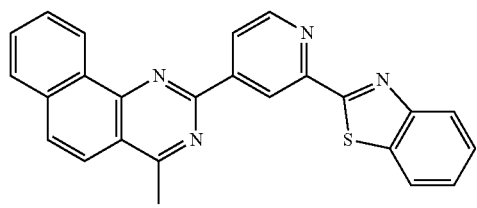
60

23
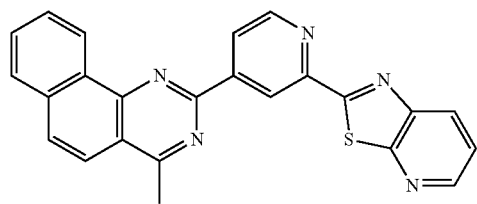
24
-continued
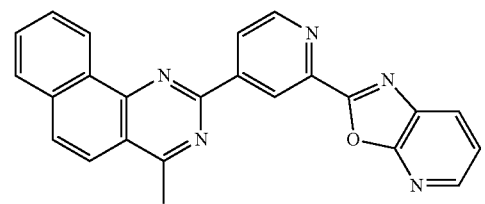
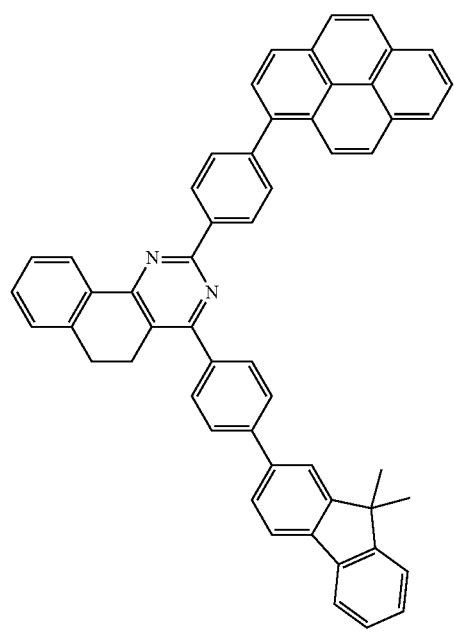
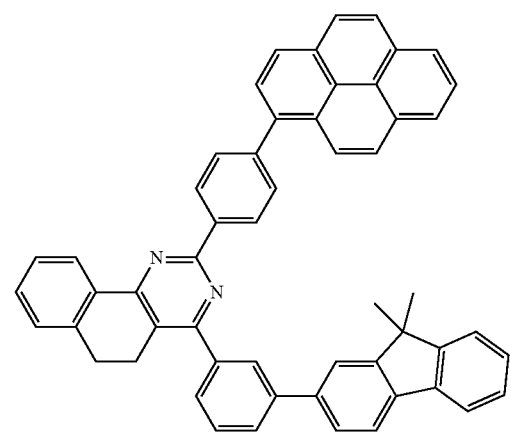
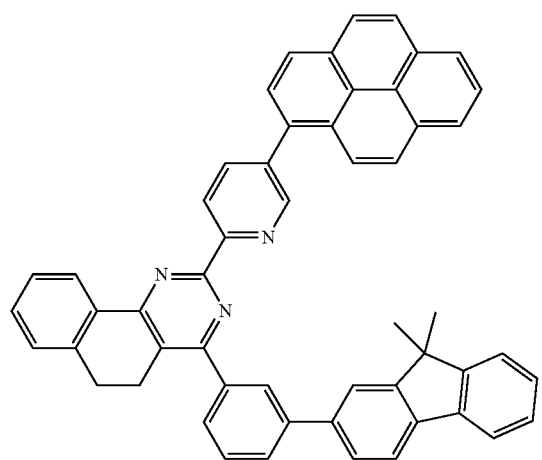
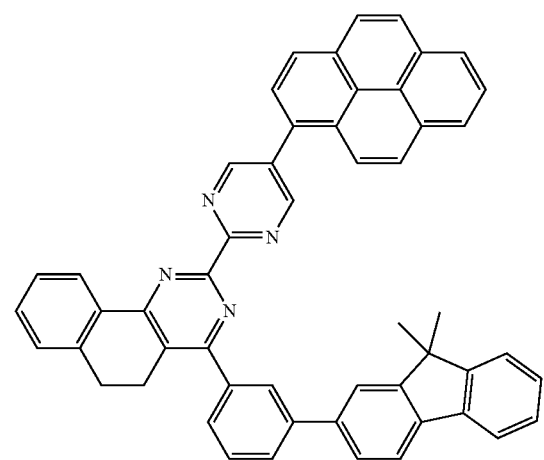

-continued
67
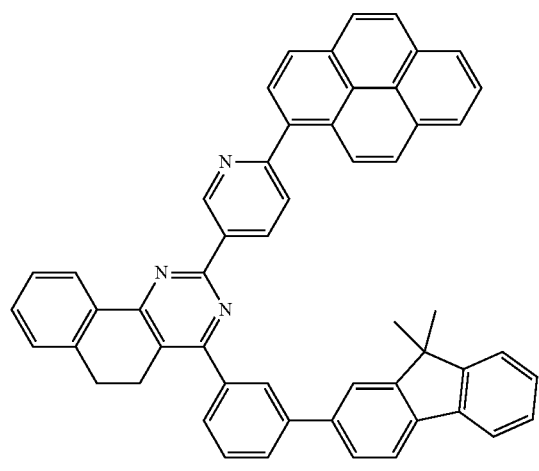
68
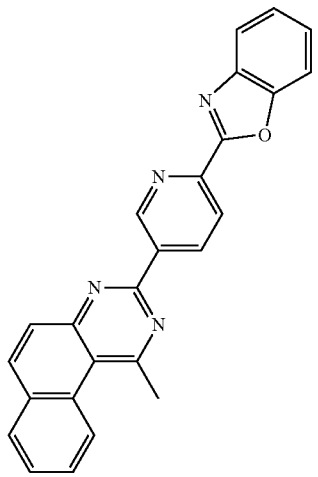
69
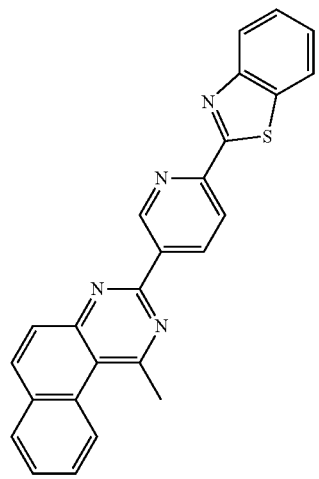
70
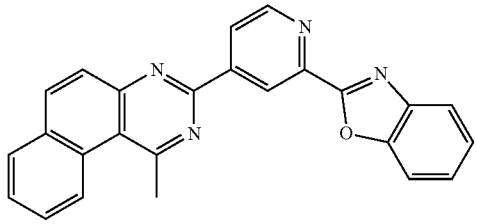
71
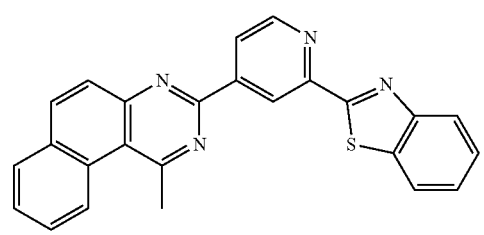
72
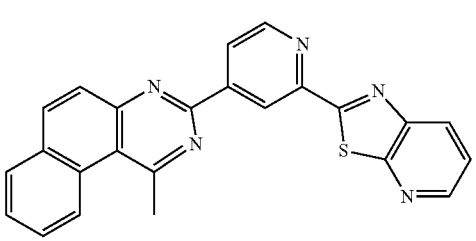

-continued
73
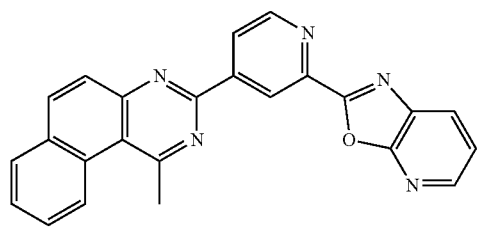
74
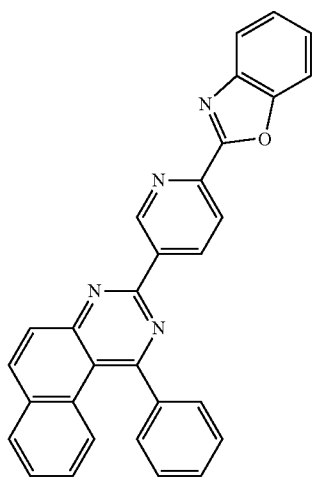
75
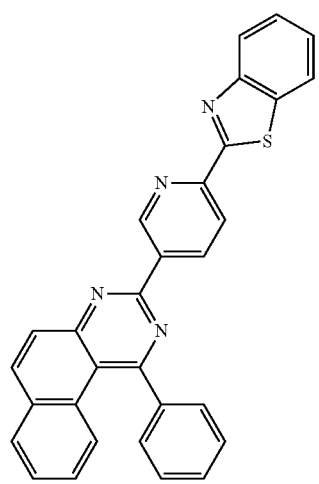
76
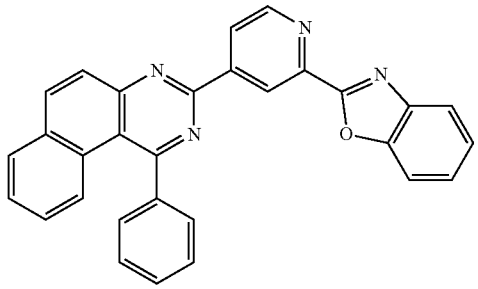
77
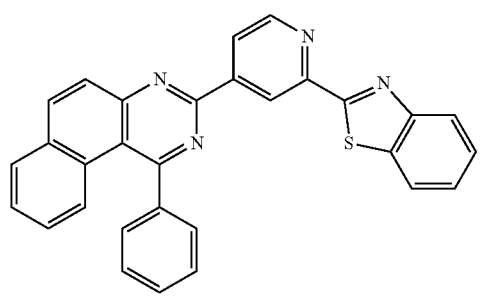
78
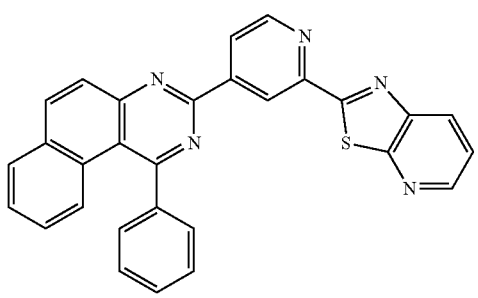

-continued
79
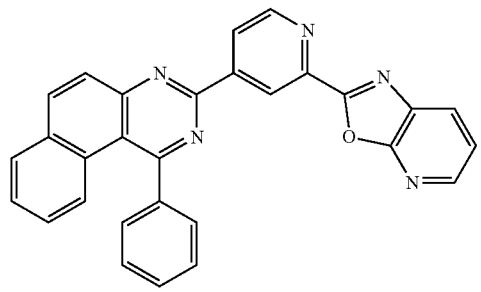
80
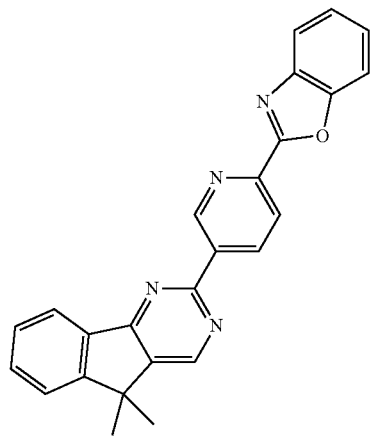
81
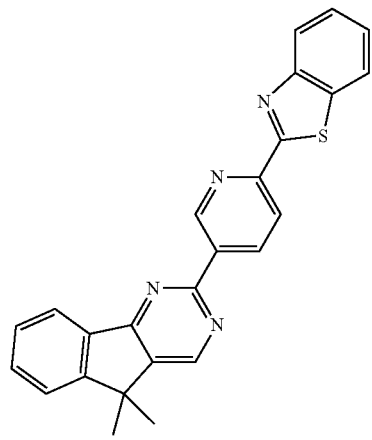
82
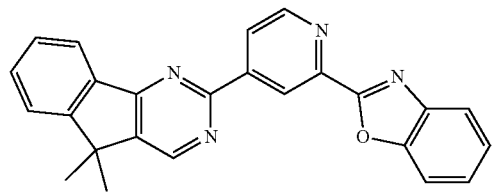
83
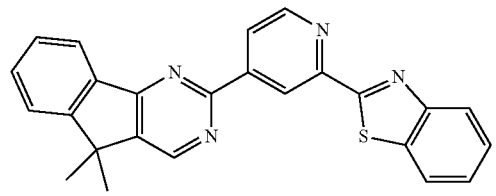
84
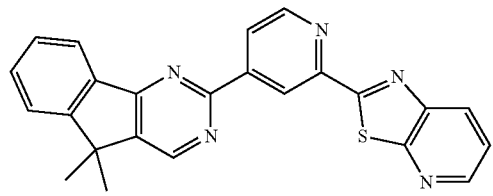
85
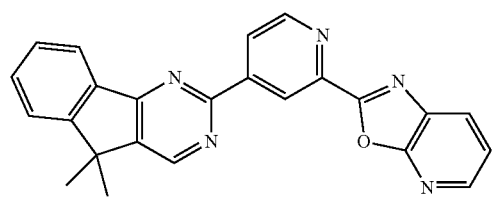
86
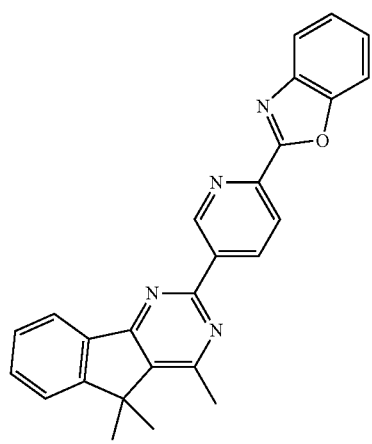

-continued
| 87 | 88 |
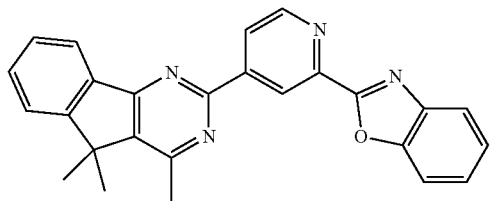
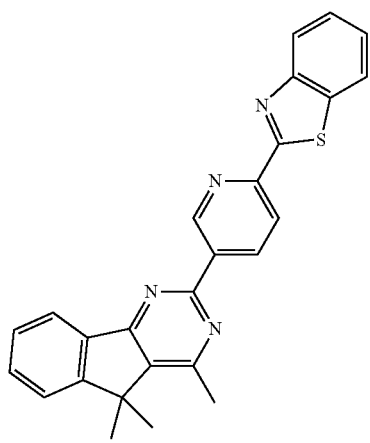
| 89 | 90 |
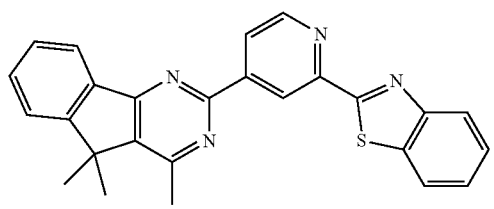
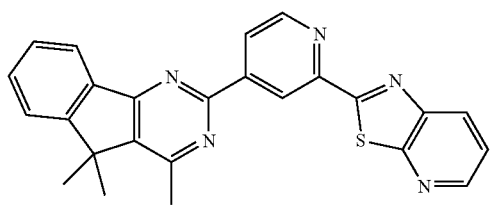
| 91 | 92 |
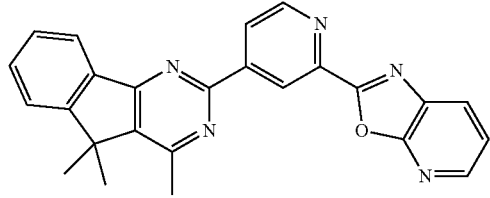
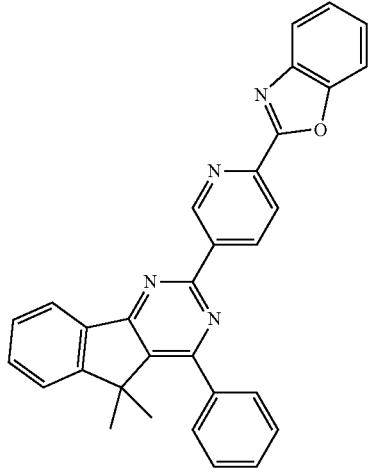
| 93 | 94 |
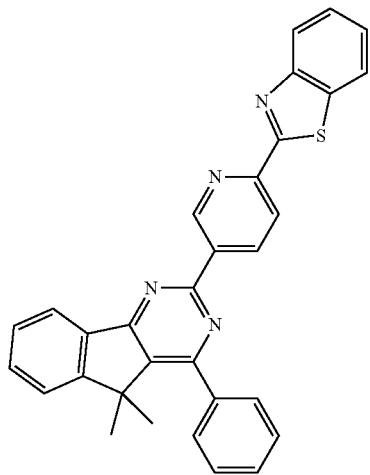
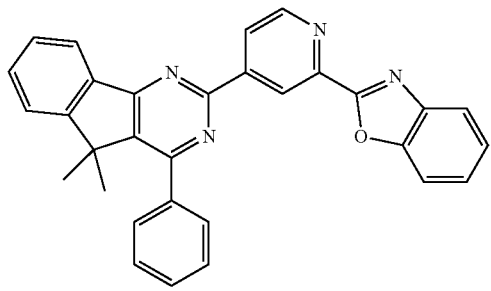

-continued
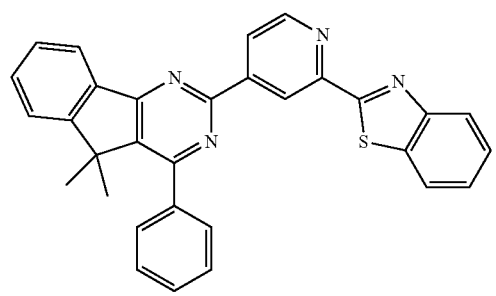
95
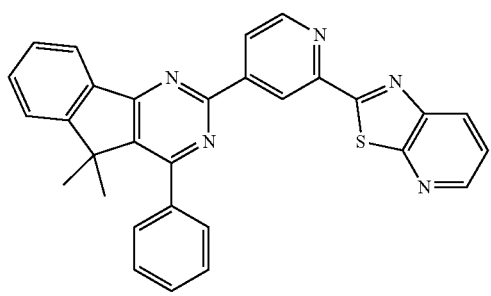
96
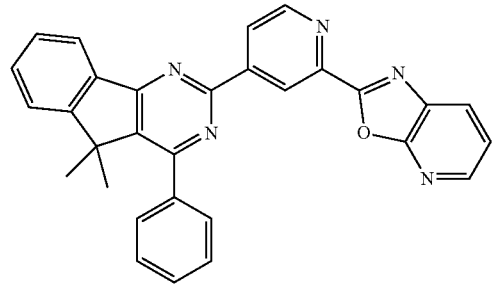
97
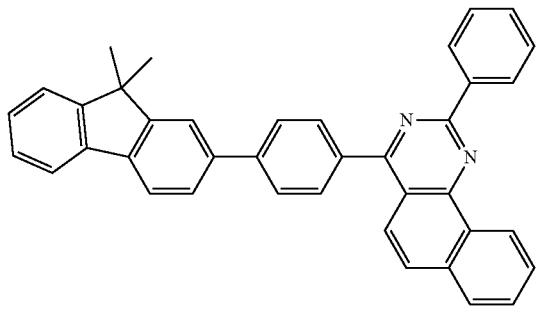
98
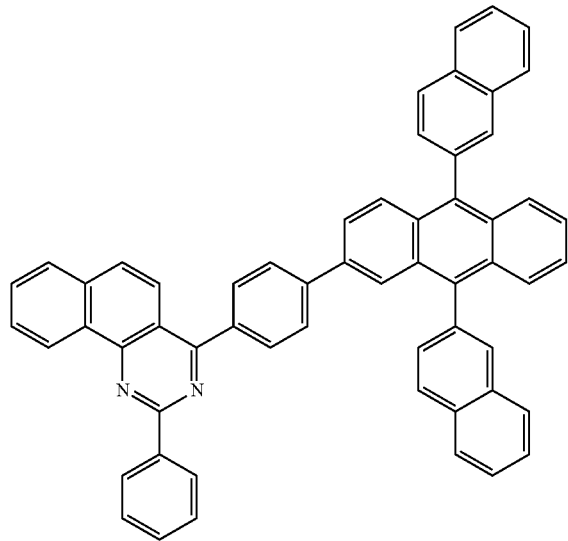
99
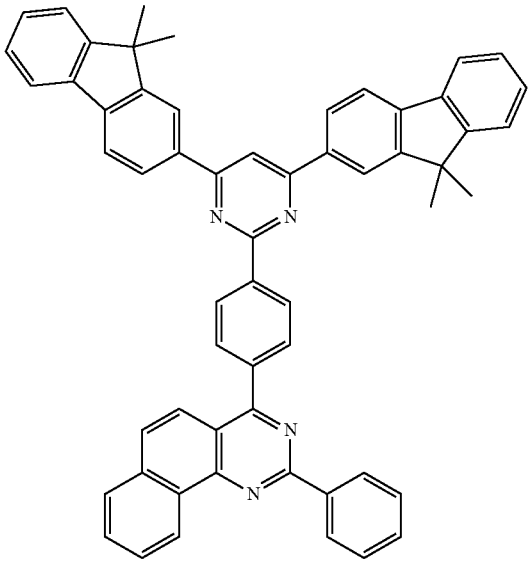
100

-continued
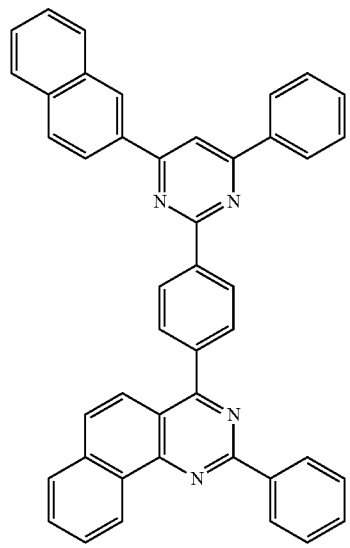
101
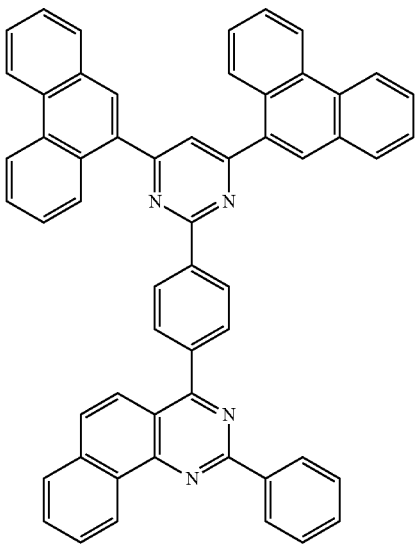
102
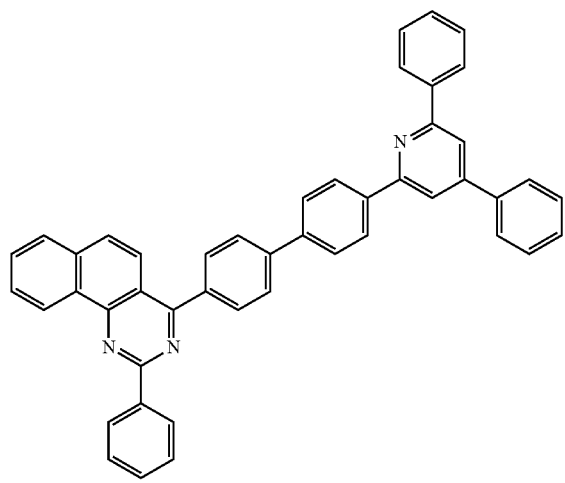
103
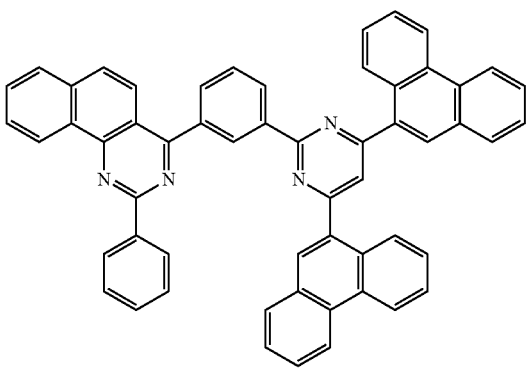
104
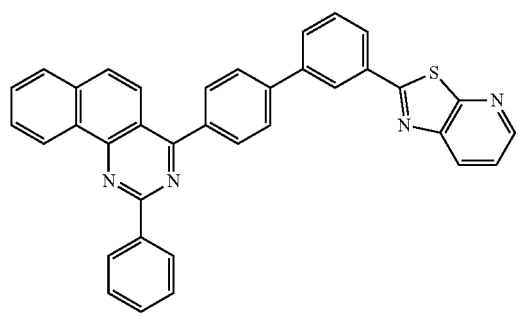
105
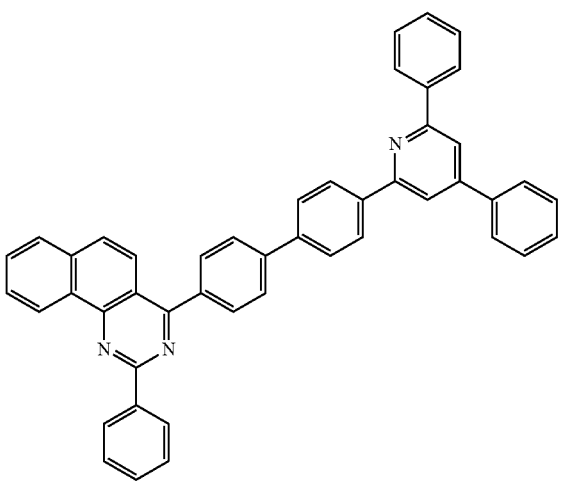
106

107
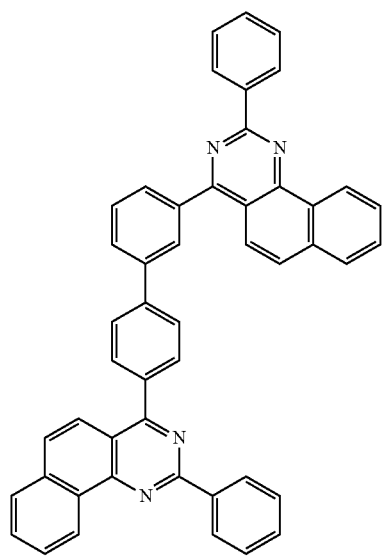
108
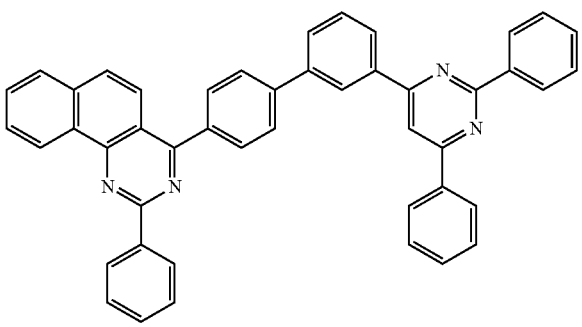
109
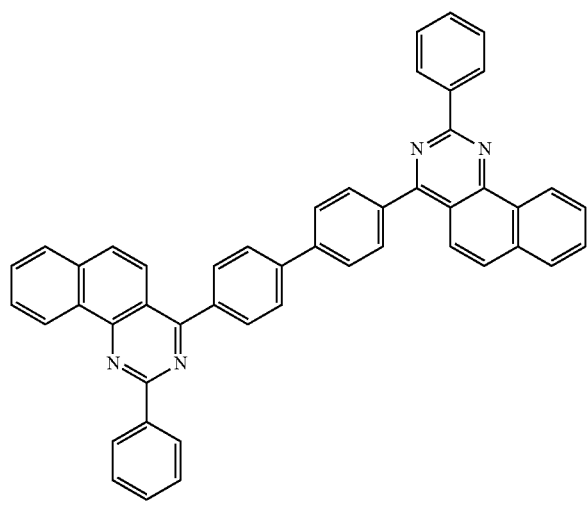
110
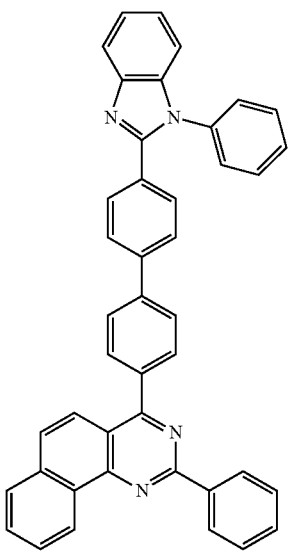

-continued
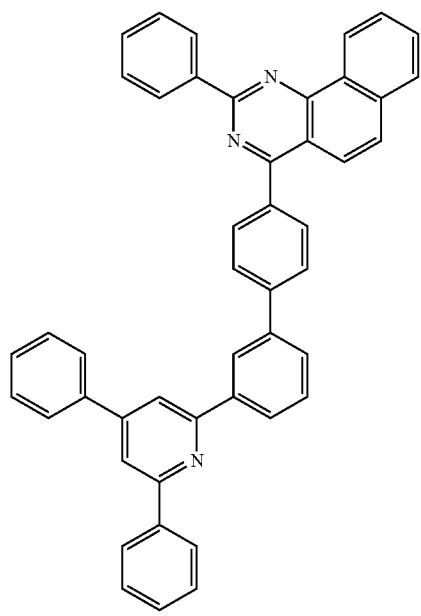
111
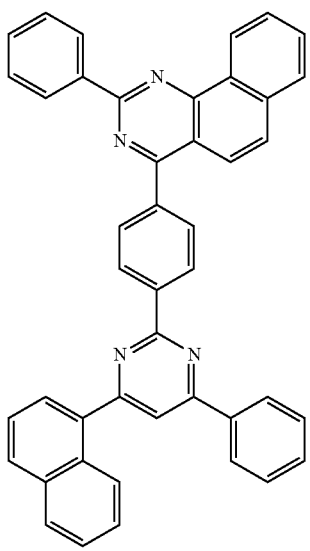
112
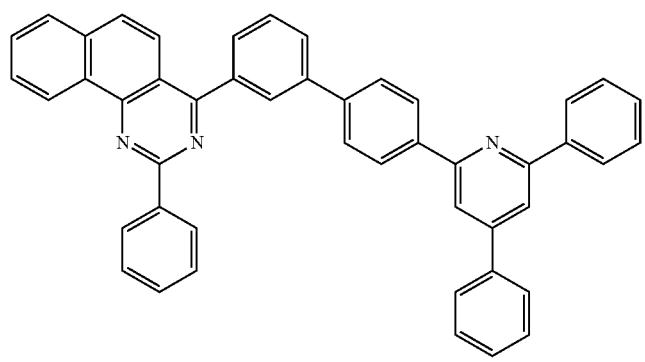
113
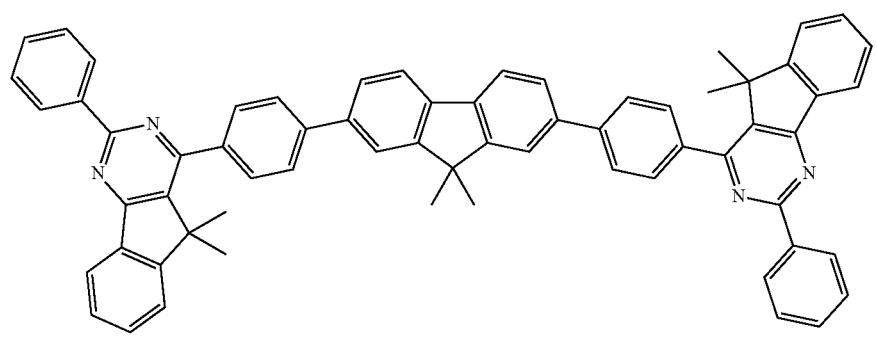
114
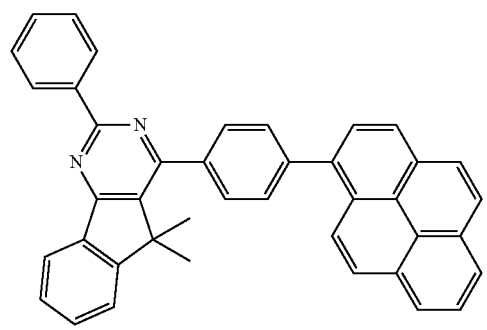
115
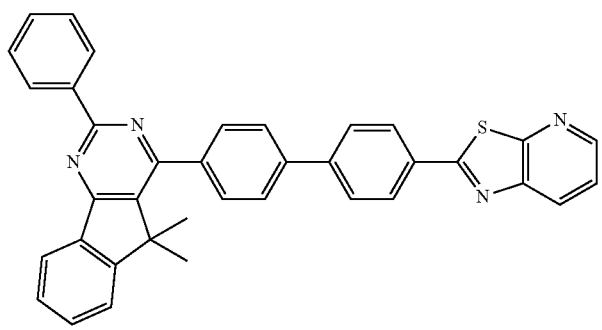
116

-continued
117
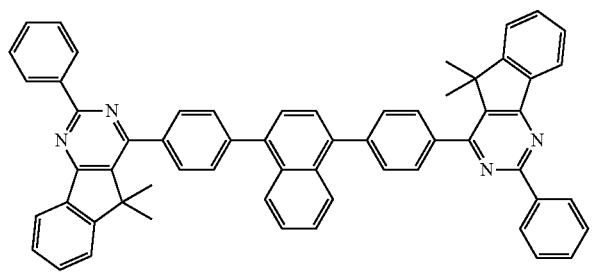
118
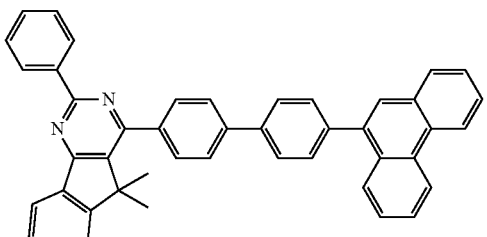
119
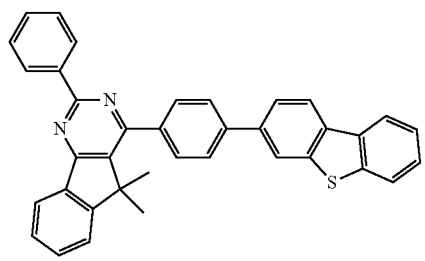
120
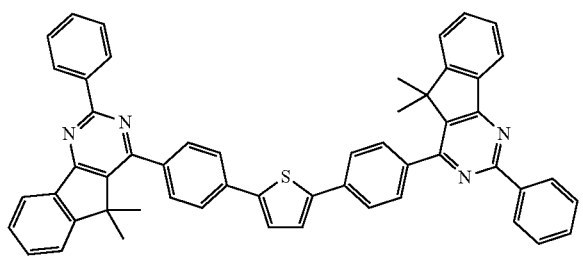
121
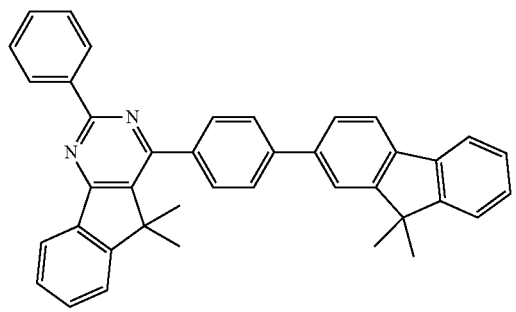
122
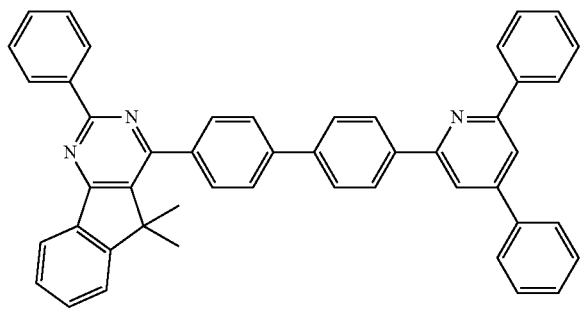
123
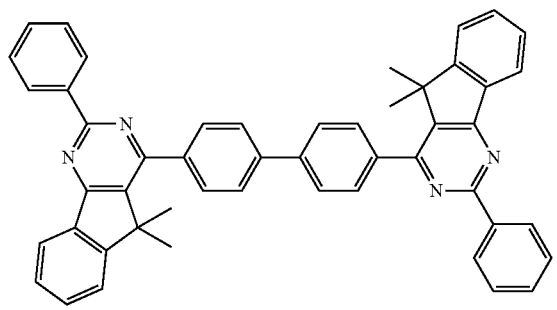
124
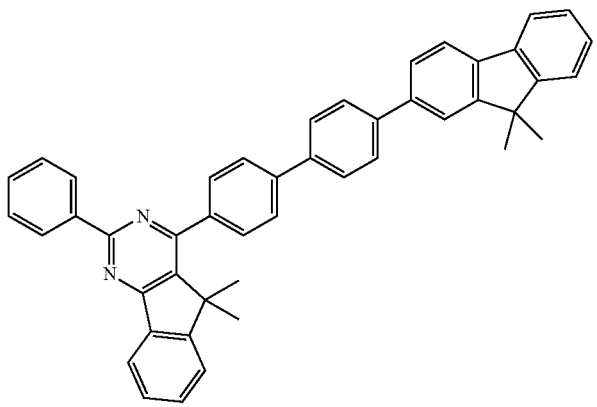

-continued
125
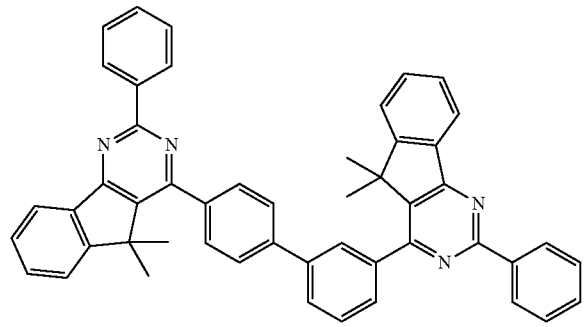
126
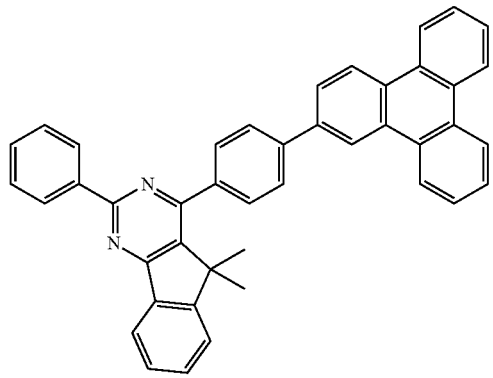
127
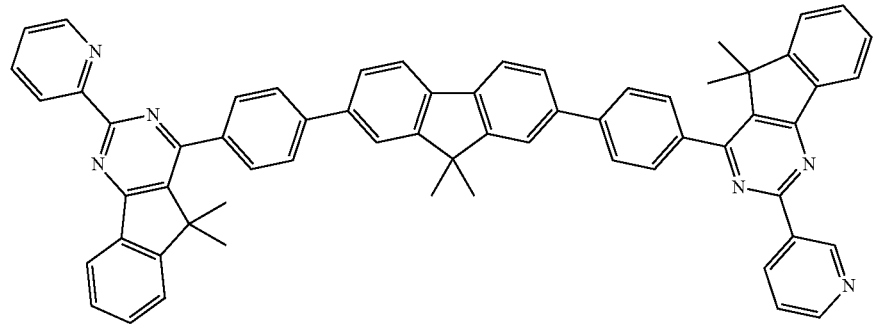
128
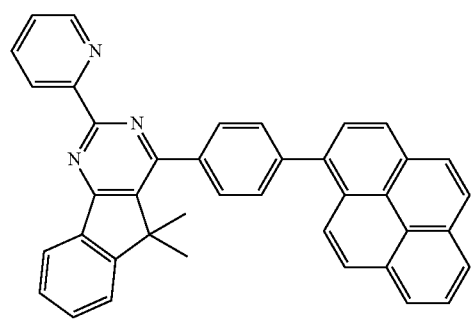
129
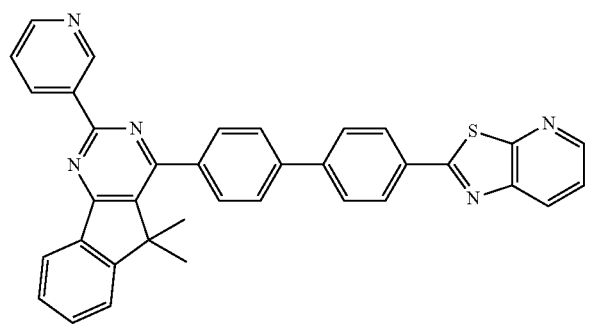
130
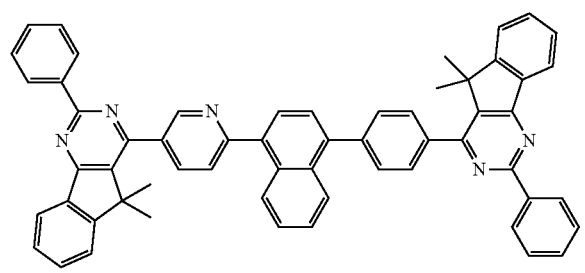
131
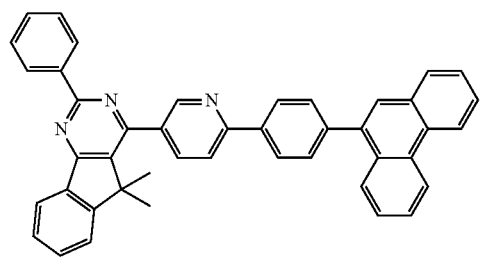
132
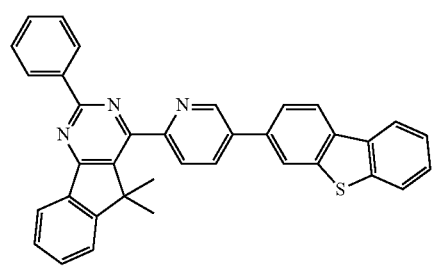
133
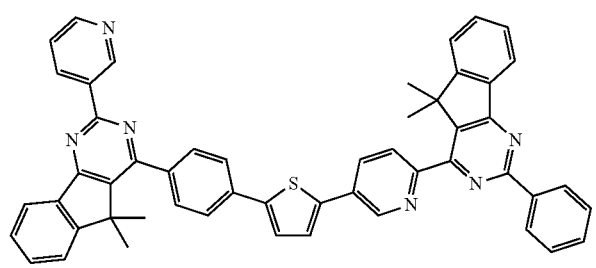

-continued

134

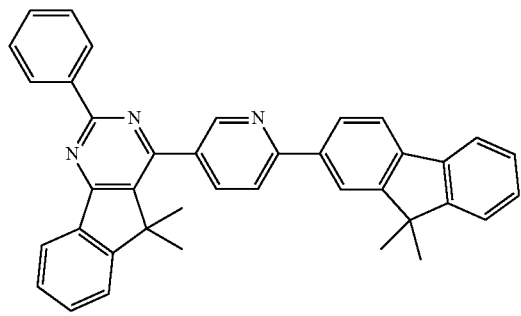

135

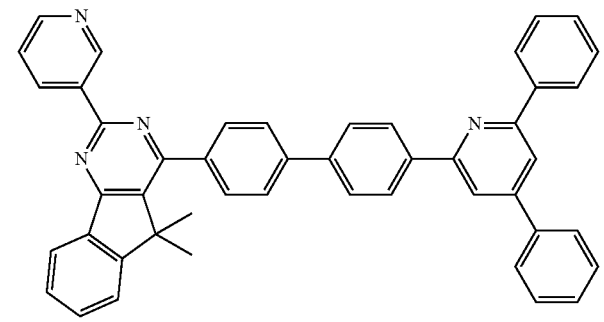

136

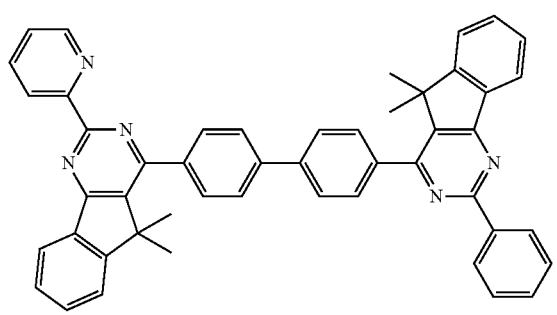

137

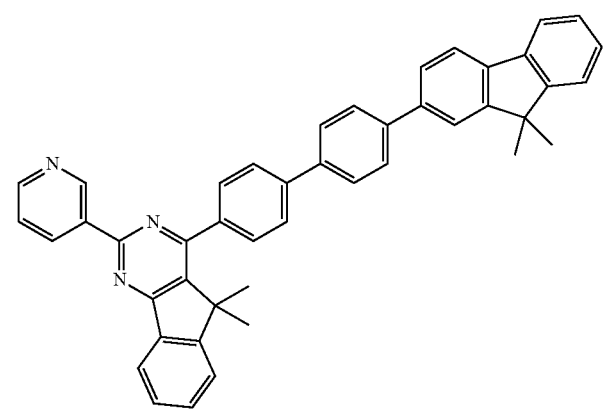

138

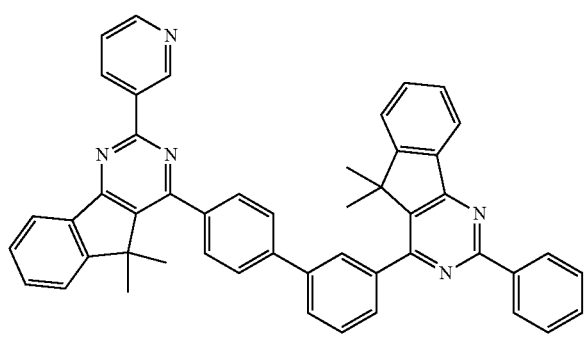

139

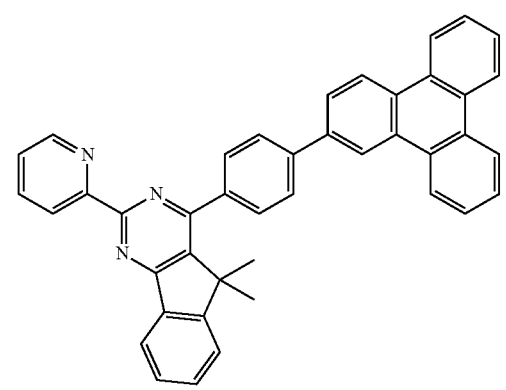

Among the electron transport materials according to the present invention, a process of preparing an electron transport material of Chemical Formula 2 when x and y are 1 is represented by the following Reaction Formula 1, and a process of preparing an electron transport material of Chemical Formula 2 in the case in which x is 3 and y is 1 is represented by the following Reaction Formulas 2 to 4. However, The electron transport material is not limited thereto, but may be prepared by an organic reaction known in the art.

[Reaction Formula 1]

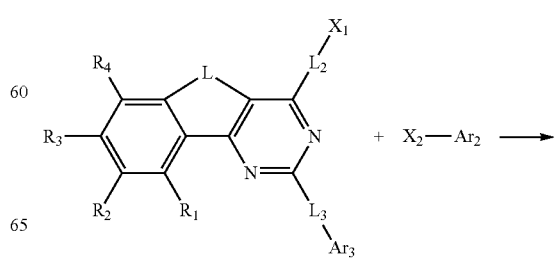

-continued
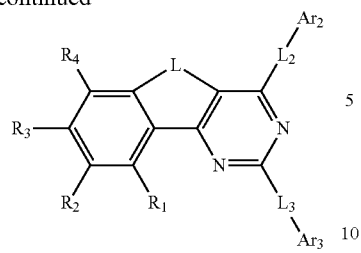
5
[R₁ to R₄, L, L₂, L₃, Ar₂, and Ar₃ each has the same definition in Chemical Formula 2, X₁ and X₂ are halogen or
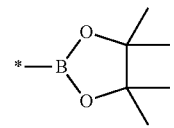 [SMILES: *B1OC(C)(C)C(C)(C)O1]
but are not equal to each other.]
[Reaction Formula 2]
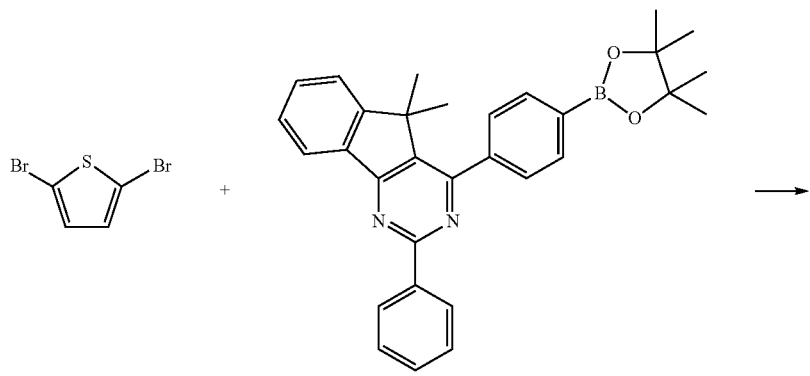
[Reaction Formula 3]
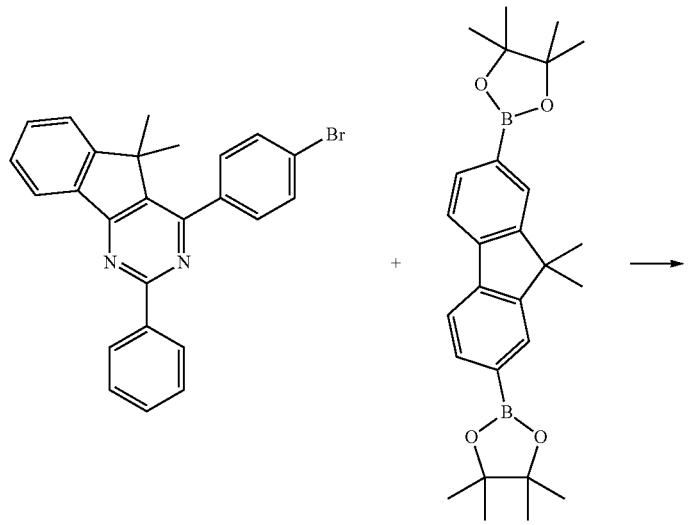

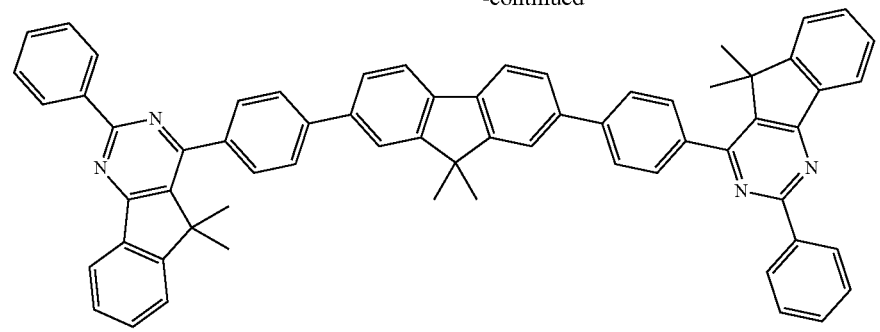

[Reaction Formula 4]

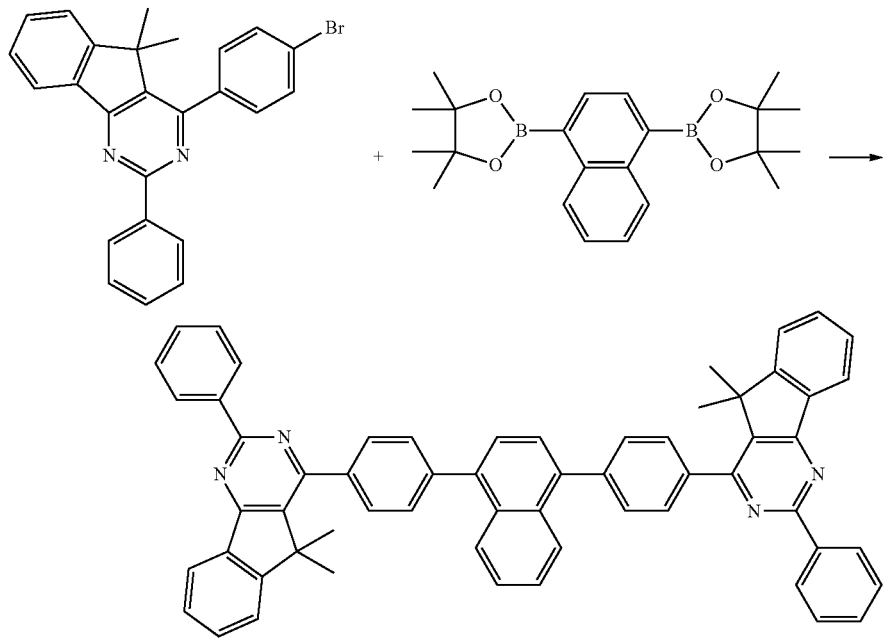

In another general aspect, there is provided an organic electroluminescent device including a first electrode; a second electrode; and at least one organic layer interposed between the first and second electrodes, wherein the organic layer includes an electron transport layer containing an electron transport material of Chemical Formula 1. In the case in which the electron transport material of Chemical Formula 1 is used in the electron transport layer, driving voltage may be decreased, such that an increase in power efficiency may be induced, thereby decreasing consumption power.

Further, the organic layer may include at least one electron transport layer in which the electron transport material of Chemical Formula 1 is contained and at least one luminescent layer configured of a fluorescent host and a fluorescent dopant or a phosphorescent host and a phosphorescent dopant, wherein the fluorescent host, the fluorescent dopant, the phosphorescent host, or the phosphorescent dopant are not particularly limited.

DETAILED DESCRIPTION OF EMBODIMENTS

Figure 1:
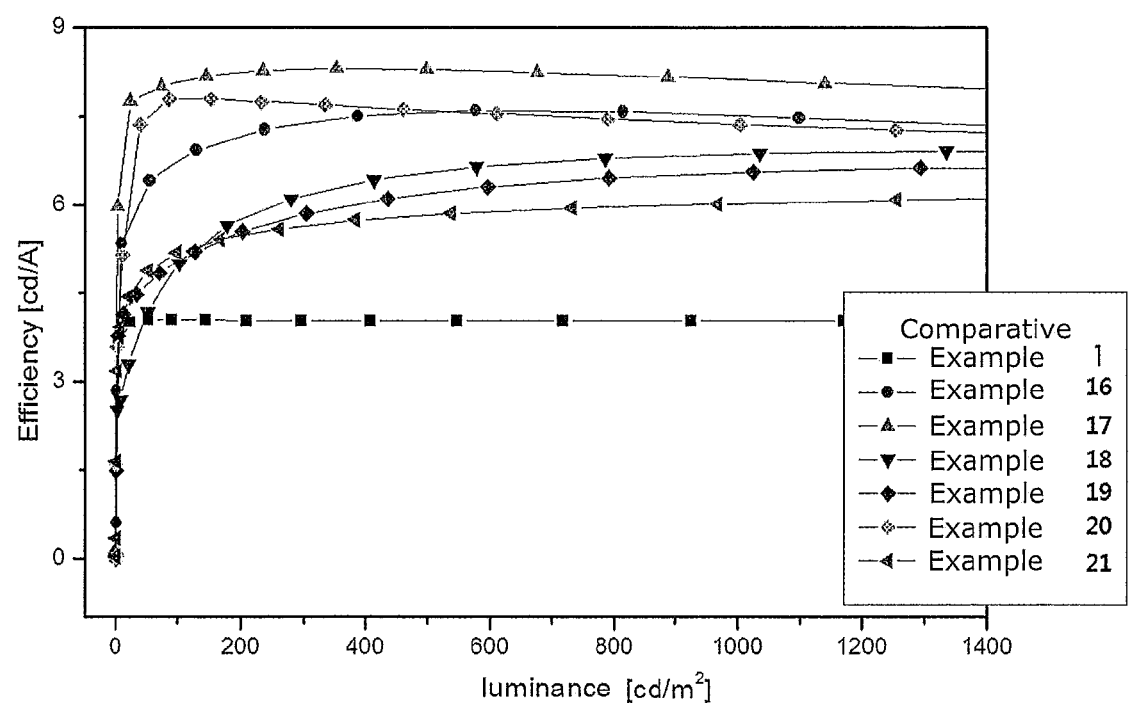
FIG. 1 is a graph showing efficiency (cd/A) and luminance (cd/m$^2$) of organic electroluminescent devices manufactured in Examples 7 to 12 and Comparative Example 1.

Hereinafter, an electron transport compound according to the present invention, a preparing method thereof, and luminescence properties of a device will be described in detail using a representative compound of the present invention as an example. However, the examples are for illustrating the present invention and not for limiting the present invention.

Preparation Example 1

Preparation of Compound A

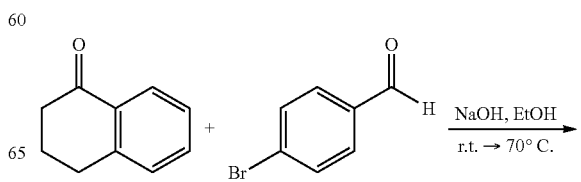

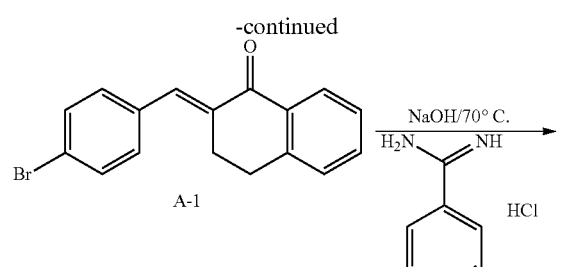

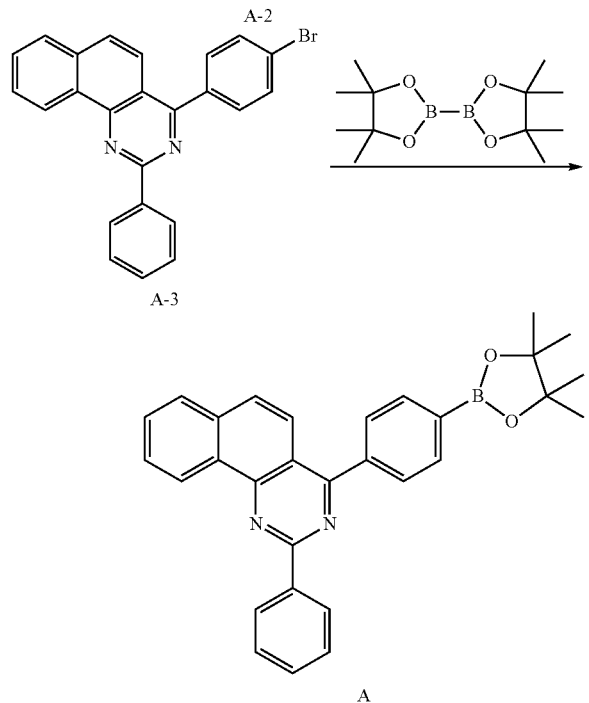

Preparation of Compound A-1

Alpha-tetralone (80 g, 0.55 mol) and 4-bromobenzaldehyde (106.5 g, 0.58 mol) were dissolved in ethanol (480 mL), and then sodium hydroxide (27.4 g, 0.68 mol) was slowly added thereto at 0° C. After the mixture was stirred at room temperature for 3 hours, the prepared solid was separated by filtering under reduced pressure and sequentially washed with methanol, distilled water, and methanol. The washed material was dried, thereby obtaining Compound A-1 (148 g, 69.8%) as a yellow solid.

$^1$H NMR (CDCl$_3$) δ 7.97 (1H, d), 7.67-7.54 (7H, m), 7.46 (1H, t), 2.91 (2H, t), 2.73 (2H, t)

Preparation of Compound A-2

Compound A-1 (80 g, 0.26 mol), benzamidinehydrochloride (44 g, 0.28 mol), sodium hydroxide (15 g, 0.38 mol), and ethanol (1200 mL) were mixed and refluxed for 12 hours. When the reaction was completed, the resultant material was cooled to room temperature, and the precipitated solid was filtered under reduced pressure and washed with water and ethanol. The washed material was dried, thereby obtaining Compound A-2 (50 g, 47.4%) as a white solid.

$^1$H NMR (CDCl$_3$) δ 8.65 (3H, m), 7.70 (4H, q), 7.51 (5H, m), 7.28 (1H, s), 3.09 (2H, t), 2.93 (2H, t)

Preparation of Compound A-3

Compound A-2 (20 g, 0.048 mol), 2,3-dichloro-5,6-dicyanoparabenzoquinone (DDQ, 27.5 g, 0.12 mol), and dichlorobenzene (200 mL) were mixed and stirred at 120° C. for 4 hours. When the reaction was completed, the resultant material was cooled to room temperature and dispersed in methanol, followed by filtering under reduced pressure, thereby obtaining Compound A-3 (13.2 g, 66.3%) as a white solid.

$^1$H NMR (CDCl$_3$) δ 8.65 (3H, m), 7.70 (6H, q), 7.51 (7H, m), 7.28 (1H, s)

Preparation of Compound A

Compound A-3 (10 g, 24.3 mmol), bis(pinacolato)diboron (6.48 g, 25.5 mmol), 1,4-dioxane (200 mL), 1,1'-bis(diphenylphosphino)ferrocene-palladium(II)dichloride dichloromethane complex (0.36 g, 0.49 mmol), and potassium acetate (4.8 g, 48.6 mmol) were mixed and stirred under reflux. After 12 hours, the reactant was cooled to room temperature, and an organic layer was extracted by adding saturated sodium chloride aqueous solution and ethyl acetate, dried over magnesium sulfate, and then treated with activated charcoal, followed by filtering with celite. After a solid prepared by concentrating the filtrate under reduced pressure was suspended in hexane, the suspension was filtered again and washed with hexane, thereby obtaining Compound A (9.8 g, 87.9%) as a yellow solid.

$^1$H NMR (CDCl$_3$) δ 8.62 (3H, m), 7.68 (6H, q), 7.55 (7H, m), 7.12 (1H, s), 1.40 (s, 12H)

Preparation Example 2

Preparation of Compound B

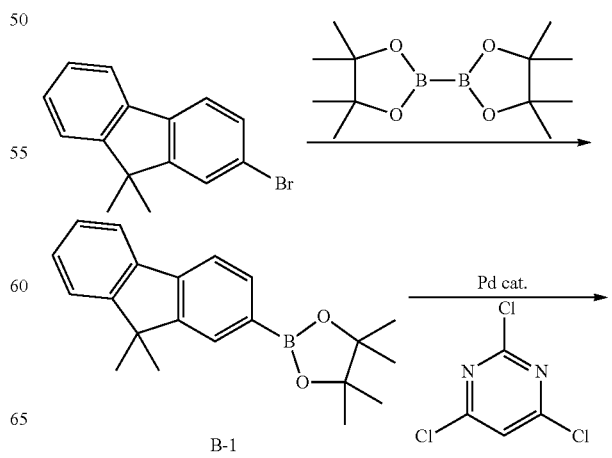

-continued

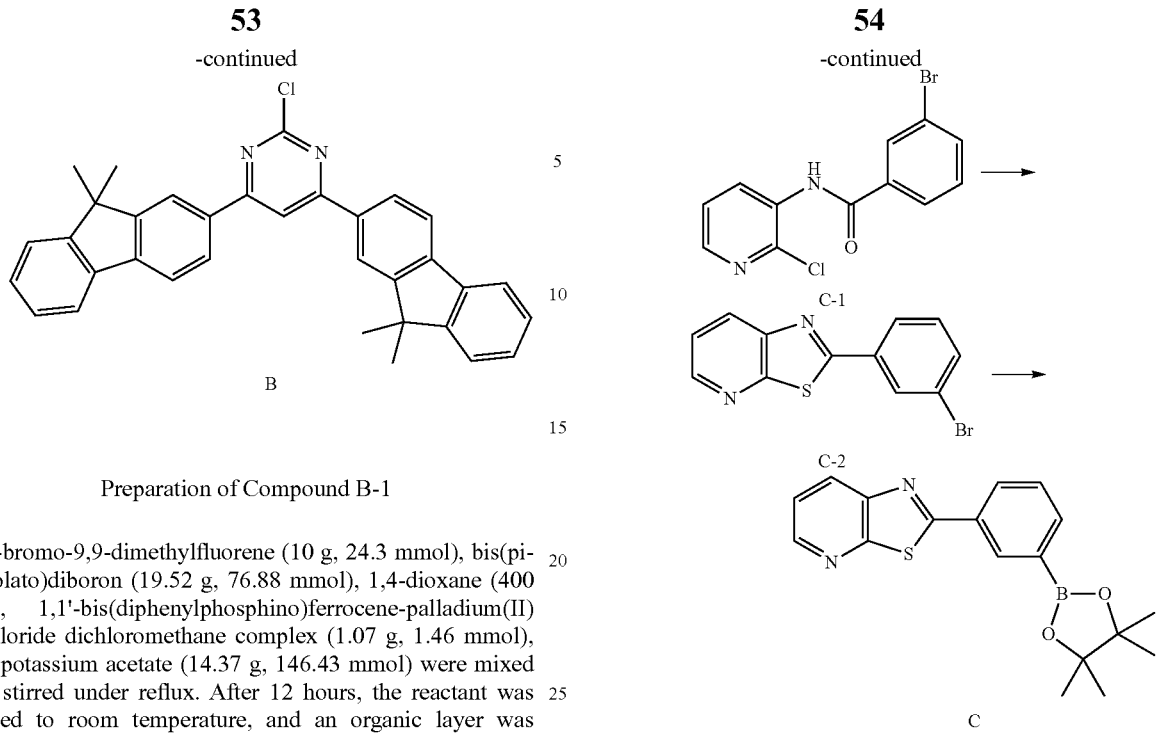

Preparation of Compound B-1

2-bromo-9,9-dimethylfluorene (10 g, 24.3 mmol), bis(pinacolato)diboron (19.52 g, 76.88 mmol), 1,4-dioxane (400 mL), 1,1'-bis(diphenylphosphino)ferrocene-palladium(II) dichloride dichloromethane complex (1.07 g, 1.46 mmol), and potassium acetate (14.37 g, 146.43 mmol) were mixed and stirred under reflux. After 12 hours, the reactant was cooled to room temperature, and an organic layer was extracted by adding saturated sodium chloride aqueous solution and ethyl acetate, dried over magnesium sulfate, and then treated with activated charcoal, followed by filtering with celite. After a solid prepared by concentrating the filtrate under reduced pressure was suspended in hexane, the suspension was filtered again and washed with hexane, thereby obtaining Compound B-1 (18 g, 76.8%) as a white solid.

$^1$H NMR (CDCl$_3$) δ 7.78 (2H, d), 7.57 (2H, m), 7.38 (3H, m), 1.58 (s, 6H), 1.40 (s, 12H)

Preparation of Compound B

Trichloropyrimidine (5 g, 27.26 mmol), Compound B-1 (17.6 g, 55.1 mmol), Pd(PPh$_3$)$_4$ (0.63 g, 0.55 mmol), K$_2$CO$_3$ (7.53 g, 54.52 mmol), distilled water (25 mL), and THF (50 mL) were mixed and stirred under reflux for 12 hours. After an organic layer was extracted with MC, the extracted organic layer was concentrated under reduced pressure and washed with acetone, thereby obtaining Compound B (9.3 g, 68.4%).

$^1$H NMR (CDCl$_3$) δ 8.29 (d, 2H), 8.18-8.16 (d, 2H), 8.12 (s, 1H), 7.9 (d, 2H), 7.84-7.82 (m, 2H), 7.53-7.51 (m, 2H), 7.44-7.41 (m, 4H), 1.62 (s, 12H)

Preparation Example 3

Preparation of Compound C

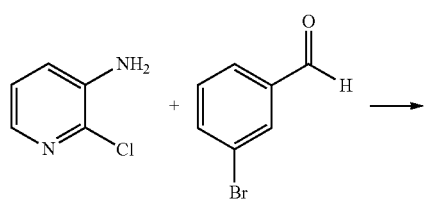

Preparation of Compound C-1

Dichloromethane (31 mL) and 3-bromobenzoyl chloride (25 g, 0.1139 mol) were mixed and stirred at −10° C. After 3-bromobenzoyl chloride was completely dissolved, a mixing solution of pyridine (106 mL) and 2-chloropyridine-3-amine (13.2 g, 0.1026 mol) was slowly dropped thereinto and stirred. After 2 hours 30 minutes, water (1250 mL) was added thereto, and the prepared solid compound was filtered and washed with methanol. The resultant material was dried, thereby obtaining Compound C-1 (28.0 g, 87%) as a white solid.

$^1$H NMR (CDCl$_3$) δ 8.58 (m, 1H), 8.31 (d, 1H), 8.30 (t, 1H), 8.14 (m, 1H), 7.90 (m, 1H), 7.45 (q, 1H), 7.40 (t, 1H)

Preparation of Compound C-2

1,3-dimethyl-3,4,5,6-tetrahydro-2(1H)-pyrimidinone (DMPU, 110 mL), Compound C-1 (27 g, 0.0866 mol), and Lawesson's reagent (35.1 g) were mixed and stirred under reflux. After 2 hours 30 minutes, the mixture was extracted with ethyl acetate (EA) and concentrated, thereby obtaining Compound C-2 (20 g, 80%) as a light yellow solid.

$^1$H NMR (CDCl$_3$) δ 8.62-8.60 (d, 1H), 8.33 (d, 1H), 8.30 (t, 1H), 8.03-8.00 (d, 1H), 7.68-7.65 (d, 1H), 7.50-7.46 (q, 1H), 7.41 (t, 1H)

Preparation of Compound C

Compound C-2 (27.47 g, 103 mmol), bis(pinacolato)diboron (27.47 g, 108 mmol), 1,4-dioxane (450 mL), 1,1'-bis(diphenylphosphino)ferrocene-palladium(II)dichloride dichloromethane complex (1.68 g, 2.1 mmol), and potassium acetate (20.22 g, 206.1 mmol) were mixed and stirred under reflux for 12 hours. Then, the mixture was cooled to room temperature. An organic layer was extracted by adding saturated sodium chloride (NaCl) aqueous solution and ethyl acetate (EA) to the reactant, dried over magnesium sulfate (MgSO₄), and treated with activated charcoal, followed by filtering with celite. After a solid prepared by concentrating the filtrate under reduced pressure was suspended and stirred in hexane, the suspension was filtered again and washed with hexane, thereby obtaining Compound C (41.8 g, 89%).

¹H NMR (CDCl₃) δ 8.60-8.58 (d, 1H), 8.50 (s, 1H), 8.32-8.30 (d, 1H), 8.25-8.22 (d, 1H), 7.99-7.97 (d, 1H), 7.55 (t, 1H), 7.48-7.44 (q, 1H), 1.40 (s, 12H)

Preparation Example 4

Preparation of Compound D

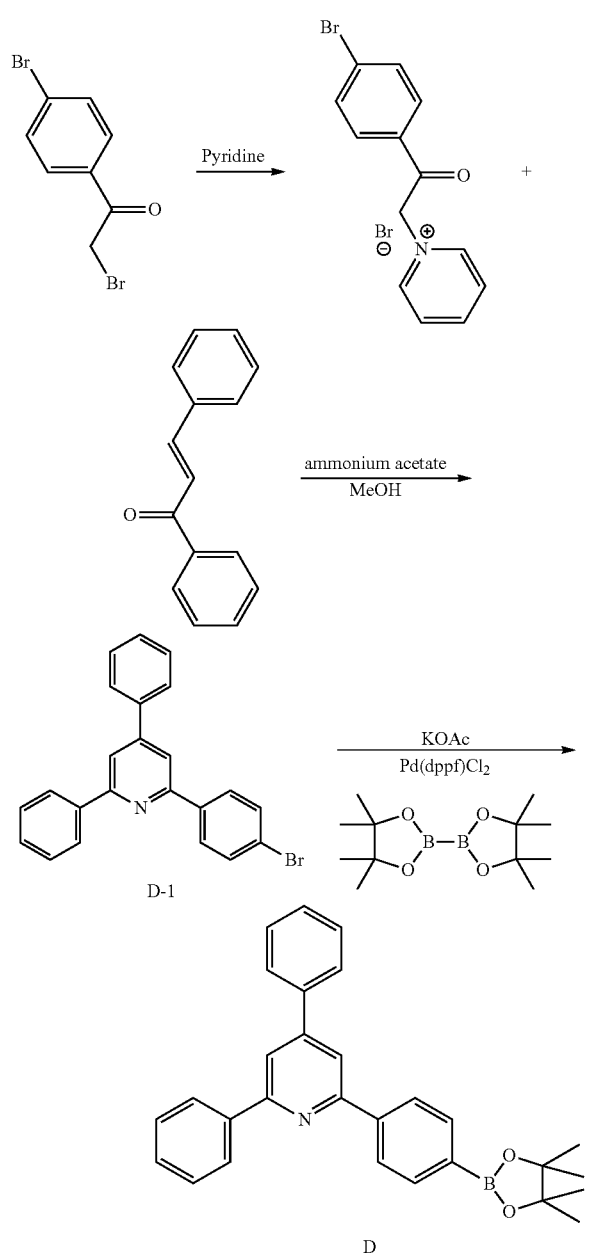

Preparation of Compound D-1

4-bromophenacyl bromide (100 g, 360 mmol) was slowly added to pyridine (1000 mL) while stirring pyridine (1000 mL). After the mixture was stirred at room temperature for 2 hours, the precipitated solid was separated by filtering under reduced pressure and washed with methanol. The prepared compound (120 g, 336 mmol), trans-Chalcone (35 g, 168 mmol), ammonium acetate (25.9 g, 336 mmol), and methanol (450 mL) were mixed and stirred under reflux for 12 hours. When the reaction was completed, the reactant was cooled to room temperature. Then, the precipitated solid was separated by filtering under reduced pressure and washed with methanol, thereby obtaining Compound D-1 (25.5 g, 47%) as a white solid.

¹H NMR (CDCl₃) δ 7.46-7.58 (m, 6H), 7.65 (d, 2H), 7.76 (d, 2H), 7.78 (d, 2H), 8.12 (d, 2H), 8.22 (d, 2H)

Preparation of Compound D

Compound D-1 (25 g, 64.7 mmol), bis(pinacolato)diboron, (19.7 g, 77.6 mmol), 1,4-dioxane (600 mL), 1,1'-bis(diphenylphosphino)ferrocene-palladium(II)dichloride dichloromethane complex (1.6 g, 1.9 mmol), and potassium acetate (12.7 g, 129 mmol) were mixed and stirred under reflux for 12 hours. When the reaction was completed, the reactant was cooled to room temperature. Then, the precipitated solid was filtered under reduced pressure and separated using a silica gel column (hexane:ethyl acetate=10:1), thereby obtaining Compound D (21.6 g, 77%) as a white solid.

¹H NMR (CDCl₃) δ 1.41 (s, 12H), 7.47-7.58 (m, 6H), 7.77 (d, 2H), 7.92-7.99 (m, 4H), 8.21-8.25 (m, 4H)

Preparation Example 5

Preparation of Compound E

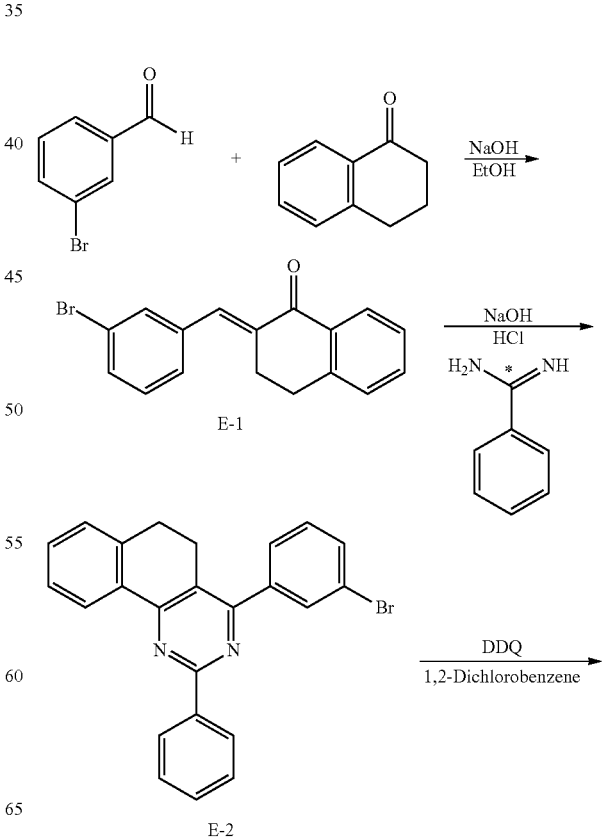

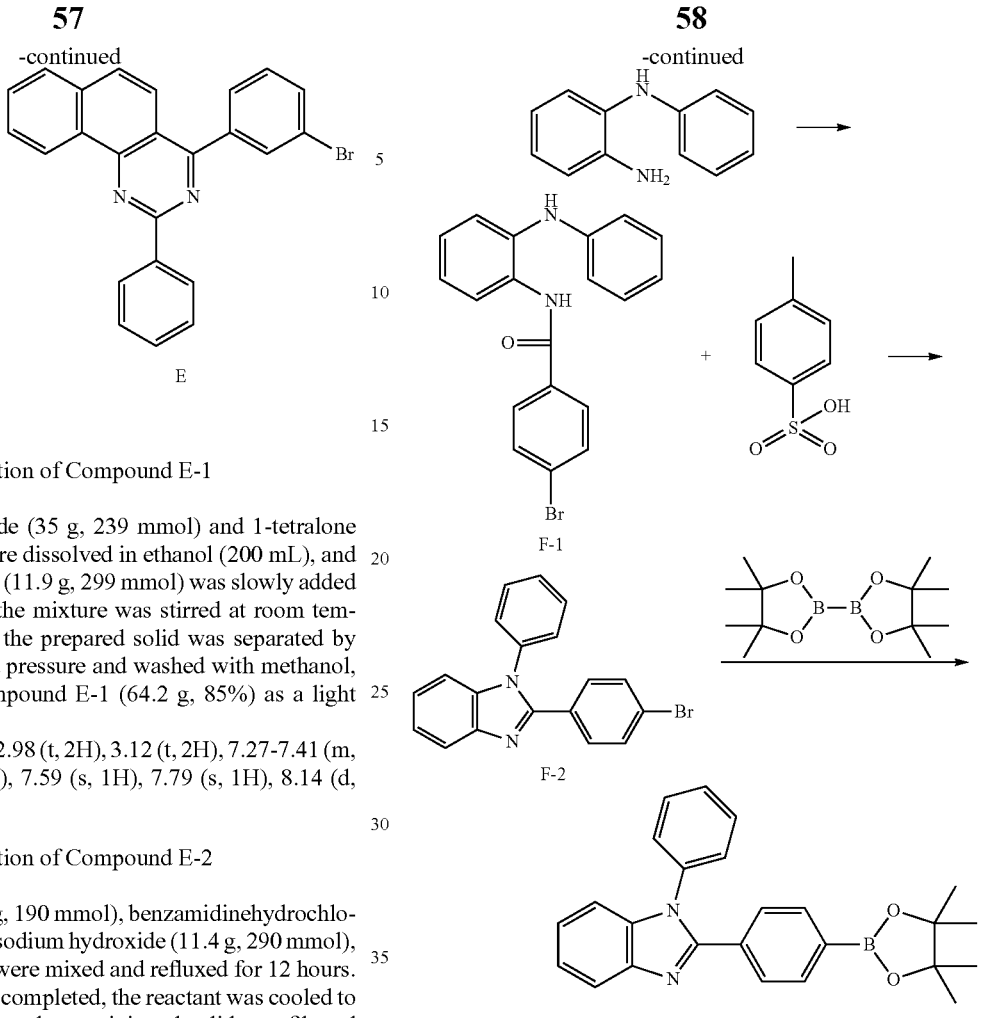

Preparation of Compound E-1

3-bromobenzaldehyde (35 g, 239 mmol) and 1-tetralone (46.6 g, 252 mmol) were dissolved in ethanol (200 mL), and then sodium hydroxide (11.9 g, 299 mmol) was slowly added thereto at 0° C. After the mixture was stirred at room temperature for 12 hours, the prepared solid was separated by filtering under reduced pressure and washed with methanol, thereby obtaining Compound E-1 (64.2 g, 85%) as a light yellow solid.

$^1$H NMR (CDCl$_3$) δ 2.98 (t, 2H), 3.12 (t, 2H), 7.27-7.41 (m, 4H), 7.49-7.54 (m, 2H), 7.59 (s, 1H), 7.79 (s, 1H), 8.14 (d, 1H)

Preparation of Compound E-2

Compound E-1 (60 g, 190 mmol), benzamidinehydrochloride (33 g, 210 mmol), sodium hydroxide (11.4 g, 290 mmol), and ethanol (600 mL) were mixed and refluxed for 12 hours. When the reaction was completed, the reactant was cooled to room temperature. Then, the precipitated solid was filtered under reduced pressure and separated using a silica gel column (hexane:methylene chloride=1:1), thereby obtaining Compound E-2 (54.4 g, 68%) as a light yellow solid.

$^1$H NMR (CDCl$_3$) δ 2.87 (t, 2H), 3.02 (t, 2H), 7.24 (s, 1H), 7.34-7.61 (m, 7H), 7.87 (s, 2H), 8.56-8.63 (m, 3H)

Preparation of Compound E

Compound E-2 (62.7 g, 151 mmol), DDQ (34 g, 151 mmol), and 1,2-dichlorobenzene (600 mL) were mixed and refluxed at 120° C. for 12 hours. When the reaction was completed, the reactant was cooled to room temperature and extracted with water and methylene chloride, followed by separation using a silica gel column (hexane:methylene chloride=1:1), thereby obtaining Compound E (22.42 g, 36%) as a light yellow solid.

$^1$H NMR (CDCl$_3$) δ 7.47-7.59 (m, 4H), 7.72-8.07 (m, 8H), 8.82 (d, 2H), 9.54 (m, 1H)

Preparation Example 6

Preparation of Compound F

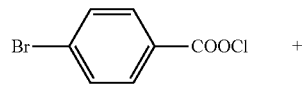

Preparation of Compound F-1

N1-phenylbenzene-1,2-diamine (48 g, 260 mmol) was completely dissolved in N,N-Dimethyl acetamide (DMAC, 100 mL) at 0° C., and then 4-bromobenzoyl chloride (63 g, 287 mmol) was dropped thereinto and stirred. After 2 hours 30 minutes, pyridine (60 mL) and water (100 mL) were added thereto. After stirring the mixture for 30 minutes, the prepared solid was filtered while being washed with methanol, thereby obtaining Compound F-1 (95 g, 95%) as a white solid.

Preparation of Compound F-2

Compound F-1 (50 g, 136 mmol), p-toluene sulfonic acid (PTSA, 46.9 g, 272 mmol), and toluene (500 mL) were mixed and stirred under reflux with a Dean-stark trap under nitrogen atmosphere. After 2 hours, the reactant was cooled to room temperature, and an organic layer was extracted by adding saturated sodium chloride aqueous solution and ethyl acetate, dried over magnesium sulfate, and then treated with activated charcoal, followed by filtering with celite. A solid obtained by concentrating the filtrate under reduced pressure was re-crystallized, thereby obtaining Compound F-2 (39 g, 81%).

$^1$H NMR (CDCl$_3$) δ 8.24 (d, 1H), 7.66 (m, 3H), 7.62-7.46 (m, 6H), 7.40 (m, 2H), 7.32 (d, 2H)

Preparation of Compound F

Compound F-2 (38.6 g, 110 mmol), potassium acetate (32.4 g, 330 mmol), bis(pinacolato)diboron (36.5 g, 143 mmol), 1,4-dioxane (390 mL), and PdCl$_2$(dppf) (1.8 g, 2 mmol) were mixed and stirred at 80° C. for 18 hours, and then cooled at room temperature. Water (400 mL) was added to the reactant and stirred. After stirring, an organic layer was extracted by adding saturated sodium chloride aqueous solution and ethyl acetate, dried over magnesium sulfate, and treated with activated charcoal, followed by filtering with celite. A solid prepared by concentrating the filtrate under reduced pressure was re-crystallized, thereby obtaining Compound F (36 g, 82%).

$^1$H NMR (CDCl$_3$) δ 7.92 (d, 1H), 7.76 (d, 2H), 7.59 (d, 2H), 7.56-7.45 (m, 3H), 7.41-7.29 (m, 4H), 7.27 (s, 1H), 1.35 (s, 12H)

Preparation Example 7

Preparation of Compound G

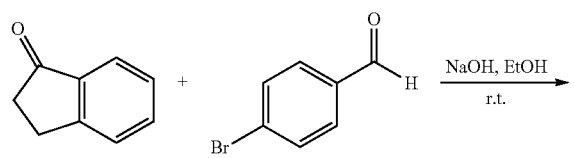

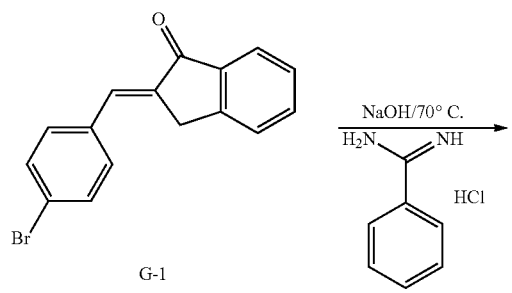

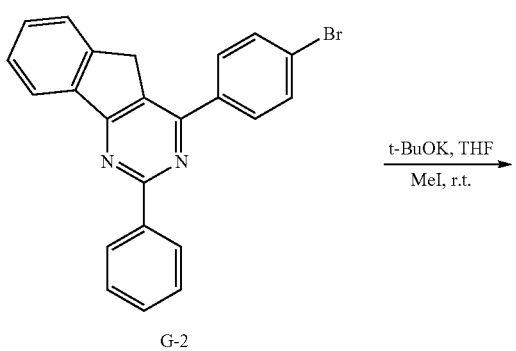

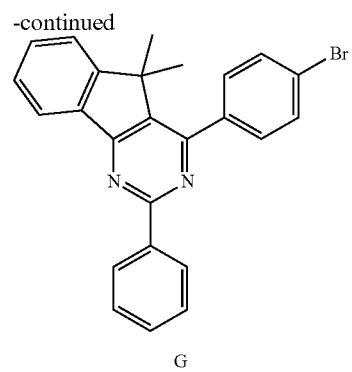

G

Preparation of Compound G-1

1-indanone (80 g, 0.61 mol) and 4-bromobenzaldehyde (117.8 g, 0.64 mol) were dissolved in ethanol (1280 mL), and then sodium hydroxide (30.3 g, 0.76 mol) was slowly added thereto at 0° C. After the mixture was stirred at room temperature for 3 hours, the prepared solid was separated by filtering under reduced pressure and sequentially washed with methanol, distilled water, and methanol. The resultant material was dried, thereby obtaining Compound G-1 (130 g, 71.8%) as a yellow solid.

$^1$H NMR (CDCl$_3$) δ 7.97 (1H, d), 7.67-7.54 (7H, m), 7.46 (1H, t), 3.32 (2H, d)

Preparation of Compound G-2

Compound G-1 (60 g, 0.20 mol), benzamidinehydrochloride (94.2 g, 0.60 mol), sodium hydroxide (24.1 g, 0.60 mol), and ethanol (1200 mL) were mixed and refluxed for 12 hours. When the reaction was completed, the reactant was cooled to room temperature, and the precipitated solid was filtered under reduced pressure and washed with water and ethanol. The resultant material was dried, thereby obtaining Compound G-2 (43 g, 53.7%) as a yellow solid.

$^1$H NMR (CDCl$_3$) δ 8.65 (3H, m), 7.70 (4H, q), 7.51 (5H, m), 7.28 (1H, s), 3.40 (2H, d)

Preparation of Compound G

Compound G-2 (50 g, 0.13 mol), potassium tertiary butoxide (t-BuOK, 29.5 g, 0.26 mol), and tetrahydrofuran (THF, 750 mL) were mixed and stirred at 0° C. until the mixture was completely dissolved. Then, methyliodide (MeI, 44.4 g, 0.31 mol) was slowly added thereto. When the reaction was completed after stirring at room temperature for 4 hours, water is added thereto. Then, the resultant was extracted with MC and dried over anhydrous magnesium sulfate, followed by filtration and concentration under reduce pressure, thereby obtaining Compound G (24 g, 44.9%) as a white solid.

$^1$H NMR (CDCl$_3$) δ 8.65 (3H, m), 7.70 (4H, q), 7.51 (5H, m), 7.28 (1H, s), 3.40 (2H, d), 1.67 (6H, s)

Preparation Example 8

Preparation of Compound H

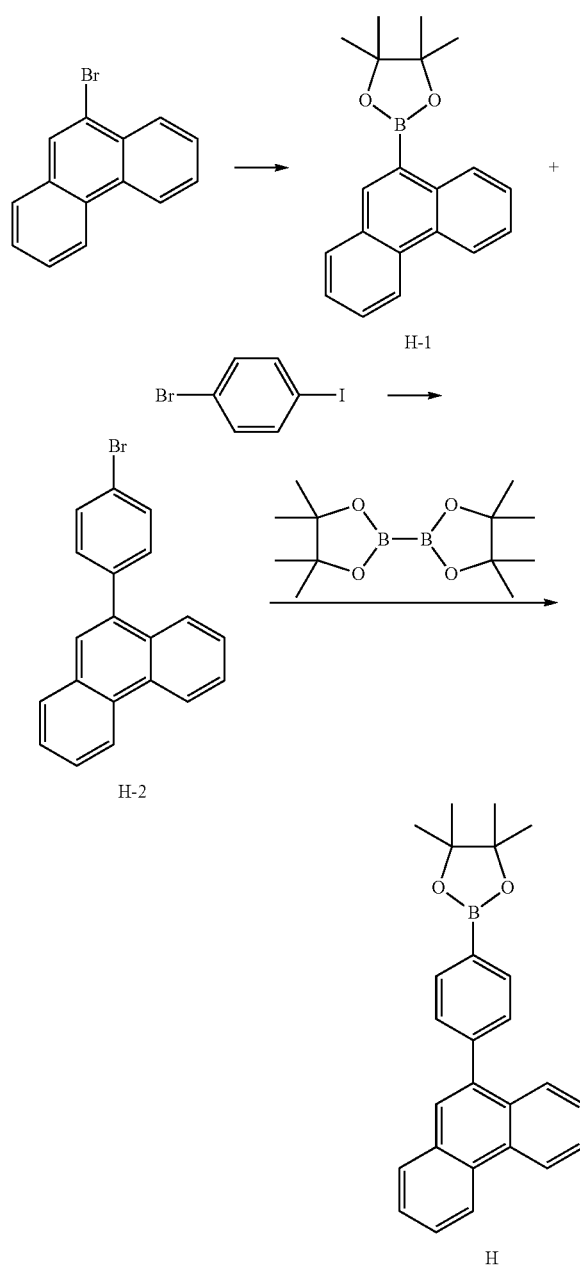

Preparation of Compound H-1

9-bromophenanthrene (67.2 g, 0.26 mol), bis(pinacolato)diboron, (69.68 g, 0.27 mol), 1,4-dioxane (1350 mL), 1,1'-bis(diphenylphosphino)ferrocene-palladium(II)dichloride dichloromethane complex (3.82 g, 5.23 mmol), and potassium acetate (51.3 g, 0.52 mol) were mixed and stirred under reflux. After 12 hours, the reactant was cooled to room temperature, and an organic layer was extracted by adding saturated sodium chloride aqueous solution and ethylacetate, dried over anhydrous magnesium sulfate, and then treated with activated charcoal, followed by filtering with celite. After a solid prepared by concentrating the filtrate under reduced pressure was suspended in hexane, the suspension was filtered again and washed with hexane, thereby obtaining Compound H-1 (69.2 g, 69.2%) as a solid.

$^1$H NMR (CDCl$_3$) δ 8.89 (d, 1H), 8.86 (d, 1H), 8.11-7.78 (m, 7H), 1.40 (s, 12H)

Preparation of Compound H-2

Compound H-1 (64.5 g, 0.21 mol), 1-bromo-4-iodobenzene (60.0 g, 0.21 mol), Pd(PPh$_3$)$_4$ (4.9 g, 4.2 mmol), 2M K$_2$CO$_3$ aqueous solution (300 mL), and THF (600 mL) were mixed and stirred under reflux for 24 hours. After an organic layer was extracted with MC, the extracted organic layer was concentrated under reduced pressure and washed with acetone, thereby obtaining Compound H-2 (60.1 g, 84.9%).

$^1$H NMR (CDCl$_3$) δ 8.89 (d, 1H), 8.86 (d, 1H), 8.11-7.78 (m, 11H)

Preparation of the compound H

Compound H-2 (60.0 g, 0.18 mol), bis(pinacolato)diboron, (48.0 g, 0.19 mol), 1,4-dioxane (1200 mL), 1,1'-bis(diphenylphosphino)ferrocene-palladium(II)dichloride dichloromethane complex (2.64 g, 3.60 mmol), and potassium acetate (35.4 g, 0.36 mol) were mixed and stirred under reflux. After 12 hours, the reactant was cooled to room temperature, and an organic layer was extracted by adding saturated sodium chloride aqueous solution and ethylacetate, dried over magnesium sulfate, and then treated with activated charcoal, followed by filtering with celite. After a solid prepared by concentrating the filtrate under reduced pressure was suspended in hexane, the suspension was filtered again and washed with hexane, thereby obtaining Compound H (32.0 g, 46.7%) as a solid.

$^1$H NMR (CDCl$_3$) δ 8.89 (d, 1H), 8.86 (d, 1H), 8.11-7.78 (m, 11H), 1.40 (s, 12H)

Preparation Example 9

Preparation of Compound I

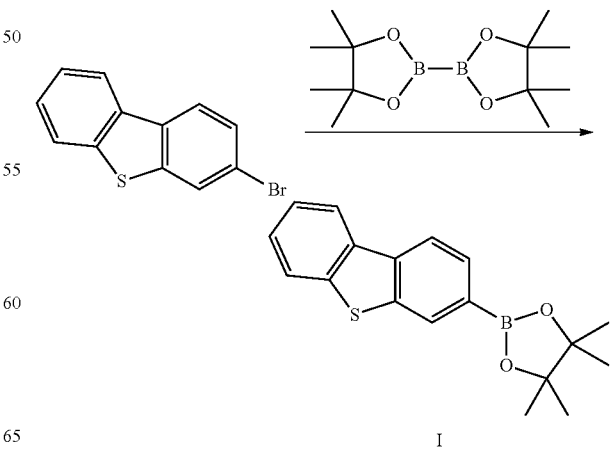

2-bromodibenzothiophene (50 g, 190 mmol), bis(pinacolato)diboron, (50.7 g, 199.5 mmol), 1,4-dioxane (1000 mL), 1,1'-bis(diphenylphosphino)ferrocene-palladium(II)dichloride dichloromethane complex (2.78 g, 3.8 mmol), and potassium acetate (37.3 g, 380 mmol) were mixed and stirred under reflux. After 12 hours, the reactant was cooled to room temperature, and an organic layer was extracted by adding saturated sodium chloride aqueous solution and ethylacetate, dried over anhydrous magnesium sulfate, and then treated with activated charcoal, followed by filtering with celite. The filtrate was concentrated under reduced pressure, thereby obtaining Compound I (23 g, 39%).

$^1$H NMR (CDCl$_3$) δ 7.88 (m, 4H), 7.32 (m, 3H), 1.40 (s, 12H)

Preparation Example 10

Preparation of Compound J

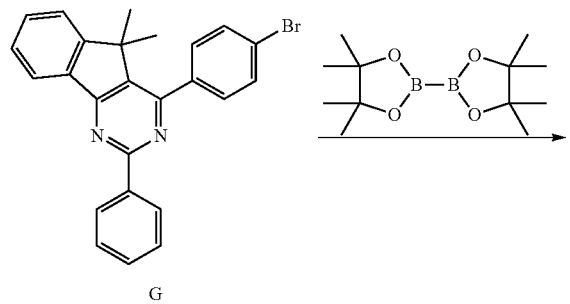

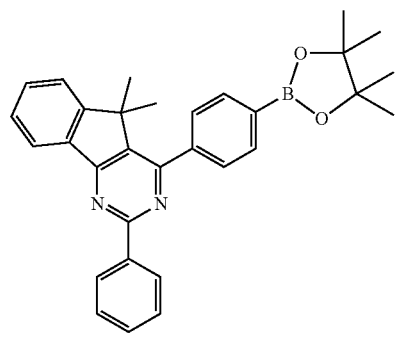

J

Compound G (10 g, 23.4 mmol), bis(pinacolato)diboron, (6.5 g, 25.5 mmol), 1,4-dioxane (200 mL), 1,1'-bis(diphenylphosphino)ferrocene-palladium(II)dichloride dichloromethane complex (0.2 g, 0.3 mmol), and potassium acetate (4.6 g, 46.8 mmol) were mixed and stirred under reflux. After 12 hours, the reactant was cooled to room temperature, and an organic layer was extracted by adding saturated sodium chloride aqueous solution and ethylacetate, dried over magnesium sulfate, and then treated with activated charcoal, followed by filtering with celite. After a solid prepared by concentrating the filtrate under reduced pressure was suspended in hexane, the suspension was filtered again and washed with hexane, thereby obtaining Compound J (9.8 g, 87.9%) as a yellow solid.

$^1$H NMR (CDCl$_3$) δ 8.62 (3H, m), 7.68 (4H, q), 7.55 (5H, m), 7.12 (1H, s), 1.40 (s, 12H)

Preparation Example 11

Preparation of Compound K

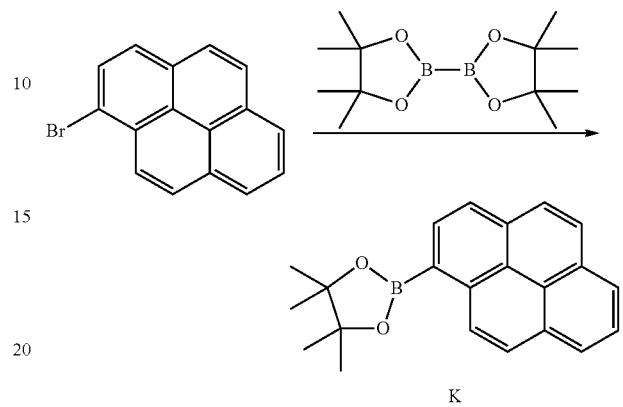

K 1-bromopyrene (40 g, 142 mmol), bis(pinacolato)diboron, (39.74 g, 157 mmol), 1,4-dioxane (480 mL), 1,1'-bis(diphenylphosphino)ferrocene-palladium(II)dichloride dichloromethane complex (1.16 g, 1.4 mmol), and potassium acetate (27.93 g, 284 mmol) were mixed and stirred under reflux. After 9 hours, the reactant was cooled to room temperature, and an organic layer was extracted by adding saturated sodium chloride aqueous solution and ethylacetate, dried over magnesium sulfate, and then treated with activated charcoal, followed by filtering with celite. A solid prepared by concentrating the filtrate under reduced pressure was re-crystallized in ethylacetate, thereby obtaining Compound K (34.09 g, 73%).

$^1$H NMR (CDCl$_3$) δ 8.12-8.1 (d, 2H), 7.93-7.70 (m, 5H), 7.71 (d, 2H), 1.26 (q, 12H)

Preparation Example 12

Preparation of Compound L

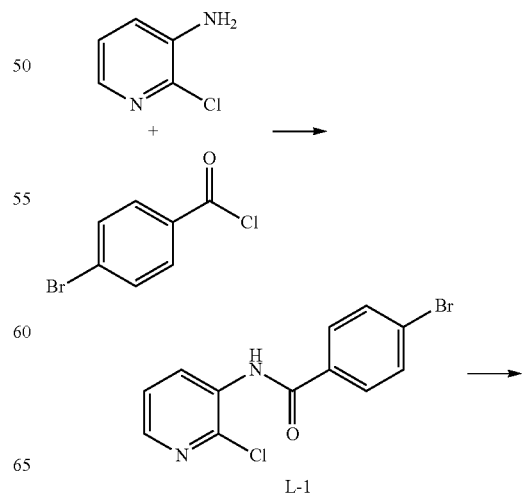

L-1

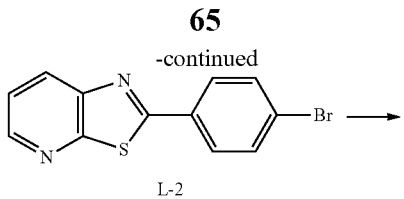

L-2

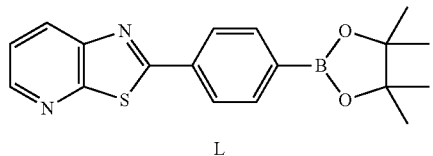

L

Preparation of Compound L-1

Dichloromethane (31 mL) and 4-bromobenzoyl chloride (25 g, 0.1139 mol) were mixed and stirred at −10° C. After 4-bromobenzoyl chloride was completely dissolved, a mixing solution of pyridine (106 mL) and 2-chloropyridine-3-amine (13.2 g, 0.1026 mol) was slowly dropped thereinto and stirred. After 2 hours 30 minutes, water (1250 mL) was added thereto, and the prepared solid compound was filtered and washed with methanol. The resultant material was dried, thereby obtaining Compound L-1 (28.0 g, 87%) as a white solid.

$^1$H NMR (CDCl$_3$) δ 8.43 (d, 1H), 8.00 (s, 1H), 7.84-7.15 (d, 2H), 7.69-7.17 (m, 4H)

Preparation of Compound L-2

1,3-dimethyl-3,4,5,6-tetrahydro-2(1H)-pyrimidinone (DMPU, 100 mL), Compound L-1 (27 g, 0.0866 mol), and Lawesson's reagent (35.1 g) were mixed and stirred under reflux. After 2 hours 30 minutes, an organic layer was extracted with ethylacetate (EA) and dried over magnesium sulfate, followed by filtering. Then, a solid prepared by concentrating the filtrate under reduced pressure was washed with methanol, thereby obtaining Compound L-2 (20 g, 80%).

$^1$H NMR (CDCl$_3$) δ 8.59 (d, 1H), 7.75 (d, 1H), 7.49-7.26 (d, 2H), 7.38-7.15 (m, 3H)

Preparation of the compound L

Compound L-2 (27.47 g, 103 mmol), bis(pinacolato)diboron, (27.47 g, 108 mmol), 1,4-dioxane (450 mL), 1,1'-bis(diphenylphosphino)ferrocene-palladium(II)dichloride dichloromethane complex (1.68 g, 2.1 mmol), and potassium acetate (20.22 g, 206.1 mmol) were mixed and stirred under reflux for 12 hours. Then, the mixture was cooled to room temperature. An organic layer was extracted by adding saturated sodium chloride (NaCl) aqueous solution and ethylacetate (EA) to the reactant, dried over magnesium sulfate (MgSO$_4$), and treated with activated charcoal, followed by filtering with celite. After a solid prepared by concentrating the filtrate under reduced pressure was suspended and stirred in hexane, the suspension was filtered again and washed with hexane, thereby obtaining Compound L (41.8 g, 89%).

$^1$H NMR (CDCl$_3$) δ 8.59 (d, 1H), 7.75 (d, 1H), 7.50-7.22 (m, 2H), 7.38-7.06 (m, 3H), 1.26 (s, 12H)

Preparation Example 13

Preparation of Compound M

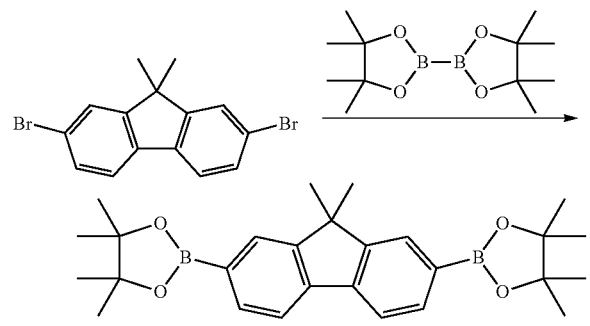

M 2.7-dibromo-9,9-dimethyl-9H-fluorene (25 g, 71.0 mmol), bis(pinacolato)diboron, (37.87 g, 149 mmol), 1,4-dioxane (300 mL), 1,1'-bis(diphenylphosphino)ferrocene-palladium (II)dichloride dichloromethane complex (0.58 g, 0.7 mmol), and potassium acetate (13.94 g, 142 mmol) were mixed and stirred under reflux. After 9 hours, the reactant was cooled to room temperature, and an organic layer was extracted by adding saturated sodium chloride aqueous solution and ethylacetate, dried over magnesium sulfate, and then treated with activated charcoal, followed by filtering with celite. A solid prepared by concentrating the filtrate under reduced pressure was re-crystallized in ethylacetate, thereby obtaining Compound M (30.9 g, 61%).

$^1$H NMR (CDCl$_3$) δ 7.80 (m, 2H), 7.60 (m, 2H), 7.40 (m, 2H), 1.67-0.86 (s, 6H), 1.26 (s, 24H)

Preparation Example 14

Preparation of Compound N

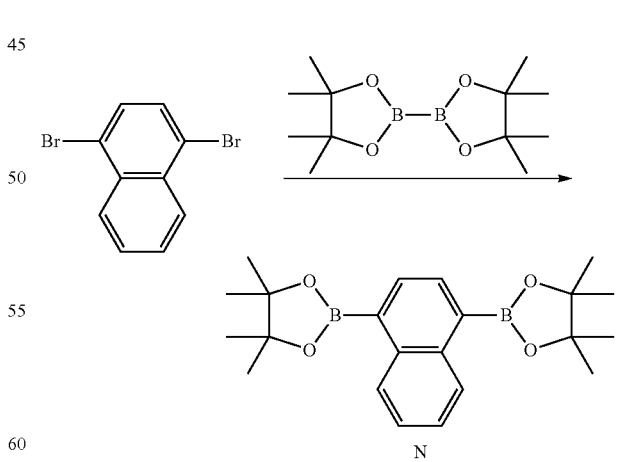

N 1,4-dibromonaphthalene (25 g, 87.4 mmol), bis(pinacolato)diboron, (46.62 g, 184 mmol), 1,4-dioxane (300 mL), 1,1'-bis(diphenylphosphino)ferrocene-palladium(II)dichloride dichloromethane complex (0.71 g, 0.9 mmol), and potassium acetate (17.16 g, 174.8 mmol) were mixed and stirred under reflux. After 9 hours, the reactant was cooled to room temperature, and an organic layer was extracted by adding saturated sodium chloride aqueous solution and ethylacetate, dried over magnesium sulfate, and then treated with activated charcoal, followed by filtering with celite. A solid prepared by concentrating the filtrate under reduced pressure was re-crystallized in ethylacetate, thereby obtaining Compound N (21.93 g, 66%).

$^1$H NMR (CDCl$_3$) δ 7.70-7.67 (m, 2H), 7.30-7.32 (m, 4H), 1.26 (s, 30H)

Example 1

Preparation of Compound 100

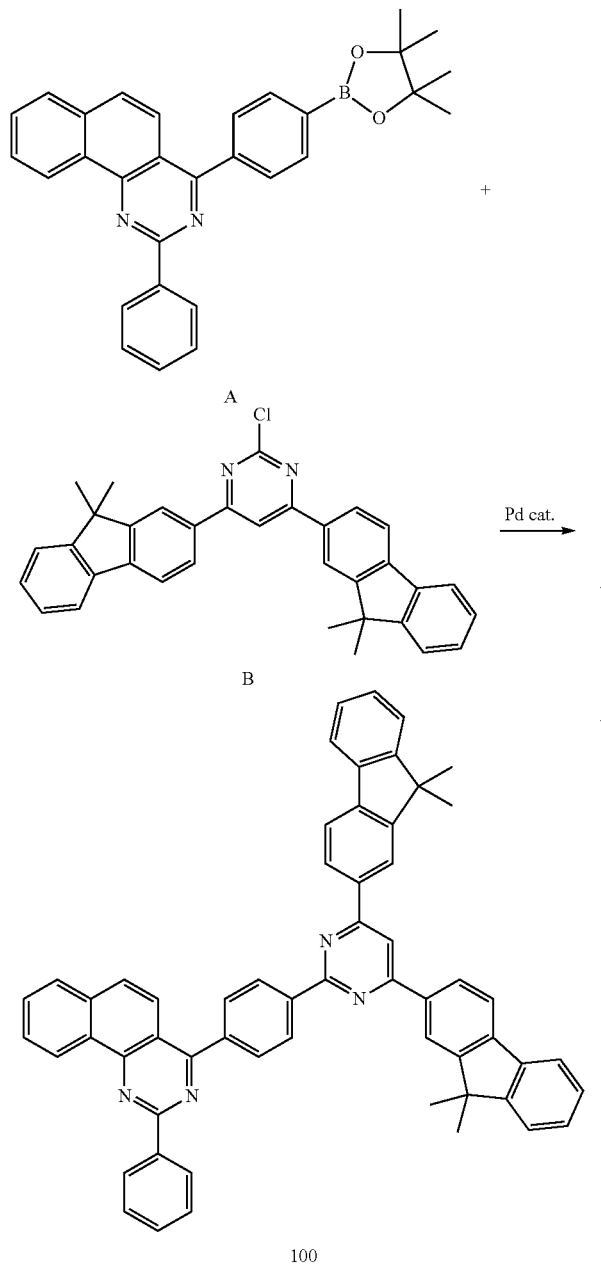

100

Preparation of Compound 100

Compound A (Preparation Example 1, 9.8 g, 23.83 mmol), Compound B (Preparation Example 2, 12.0 g, 24.1 mmol), Pd(PPh$_3$)$_4$ (0.55 g, 0.48 mmol), K$_2$CO$_3$ (6.59 g, 47.65 mmol), distilled water (49 mL), and THF (98 mL) were mixed and stirred under reflux for 12 hours. When the reaction was completed, the reactant was cooled to room temperature, and the prepared solid was washed with water and methanol, thereby obtaining Compound 100 (12.1 g, 63.4%).

$^1$H NMR (CDCl$_3$) δ 9.61 (t, 1H), 9.05 (d, 2H), 8.94 (d, 2H), 8.47 (s, 2H), 8.38 (dd, 2H), 8.20 (d, 3H), 8.15 (d, 1H), 7.98 (d, 3H), 7.86 (m, 5H), 7.59 (m, 5H), 7.44 (t, 4H), 1.68 (12H)

MALDI-TOF MS: m/z 694.98, cal. 695.61

Example 2

Preparation of Compound 98

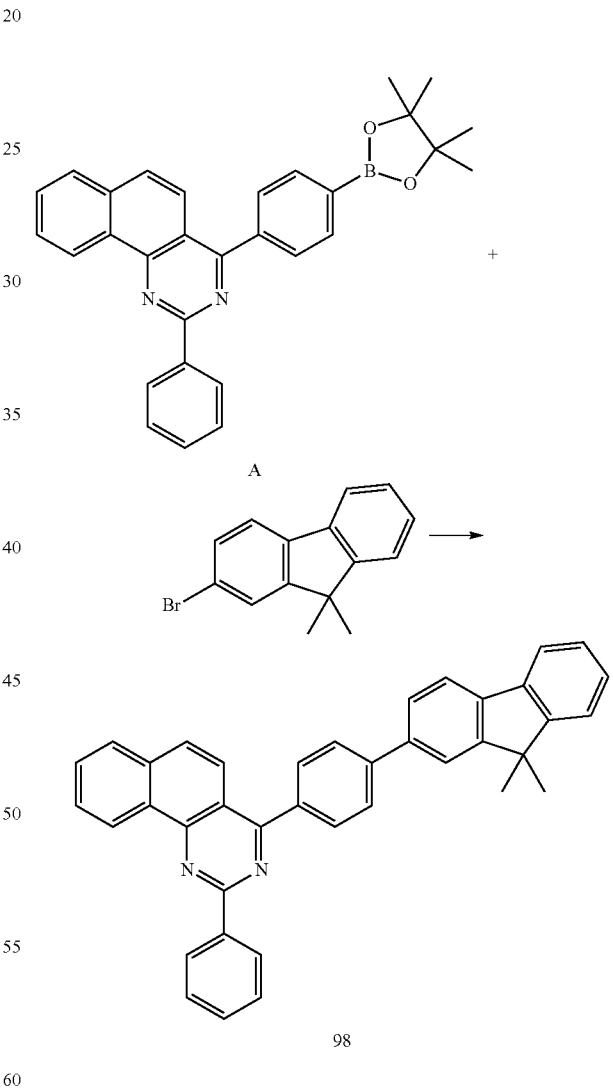

98

2-bromo-9,9-dimethyl-9H-fluorene (9 g, 32.9 mmol), Compound A (Preparation Example 1, 15.10 g, 32.9 mmol), THF (135 mL), Pd(PPh$_3$)$_4$ (0.38 g, 0.3 mmol), and 1M potassium carbonate aqueous solution (68 mL) were mixed and stirred under reflux. After reaction for 18 hours, the reactant was cooled to room temperature, and an organic layer was extracted by adding saturated sodium chloride aqueous solution and ethyl acetate, dried over magnesium sulfate, and treated with activated charcoal, followed by filtering with celite. A solid prepared by concentrating the filtrate under reduced pressure was re-crystallized, thereby obtaining Compound 98 (14.58 g, 84%).

$^1$H NMR (CDCl$_3$) δ 8.62 (3H, m), 7.78 (2H, d), 7.68 (6H, q), 7.60 (2H, m), 7.55 (5H, m), 7.42 (1H, s), 7.38 (3H, m), 1.58 (s, 6H)

MALDI-TOF MS: m/z 524.65, cal. 525.23

Example 3

Preparation of Compound 105

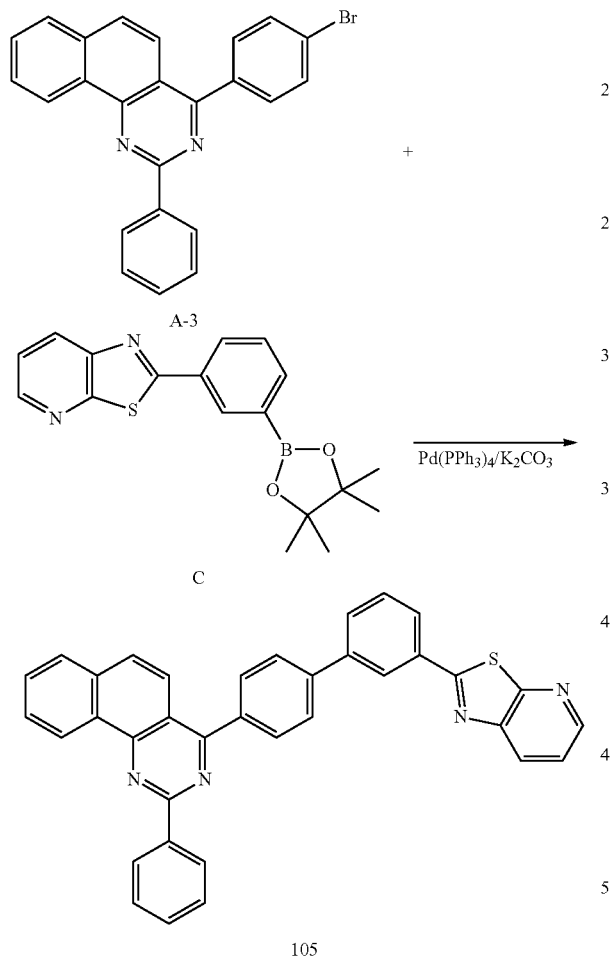

Compound A-3 (Preparation Example 1, 16.87 g, 36.8 mmol), Compound C (Preparation Example 3, 11.8 g, 40.5 mmol), THF (300 mL), Pd(PPh$_3$)$_4$ (0.85 g, 0.74 mmol), and 2M potassium carbonate aqueous solution (55 mL) were mixed and stirred under reflux. After reaction for 18 hours, the reactant was cooled to room temperature, and an organic layer was extracted by adding saturated sodium chloride aqueous solution and ethyl acetate, and dried over magnesium sulfate, followed by concentration under reduced pressure. After the solid obtained after concentration was input in ethyl acetate and suspended under heating, the suspension was filtered and washed with ethyl acetate, thereby obtaining Compound 105 (17.7 g, 89%).

$^1$H NMR (CDCl$_3$) δ 9.62 (d, 1H), 8.91 (d, 2H), 8.64 (d, 1H), 8.50 (s, 1H), 8.38 (d, 1H), 8.16 (d, 1H), 8.11-7.92 (m, 2H), 7.91 (d, 2H), 7.88-7.72 (m, 3H), 7.70 (t, 1H), 7.63-7.57 (m, 2H), 7.52 (dd, 1H)

MALDI-TOF MS: m/z 542.652 cal. 542.979

Example 4

Preparation of Compound 106

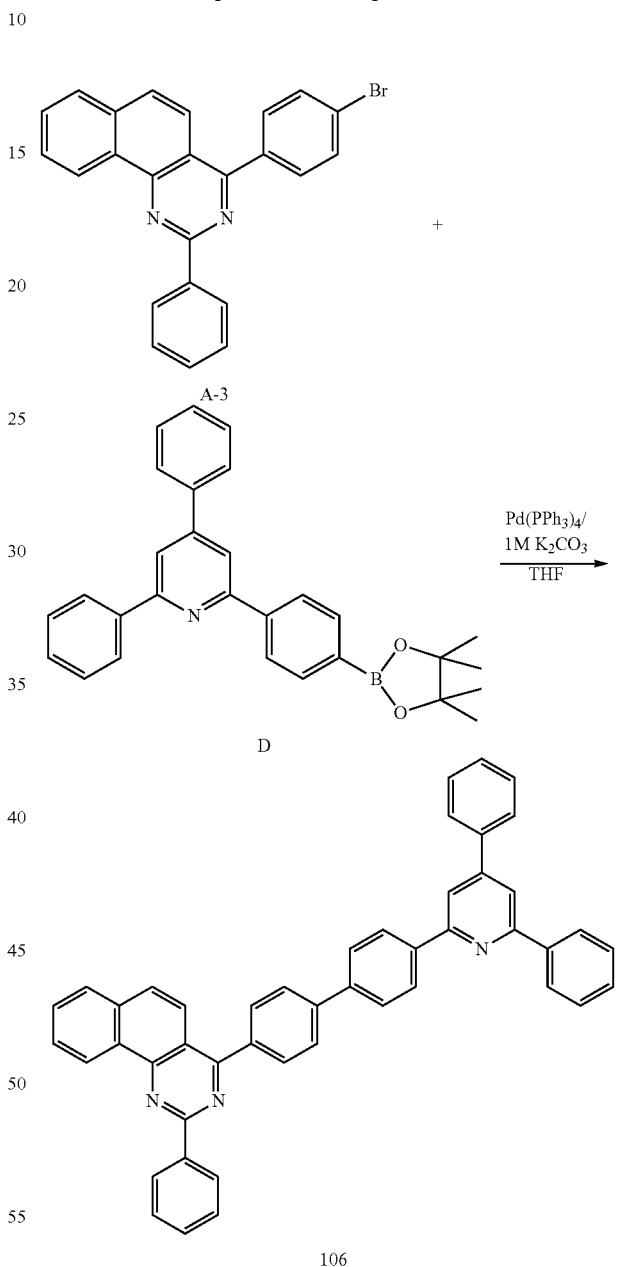

Compound A-3 (Preparation Example 1, 14 g, 34 mmol), Compound D (Preparation Example 4, 17.7 g, 41 mmol), Pd(PPh$_3$)$_4$ (0.4 g, 0.3 mmol), THF (150 mL), potassium carbonate (27.6 g, 199 mmol), and water (200 mL) were mixed and stirred under reflux. After reaction for 12 hours, the reactant was cooled to room temperature and extracted with methylene chloride, followed by concentration. The resultant material was recrystallized using methanol, thereby obtaining Compound 106 (16.4 g, 75%) as a white solid.

¹H NMR (CDCl₃) δ 7.50-7.61 (m, 9H), 7.80-7.98 (m, 12H), 8.08 (t, 3H), 8.26 (d, 2H), 8.38 (d, 2H), 8.89 (d, 2H), 9.58 (t, 1H)

MALDI-TOF MS: m/z 638.16, cal. 637.77

Example 5

Preparation of compound 113

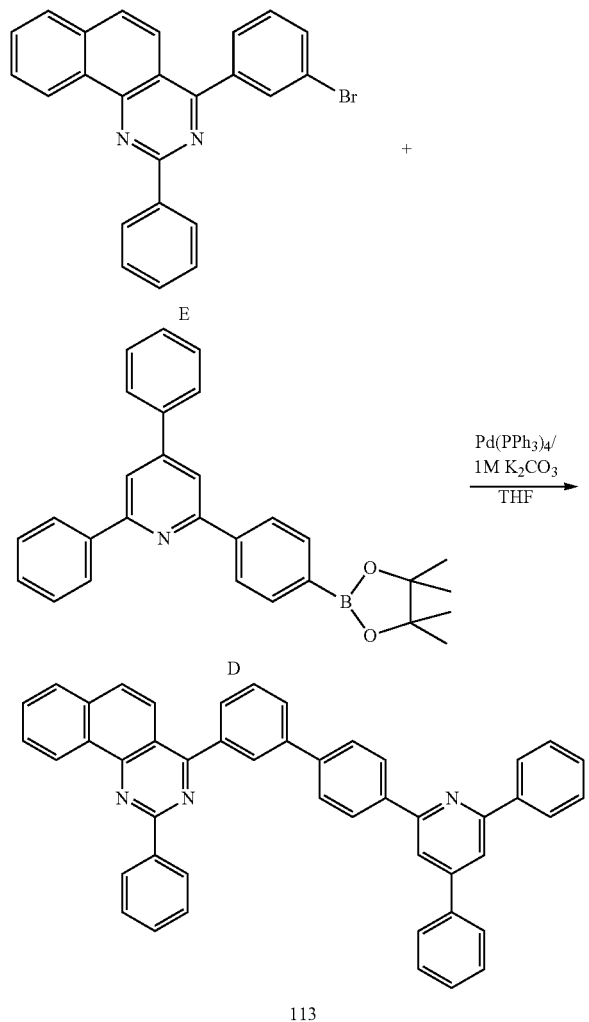

Compound E (Preparation Example 5, 8 g, 19 mmol), Compound D (Preparation Example 4, 10.11 g, 23 mmol), Pd(PPh₃)₄ (0.2 g, 0.19 mmol), THF (150 mL), potassium carbonate (13.8 g, 99 mmol), and water (100 mL) were mixed and stirred under reflux. After reaction for 12 hours, the reactant was cooled to room temperature and extracted with methylene chloride, followed by concentration. The resultant material was washed with hexane and ethyl acetate, thereby obtaining Compound 113 (8.6 g, 69%) as a light yellow solid.

¹H NMR (CDCl₃) δ 7.44-7.60 (m, 9H), 7.73-7.96 (m, 14H), 8.06 (d, 1H), 8.22 (d, 2H), 8.34 (d, 2H), 8.88 (d, 2H), 9.58 (t, 1H)

MALDI-TOF MS: m/z 638.07, cal. 637.77

Example 6

Preparation of Compound 110

Compound F (Preparation Example 6, 14.74 g, 37.2 mmol), Compound A-3 (Preparation Example 1, 15.3 g, 37.2 mmol), THF (230 mL), Pd(PPh₃)₄ (0.43 g, 0.4 mmol), and 1M potassium carbonate aqueous solution (115 mL) were mixed and stirred under reflux. After reaction for 18 hours, the reactant was cooled to room temperature, and an organic layer was extracted by adding saturated sodium chloride aqueous solution and dichloromethane, dried over magnesium sulfate, and treated with activated charcoal, followed by filtering with celite. A solid obtained by concentrating the filtrate under reduced pressure was re-crystallized, thereby obtaining Compound 110 (15.47 g, 69%).

¹H NMR (CDCl₃) δ 8.81 (d, 2H), 8.64 (d, 2H), 7.92 (d, 1H), 7.75 (d, 2H), 7.61 (d, 5H), 7.59-7.38 (m, 7H), 7.36-7.24 (m, 7H), 7.19 (s, 2H)

MALDI-TOF MS: m/z 601.32, cal. 600.71

Example 7

Preparation of Compound 118

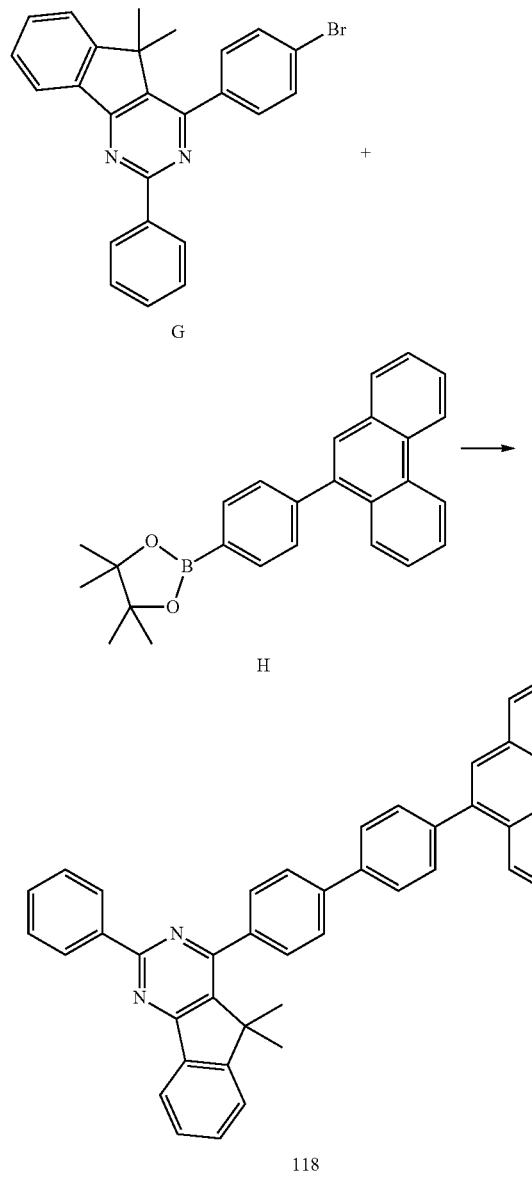

Compound G (Preparation Example 7, 10 g, 23.4 mmol), Compound H (Preparation Example 8, 8.9 g, 23.4 mmol), THF (150 mL), Pd(PPh$_3$)$_4$ (0.54 g, 0.47 mmol), K$_2$CO$_3$ (19.4 g, 140.4 mmol), and distilled water (75 mL) were mixed and stirred under reflux for 18 hours. When the reaction was completed, the reactant was cooled to room temperature. Then, the precipitated solid was filtered and washed with methanol. The prepared white solid was filtered with celite in toluene with heating. A solid prepared by concentrating the filtrate under reduced pressured was washed with methanol and suspended, followed by filtering, thereby obtaining Compound 118 (11.5 g, 81.8%).

$^1$H NMR (CDCl$_3$) δ 8.89 (d, 1H), 8.86 (d, 1H), 8.65 (3H, m), 8.11-7.78 (m, 11H), 7.70 (4H, q), 7.51 (5H, m), 7.28 (1H, s), 3.40 (2H, d)

MALDI-TOF MS: m/z 600.71, cal. 600.75

Example 8

Preparation of Compound 119

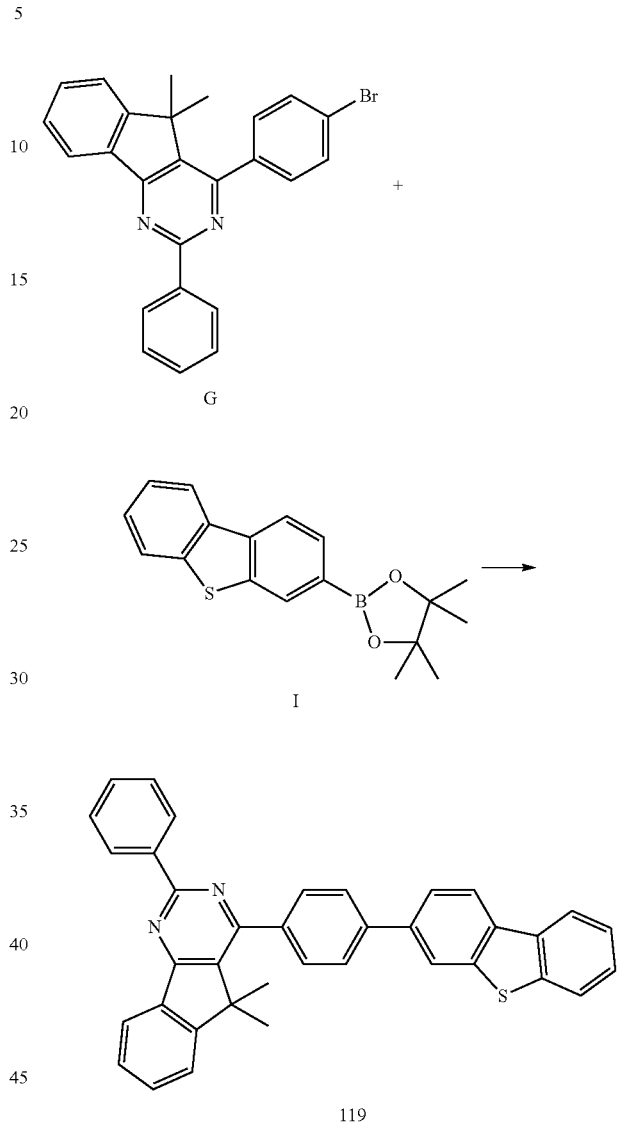

Compound G (Preparation Example 7, 10 g, 23.4 mmol), Compound I (Preparation Example 9, 8.9 g, 23.4 mmol), THF (150 mL), Pd(PPh$_3$)$_4$ (0.54 g, 0.47 mmol), K$_2$CO$_3$ (19.4 g, 140.4 mmol), and distilled water (75 mL) were mixed and stirred under reflux for 18 hours. When the reaction was completed, the reactant was cooled to room temperature. Then, the precipitated solid was filtered and washed with methanol. The prepared white solid was filtered with celite in toluene with heating. A solid prepared by concentrating the filtrate under reduced pressured was washed with methanol and suspended, followed by filtering, thereby obtaining Compound 119 (13 g, 91%).

$^1$H NMR (CDCl$_3$) δ 8.62 (3H, m), 7.88 (m, 4H), 7.68 (4H, q), 7.55 (5H, m), 7.32 (m, 3H), 7.12 (1H, s), 1.40 (s, 12H)

MALDI-TOF MS: m/z 310.18, cal. 310.22

Example 9

Preparation of Compound 120

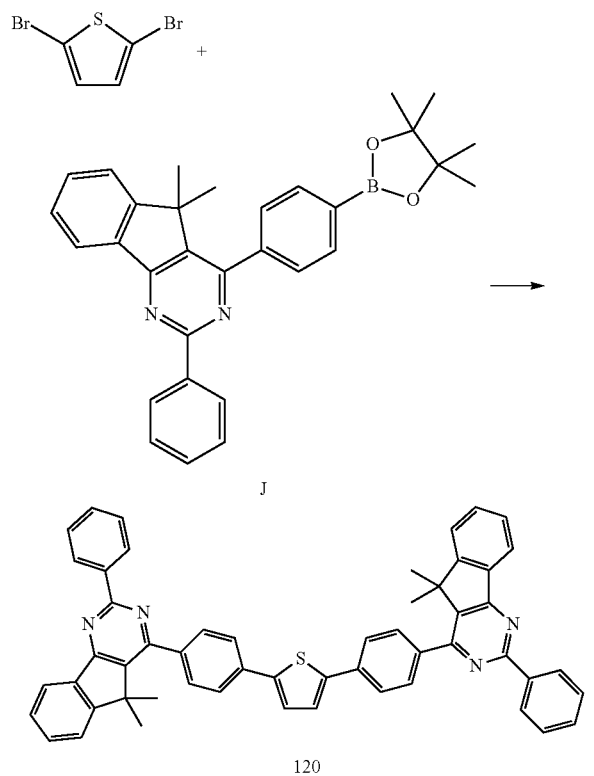

1,3-dibromothiophene (10 g, 41.3 mmol), Compound J (Preparation Example 10, 39.2 g, 82.7 mmol), THF (200 mL), Pd(PPh$_3$)$_4$ (1.91 g, 1.65 mmol), K$_2$CO$_3$ (68.6 g, 496 mmol), and distilled water (100 mL) were mixed and stirred under reflux for 18 hours. When the reaction was completed, the reactant was cooled to room temperature. Then, the precipitated solid was filtered and washed with methanol, thereby obtaining Compound 120 (22 g, 68.5%).

$^1$H NMR (CDCl$_3$) δ 8.62 (3H, m), 7.68 (4H, q), 7.55 (5H, m), 7.12 (1H, s), 6.64 (d, 1H)

MALDI-TOF MS: m/z 776.95, cal. 776.99

Example 10

Preparation of Compound 123

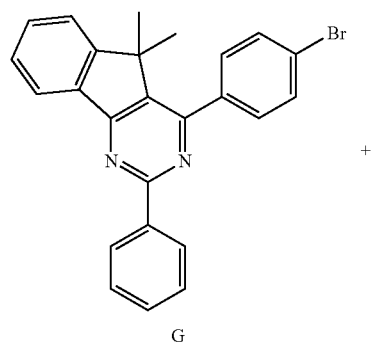

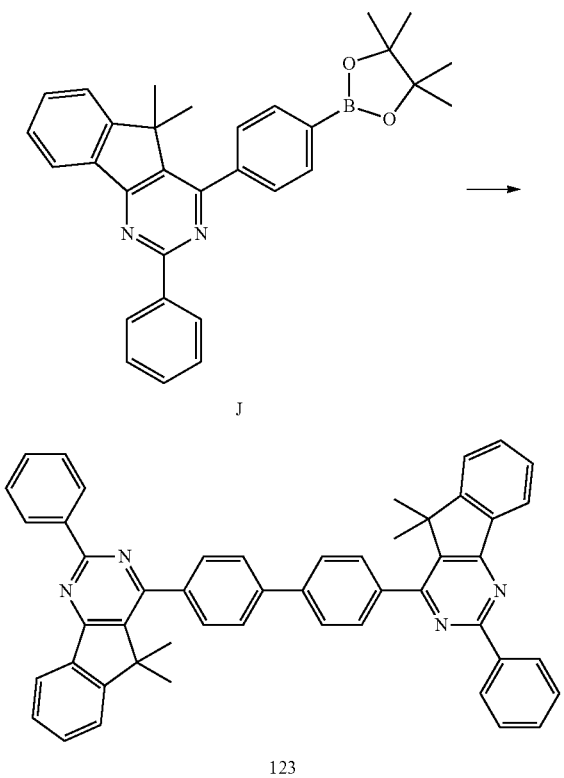

Compound G (Preparation Example 7, 15 g, 35.1 mmol), Compound J (Preparation Example 10, 16.65 g, 35.1 mmol), THF (250 mL), (PPh$_3$)$_4$ (0.81 g, 0.70 mmol), K$_2$CO$_3$ (29.11 g, 210.6 mmol), and distilled water (125 mL) were mixed and stirred under reflux for 18 hours. When the reaction was completed, the reactant was cooled to room temperature. Then, the precipitated solid was filtered and washed with methanol, thereby obtaining Compound 123 (21.7 g, 88.970).

$^1$H NMR (CDCl$_3$) δ 8.62 (3H, m), 7.68 (4H, q), 7.55 (5H, m), 7.12 (1H, s)

MALDI-TOF MS: m/z 694.84, cal. 694.86

Example 11

Preparation of Compound 121

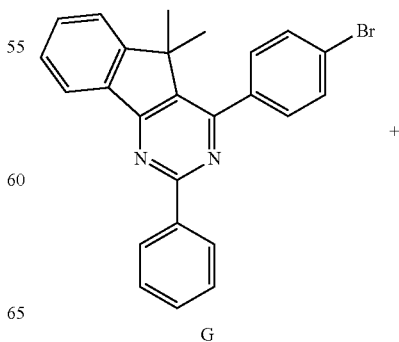

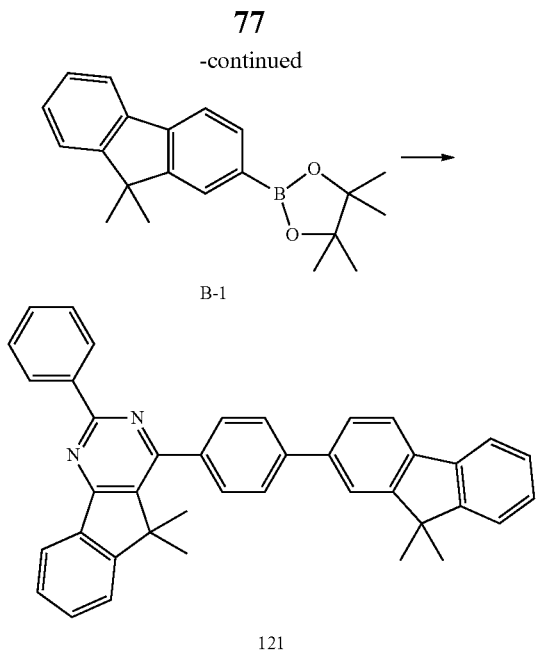

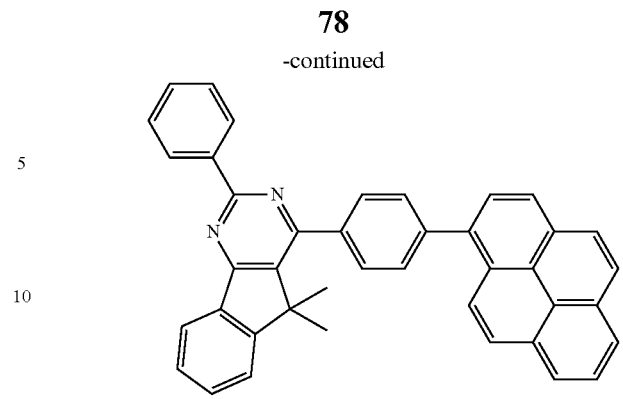

Compound G (Preparation Example 7, 13 g, 30.4 mmol), Compound B-1 (Preparation Example 2, 9.7 g, 30.4 mmol), THF (200 mL), Pd(PPh$_3$)$_4$ (0.7 g, 0.61 mmol), K$_2$CO$_3$ (25.2 g, 182.5 mmol), and distilled water (100 mL) were mixed and stirred under reflux for 18 hours. When the reaction was completed, the reactant was cooled to room temperature. Then, the precipitated solid was filtered and washed with methanol, thereby obtaining Compound 121 (14.2 g, 86.33%).

$^1$H NMR (CDCl$_3$) δ 8.62 (3H, m), 7.78 (2H, d), 7.68 (4H, q), 7.55 (7H, m), 7.38 (3H, m), 7.12 (1H, s)

MALDI-TOF MS: m/z 540.58, cal. 540.70

Example 12

Preparation of Compound 115

Compound G (Preparation Example 7, 24 g, 56.2 mmol), Compound K (Preparation Example 11, 18.43 g, 56.2 mmol), THF (360 mL), Pd(PPh$_3$)$_4$ (0.65 g, 0.56 mmol), and 1M K$_2$CO$_3$ aqueous solution (180 mL) were mixed and stirred under reflux for 18 hours. When the reaction was completed, the reactant was cooled to room temperature. Then, an organic layer was extracted with saturated sodium chloride aqueous solution and ethylacetate, dried over magnesium sulfate, and then treated with activated charcoal, followed by filtering with celite. A solid prepared by concentrating the filtrate under reduced pressure was suspended in ethyl acetate with heating, followed by filtering, thereby obtaining Compound 115 (21.8 g, 71%).

$^1$H NMR (CDCl$_3$) δ 8.18-8.12 (d, 2H), 8.04-7.82 (d, 1H), 7.88-7.80 (d, 2H), 7.71-7.65 (m, 4H), 7.54-7.26 (d, 4H), 7.48-7.16 (d, 2H), 7.40-7.22 (d, 1H), 7.32-7.26 (m, 3H), 7.19-7.13 (d, 1H), 7.14-7.18 (d, 2H), 1.67 (s, 6H)

MALDI-TOF MS: m/z 548.7, cal. 548.67

Example 13

Preparation of Compound 116

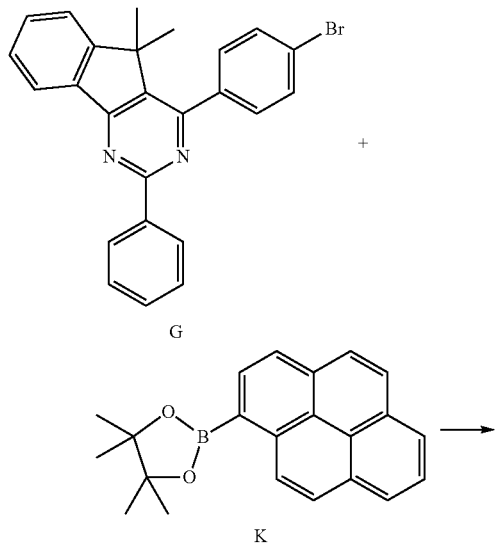

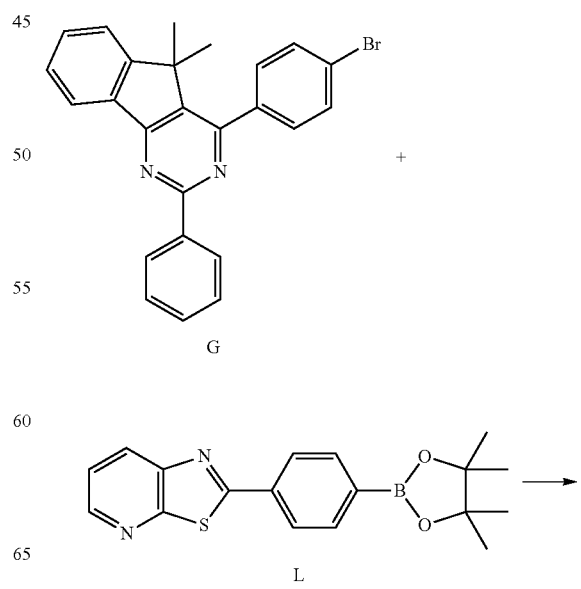

-continued

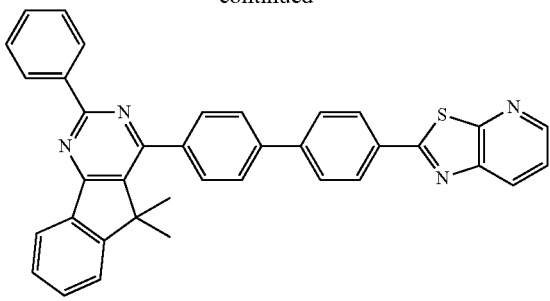

116

Compound G (Preparation Example 7, 24 g, 56.2 mmol), Compound L (Preparation Example 12, 19 g, 56.2 mmol), THF (360 mL), Pd(PPh$_3$)$_4$ (0.65 g, 0.56 mmol), and 1M K$_2$CO$_3$ aqueous solution (180 mL) were mixed and stirred under reflux for 18 hours. When the reaction was completed, the reactant was cooled to room temperature. Then, an organic layer was extracted with saturated sodium chloride aqueous solution and ethylacetate, dried over magnesium sulfate, and then treated with activated charcoal, followed by filtering with celite. A solid prepared by concentrating the filtrate under reduced pressure was suspended in ethyl acetate with heating, followed by filtering, thereby obtaining Compound 116 (22.9 g, 73%).

$^1$H NMR (CDCl$_3$) δ 8.59 (d, 1H), 7.75 (d, 1H), 7.54-7.26 (m, 10H), 7.40-7.22 (m, 5H), 7.19-7.06 (m, 3H), 1.67 (s, 6H)

MALDI-TOF MS: m/z 558.8, cal. 558.69

Example 14

Preparation of Compound 114

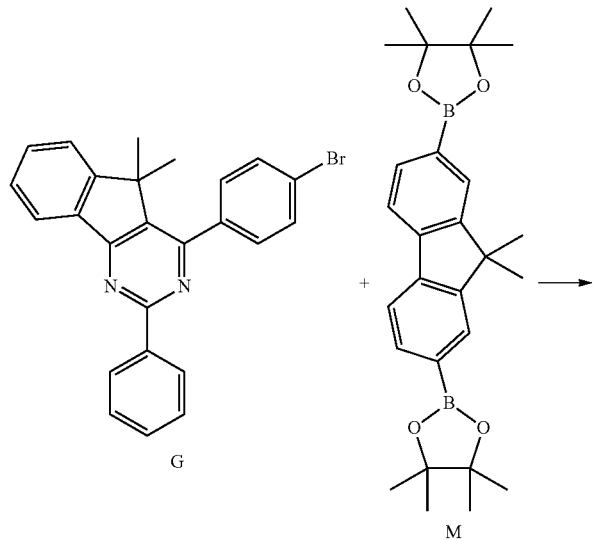

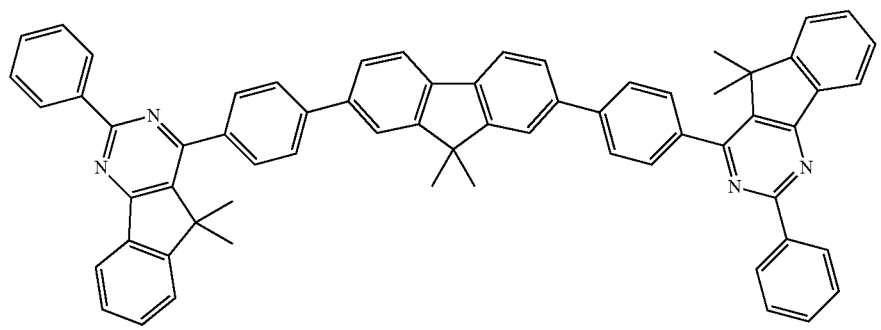

114

Compound G (Preparation Example 7, 24 g, 56.2 mmol), Compound M (Preparation Example 13, 15 g, 33.6 mmol), THF (225 mL), Pd(PPh$_3$)$_4$ (0.39 g, 0.336 mmol), and 1M K$_2$CO$_3$ aqueous solution (113 mL) were mixed and stirred under reflux for 18 hours. When the reaction was completed, the reactant was cooled to room temperature. Then, an organic layer was extracted with saturated sodium chloride aqueous solution and ethylacetate, dried over magnesium sulfate, and then treated with activated charcoal, followed by filtering with celite. A solid prepared by concentrating the filtrate under reduced pressure was suspended in ethyl acetate with heating, followed by filtering, thereby obtaining Compound 114 (21.56 g, 70%).

$^1$H NMR (CDCl$_3$) δ 7.90-7.84 (d, 2H), 7.77-7.38 (d, 4H), 7.54-7.26 (m, 12H), 7.40-7.22 (d, 2H), 7.32-7.06 (m, 6H), 7.19-7.04 (m, 6H), 1.67 (s, 24H)

LC-MS: m/z 887.2, cal. 887.12

Example 15

Preparation of Compound 117

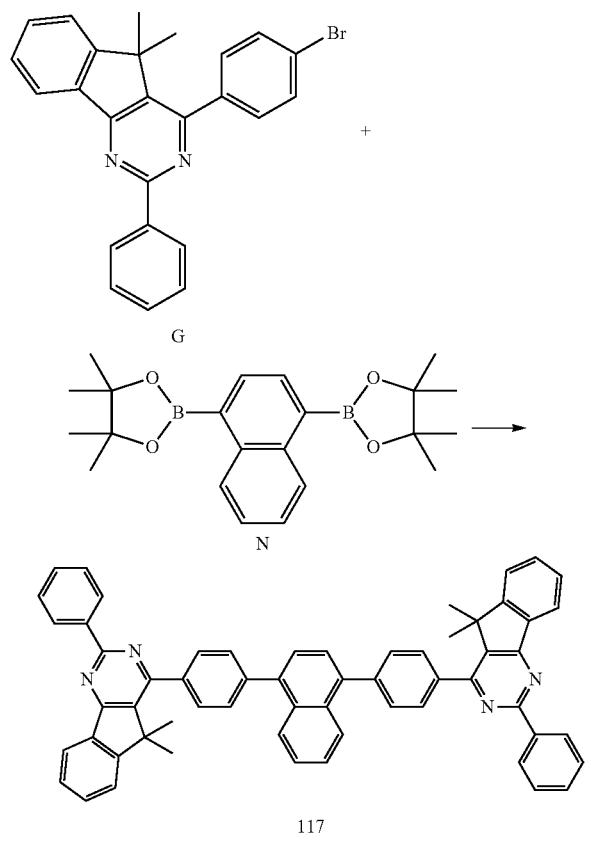

Compound G (Preparation Example 7, 35.42 g, 82.9 mmol), Compound N (Preparation Example 14, 15 g, 39.5 mmol), THF (225 mL), Pd(PPh$_3$)$_4$ (0.46 g, 0.395 mmol), and 1M K$_2$CO$_3$ aqueous solution (113 mL) were mixed and stirred under reflux for 18 hours. When the reaction was completed, the reactant was cooled to room temperature. Then, an organic layer was extracted with saturated sodium chloride aqueous solution and ethylacetate, dried over magnesium sulfate, and treated with activated charcoal, followed by filtering with celite. A solid prepared by concentrating the filtrate under reduced pressure was suspended in ethyl acetate with heating, followed by filtering, thereby obtaining Compound 117 (19.4 g, 60%).

$^1$H NMR (CDCl$_3$) δ 7.67 (d, 2H), 7.60-7.32 (d, 2H), 7.54-7.26 (m, 8H), 7.48-7.22 (m, 6H), 7.32-7.06 (m, 6H), 7.22-7.04 (m, 4H), 7.14-7.01 (m, 4H), 1.67 (s, 12H)

MALDI-TOF MS: m/z 821.1, cal. 821.02

Example 16

Manufacturing Organic Electroluminescent Device Using Compound 100 According to the Present Invention A glass substrate (25 mm×25 mm×0.7 mm) having an indium tin oxide (ITO) transparent electrode line having a thickness of 150 nm was subjected to ultrasonic cleaning for 10 minutes in distilled water in which a detergent was dissolved and then cleaned with distilled water again for 10 minutes. After washing with distilled water, the substrate was subjected to ultrasonic cleaning with solvents in a sequence of isopropyl alcohol, acetone, and methanol for 10 minutes, respectively, and dried. Thereafter, the substrate was dry cleaned using oxygen/argon plasma, then the glass substrate having the transparent electrode line was mounted on a substrate holder of a vacuum vapor deposition apparatus. A film having a thickness of 60 nm was formed on a surface on which the transparent electrode line was formed as a hole injection layer using IDE-406 (the following structure, Idemitsu) so as to cover the transparent electrode. Next, a film having a thickness of 30 nm was formed on the IDE-406 film as a hole transport layer using H-1 (tetrakis-N-biphenyl-4-yl-benzidine, hereinafter, referred to as the H-1 film). Then, BD-1 having the following structure and β-ADN (9,10-di(naphthalene-2-yl)anthracene) were deposited on the H-1 film as a dopant and a luminescent host at a weight ratio of 5%, to thereby form a film having a thickness of 20 nm as a luminescent layer.

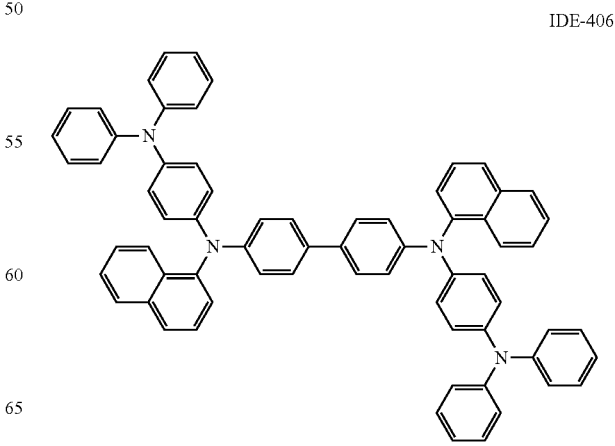

IDE-406

-continued

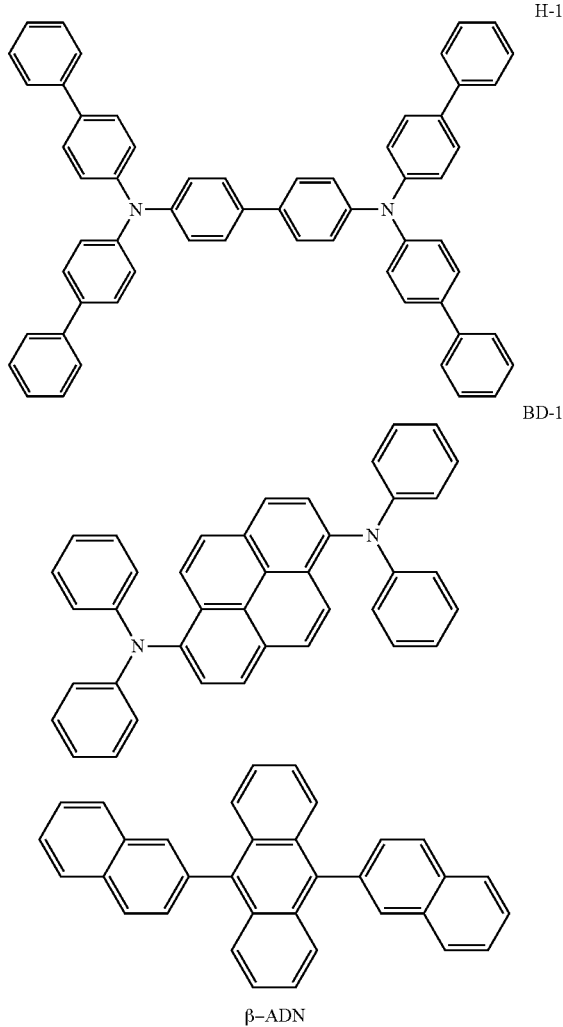

A film having a thickness of 20 nm was formed on the luminescent layer as an electron transport layer by depositing Compound 100 according to the present invention. Subsequently, lithium quinolate (Liq) was deposited thereon to form an electron injection layer. Metal aluminum was deposited on this Liq film to form a metal cathode, thereby manufacturing the organic electroluminescent device.

Example 17

Manufacturing Organic Electroluminescent Device Using Compound 98 According to the Present Invention An organic electroluminescent device was manufactured by the same process in Example 16 except that Compound 98 was used as an electron transport material instead of Compound 100 in Example 16.

Example 18

Manufacturing Organic Electroluminescent Device Using Compound 105 According to the Present Invention An organic electroluminescent device was manufactured by the same process in Example 16 except that Compound 105 was used as an electron transport material instead of Compound 100 in Example 16.

Example 19

Manufacturing Organic Electroluminescent Device Using Compound 106 According to the Present Invention An organic electroluminescent device was manufactured by the same process in Example 16 except that Compound 106 was used as an electron transport material instead of Compound 100 in Example 16.

Example 20

Manufacturing Organic Electroluminescent Device Using Compound 113 According to the Present Invention An organic electroluminescent device was manufactured by the same process in Example 16 except that Compound 113 was used as an electron transport material instead of Compound 100 in Example 16.

Example 21

Manufacturing Organic Electroluminescent Device Using Compound 110 According to the Present Invention An organic electroluminescent device was manufactured by the same process in Example 16 except that Compound 110 was used as an electron transport material instead of Compound 100 in Example 16.

Example 22

Manufacturing Organic Electroluminescent Device Using Compound 114 According to the Present Invention An organic electroluminescent device was manufactured by the same process in Example 16 except that Compound 114 was used as an electron transport material instead of Compound 100 in Example 16.

Example 23

Manufacturing Organic Electroluminescent Device Using Compound 115 According to the Present Invention An organic electroluminescent device was manufactured by the same process in Example 16 except that Compound 115 was used as an electron transport material instead of Compound 100 in Example 16.

Example 24

Manufacturing Organic Electroluminescent Device Using Compound 116 According to the Present Invention An organic electroluminescent device was manufactured by the same process in Example 16 except that Compound 116 was used as an electron transport material instead of Compound 100 in Example 16.

Example 25

Manufacturing Organic Electroluminescent Device Using Compound 117 According to the Present Invention An organic electroluminescent device was manufactured by the same process in Example 16 except that Compound 117 was used as an electron transport material instead of Compound 100 in Example 16.

Example 26

Manufacturing Organic Electroluminescent Device Using Compound 118 According to the Present Invention An organic electroluminescent device was manufactured by the same process in Example 16 except that Compound 118 was used as an electron transport material instead of Compound 100 in Example 16.

Example 27

Manufacturing Organic Electroluminescent Device Using Compound 119 According to the Present Invention An organic electroluminescent device was manufactured by the same process in Example 16 except that Compound 119 was used as an electron transport material instead of Compound 100 in Example 16.

Example 28

Manufacturing Organic Electroluminescent Device Using Compound 120 According to the Present Invention An organic electroluminescent device was manufactured by the same process in Example 16 except that Compound 120 was used as an electron transport material instead of Compound 100 in Example 16.

Example 29

Manufacturing Organic Electroluminescent Device Using Compound 121 According to the Present Invention An organic electroluminescent device was manufactured by the same process in Example 16 except that Compound 121 was used as an electron transport material instead of Compound 100 in Example 16.

Example 30

Manufacturing Organic Electroluminescent Device Using Compound 123 According to the Present Invention An organic electroluminescent device was manufactured by the same process in Example 16 except that Compound 123 was used as an electron transport material instead of Compound 100 in Example 16.

Comparative Example 1

Manufacturing Organic Electroluminescent Device Using Compound ETM-1

An organic electroluminescent device was manufactured by the same process in Example 7 except that Compound ETM-1 having the following structure was used as an electron transport material instead of Compound 100 in Example 7.

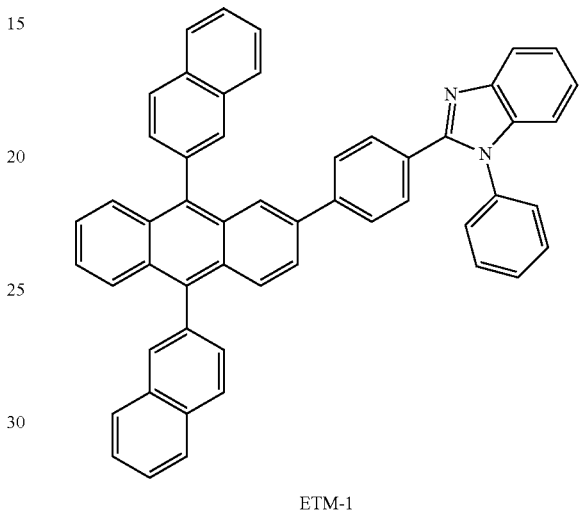

ETM-1

Figure 2:
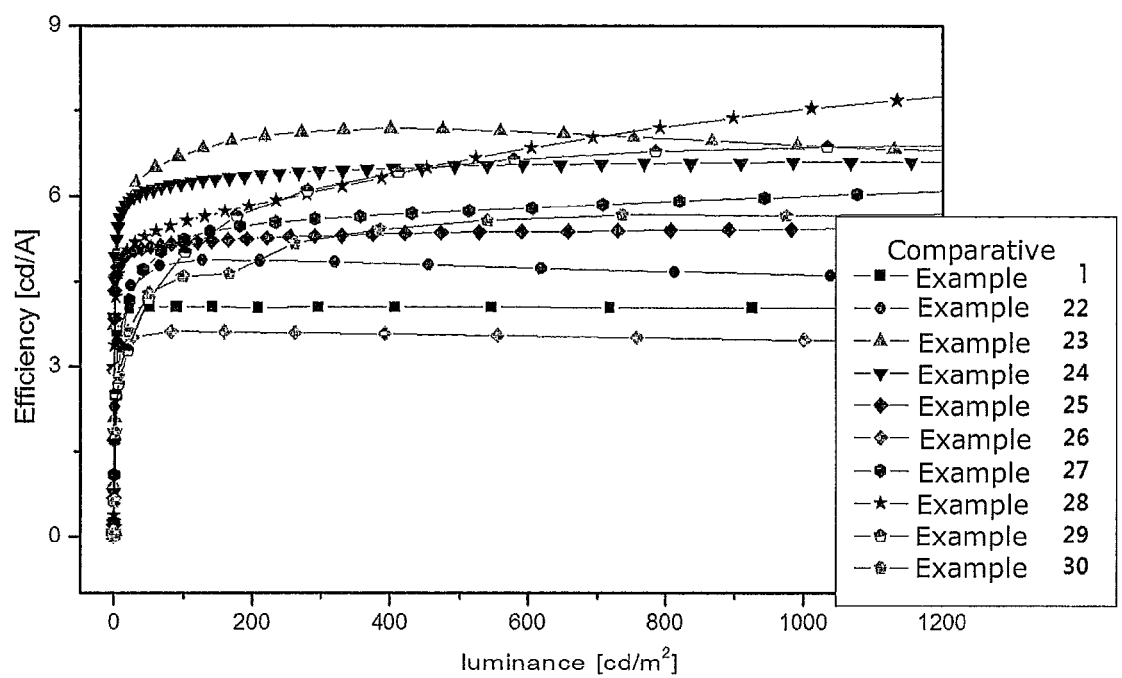
FIG. 2 is a graph showing efficiency (cd/A) and luminance (cd/m$^2$) of organic electroluminescent devices manufactured in Examples 22 to 30 and Comparative Example 1.

Measurement results of electroluminescence properties and basic physical properties of the organic electroluminescent devices manufactured in Examples 16 to 30 and Comparative Example 1 were shown in Table 1, and a graph of efficiency (cd/A) and luminance (cd/m$^2$) of the organic electroluminescent devices manufactured in Examples 16 to 21 and Comparative Example 1 was shown in FIG. 1. In addition, a graph of efficiency (cd/A) and luminance (cd/m$^2$) of the organic electroluminescent devices manufactured in Examples 22 to 30 and Comparative Example 1 was shown in FIG. 2.

TABLE 1

| No. | Voltage (V) | Current density (mA/cm$^2$) | Efficiency (cd/A) | Color coordinate (x, y) | Luminance (cd/m$^2$) |
|---|---|---|---|---|---|
| Example 16 | 4.60 | 14.71 | 7.46 | (0.137, 0.151) | 1099 |
| Example 17 | 4.80 | 14.14 | 8.06 | (0.136, 0.153) | 1140 |
| Example 18 | 4.80 | 15.07 | 6.86 | (0.138, 0.156) | 1035 |
| Example 19 | 4.80 | 15.64 | 6.54 | (0.136, 0.149) | 1024 |
| Example 20 | 4.80 | 13.65 | 7.35 | (0.135, 0.151) | 1004 |
| Example 21 | 5.20 | 20.64 | 6.07 | (0.135, 0.148) | 1255 |
| Example 22 | 4.8 | 22.66 | 4.5 | (0.13, 0.14) | 1040 |
| Example 23 | 4.8 | 16.58 | 6.8 | (0.13, 0.14) | 1130 |
| Example 24 | 7.2 | 16.17 | 6.5 | (0.13, 0.17) | 1067 |
| Example 25 | 6.4 | 19.93 | 5.4 | (0.13, 0.14) | 1081 |
| Example 26 | 4.4 | 28.93 | 3.4 | (0.13, 0.14) | 1002 |
| Example 27 | 7.2 | 17.87 | 6.0 | (0.13, 0.14) | 1077 |
| Example 28 | 4.8 | 13.42 | 7.5 | (0.13, 0.17) | 1011 |
| Example 29 | 4.8 | 15.07 | 6.8 | (0.13, 0.15) | 1035 |
| Example 30 | 5.2 | 22.28 | 5.6 | (0.13, 0.14) | 1267 |
| Comparative Example 1 | 5.00 | 29.05 | 4.03 | (0.135, 0.143) | 1170 |

As shown in Table 1, it may be confirmed that the material according to the present invention had excellent luminescence properties as compared with the material according to the related art. In addition, the organic electroluminescent device using the heteroaromatic cyclic compound according to the present invention as the electron transport layer had an excellent luminescence property and decreased driving current to increase the power efficiency, thereby using less consumption power.

As set forth above, the electron transport material according to the present invention may have the excellent luminescence property and decrease the driving voltage to increase the power efficiency, such that the organic electroluminescent device using less consumption power may be manufactured.

What is claimed is:

1. An electron transport material represented by the following Chemical Formula 1,

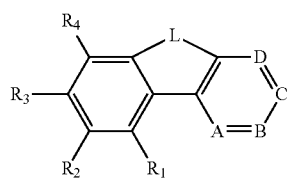

[Chemical Formula 1]

wherein in Chemical Formula 1,

A and C are N, B and D are independently C-$(L_1)_m$-$Ar_1$, and each of -$(L_1)_m$-$Ar_1$ are the same as or different from each other, but two -$(L_1)_m$-$Ar_1$ are not hydrogen at the same time;

L is ($C_1$-$C_2$)alkylene or ($C_2$)alkenylene;

$R_1$ to $R_4$ each are independently hydrogen, (C1-C30)alkyl, (C3-C30)cycloalkyl, (C6-C30)aryl, or (C3-C30)heteroaryl;

$L_1$(s) each are independently a single bond, (C6-C30)arylene, or (C3-C30)heteroarylene;

m is an integer of 1 to 3, and when m is an integer of 2 or more, $L_1$(s) are the same as or different from each other;

Ar(s) each are independently hydrogen, (C1-C30)alkyl, (C6-C30)aryl, or (C3-C30)heteroaryl; alkyl, cycloalkyl, aryl, heteroaryl of $R_1$ to $R_4$, alkylene or alkenylene of L, arylene and heteroarylene of $L_1$, and aryl and heteroaryl of $Ar_1$ are substituted with at least one selected from a group consisting of (C1-C30)alkyl, halo(C1-C30)alkyl, halogen, cyano, (C3-C30)cycloalkyl, (C1-C30)alkoxy, (C6-C30)aryloxy, (C6-C30)aryl, (C6-C30)ar(C1-C30)alkyl, (C1-C30)alkyl(C6-C30)aryl, (C3-C30)heteroaryl, (C3-C30)heteroaryl substituted with (C1-C30)alkyl, (C3-C30)heteroaryl substituted with (C6-C30)aryl, mono or di(C1-C30)alkylamino, mono or di(C6-C30)arylamino, tri(C1-C30)alkylsilyl, di(C1-C30)alkyl(C6-C30)arylsilyl, tri(C6-C30)arylsilyl, nitro, and hydroxy; and heteroarylene and heteroaryl contains at least one hetero atom selected from B, N, O, S, P(=O), Si, and P.

2. The electron transport material of claim 1, wherein it is represented by the following Chemical Formula 2:

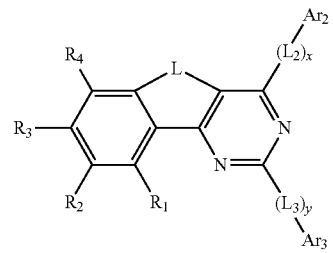

[Chemical Formula 2]

wherein in Chemical Formulas 2, $R_1$ to $R_4$ and L each has the same definition in Chemical Formula 1 of claim 1;

$L_2$ and $L_3$ each are independently a single bond, (C6-C30)arylene, or (C3-C30)heteroarylene;

x and y each are independently an integer of 1 to 3, wherein when x is an integer of 2 or more, $L_2$(s) are the same as or different from each other, and when y is an integer of 2 or more, $L_3$(s) are the same as or different from each other;

$Ar_2$ and $Ar_3$ each are independently hydrogen, (C1-C30)alkyl, (C6-C30)aryl, or (C3-C30)heteroaryl;

arylene and heteroarylene of $L_2$ and $L_3$, and aryl and heteroaryl of $Ar_2$ and $Ar_3$ are substituted with at least one selected from a group consisting of (C1-C30)alkyl, halo(C1-C30)alkyl, halogen, cyano, (C3-C30)cycloalkyl, (C1-C30)alkoxy, (C6-C30)aryloxy, (C6-C30)aryl(C6-C30)ar(C1-C30)alkyl, (C1-C30)alkyl(C6-C30)aryl, (C3-C30)heteroaryl, (C3-C30)heteroaryl substituted with (C1-C30)alkyl, (C3-C30)heteroaryl substituted with (C6-C30)aryl, mono or di(C1-C30)alkylamino, mono or di(C6-C30)arylamino, tri(C1-C30)alkylsilyl, di(C1-C30)alkyl(C6-C30)arylsilyl, tri(C6-C30)arylsilyl, nitro, and hydroxy; and -$(L_2)_x$-$Ar_2$ and -$(L_3)_y$-$Ar_3$ are not hydrogen at the same time.

3. The electron transport material of claim 2, wherein it is represented by the following Chemical Formulas 4 to 6:

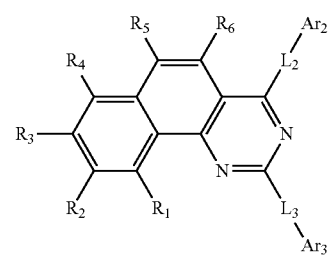

[Chemical Formula 4]

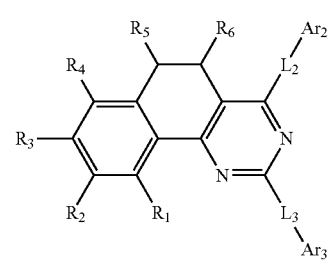

[Chemical Formula 5]

-continued

[Chemical Formula 6]

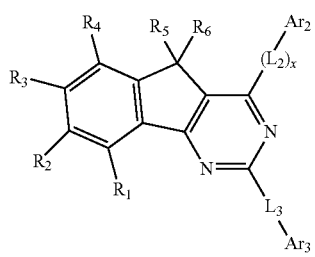

wherein in Chemical Formulas 4 to 6,

R₁ to R₆ each are independently hydrogen, (C1-C30)alkyl, (C3-C30)cycloalkyl, (C6-C30)aryl, or (C3-C30)heteroaryl;

L₂ and L₃ each are independently a single bond, (C6-C30)arylene, or (C3-C30)heteroarylene;

x is an integer of 1 to 3, and when x is an integer of 2 or more, L₂(s) are the same as or different from each other;

Ar₂ and Ar₃ each are independently hydrogen, (C1-C30)alkyl, (C6-C30)aryl, or (C3-C30)heteroaryl; and arylene of L₂ and L₃ and aryl and heteroaryl of Ar₂ and Ar₃ are further substituted with at least one selected from a group consisting of (C1-C30)alkyl, (C6-C30)aryl, (C6-C30)ar(C1-C30)alkyl, (C1-C30)alkyl(C6-C30)aryl, and (C3-C30)heteroaryl.

4. The electron transport material of claim 3, wherein L₂ and L₃ each are a single bond, phenylene, biphenylene, 9,9-dimethylfluorenylene, naphthylene, anthrylene, pyridinylene, or pyrimidinylene;

Ar₂ and Ar₃ each are independently hydrogen, (C1-C30)alkyl, or selected from the following structure:

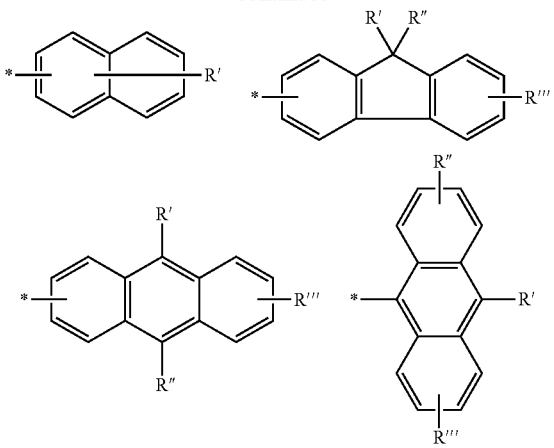

and

R', R'', and R''' each are independently hydrogen, (C1-C30)alkyl, (C6-C30)aryl, (C3-C30)heteroaryl, or (C1-C30)alkyl(C6-C30)aryl.

5. The electron transport material of claim 4, wherein the electron transport material is selected from the following compounds:

91 92
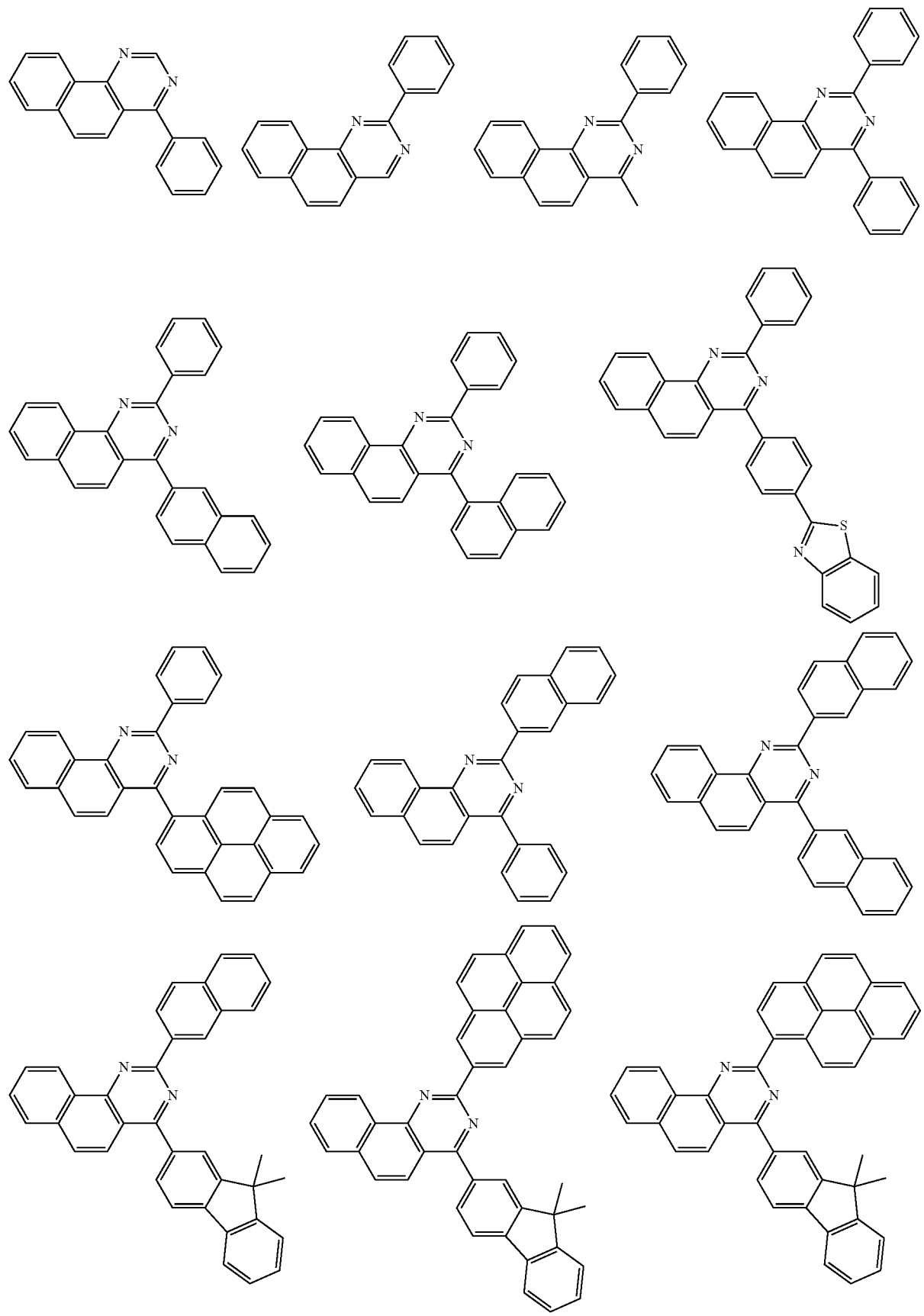

93
-continued
94
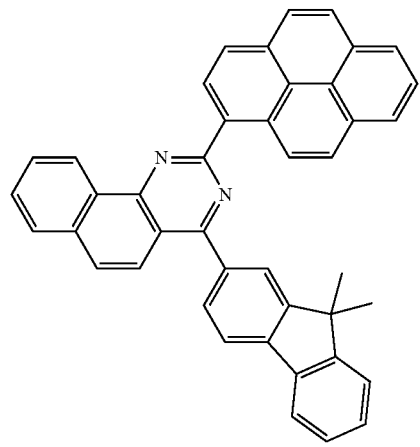
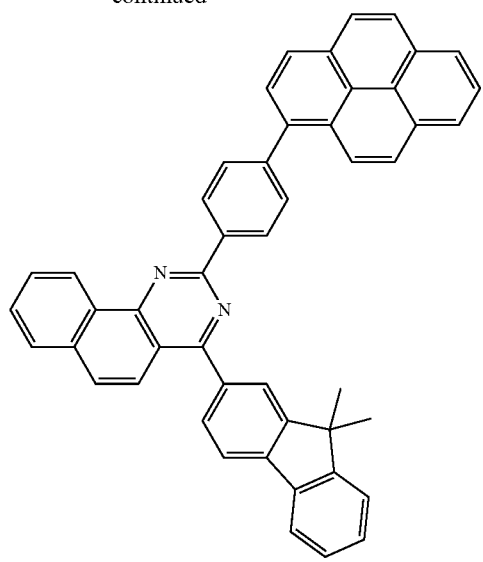
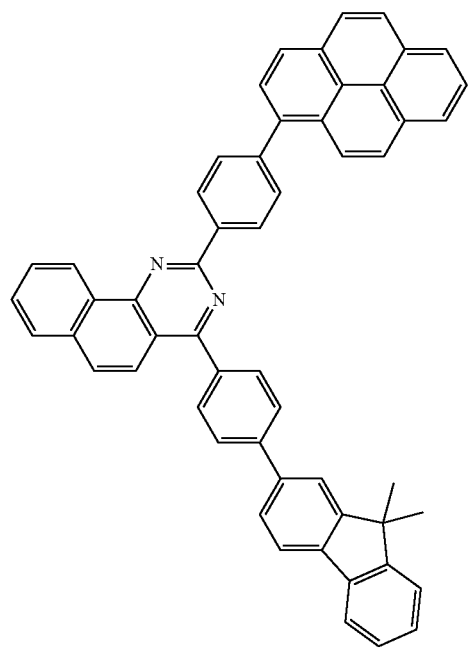
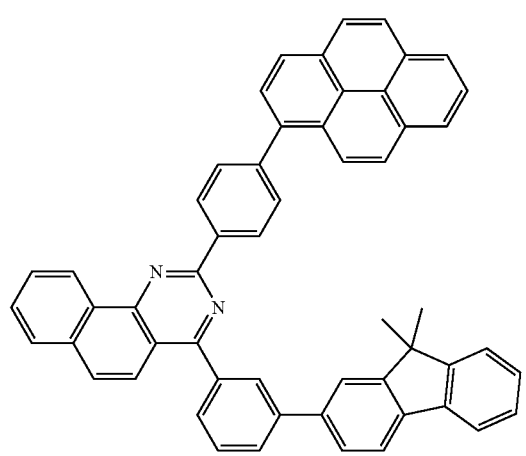
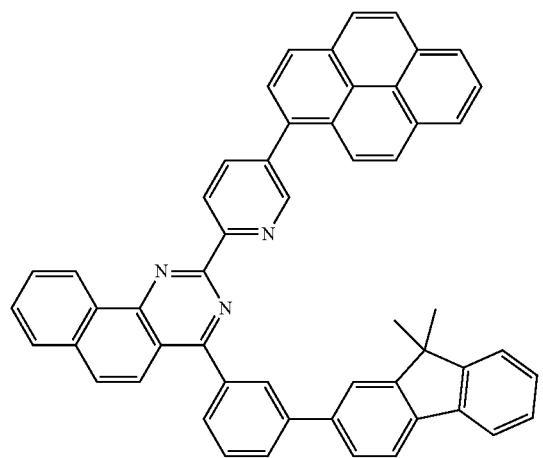
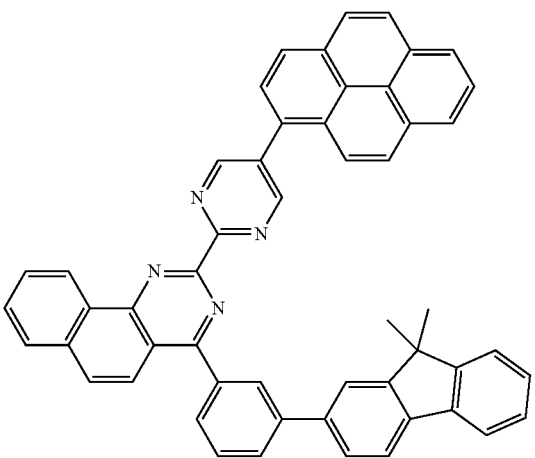

-continued
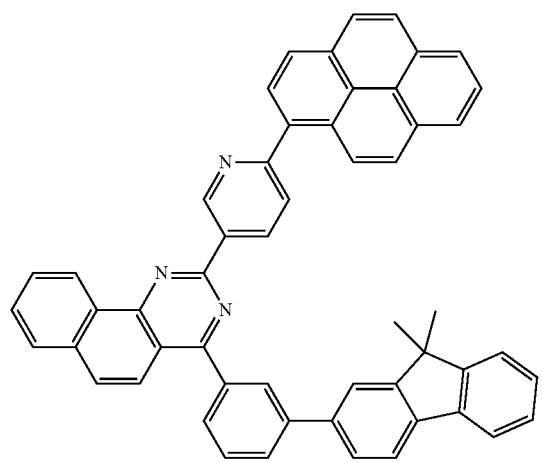
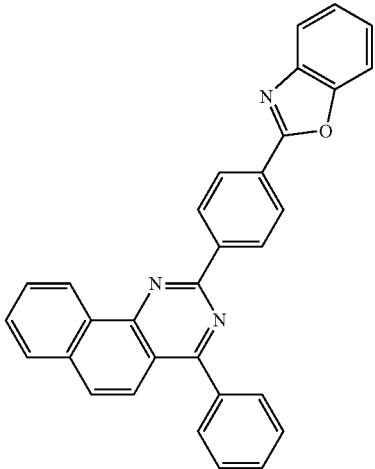
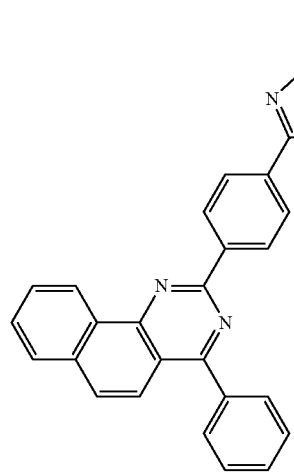
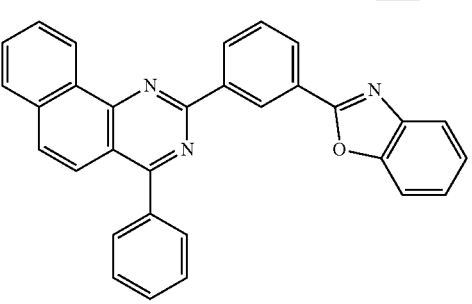
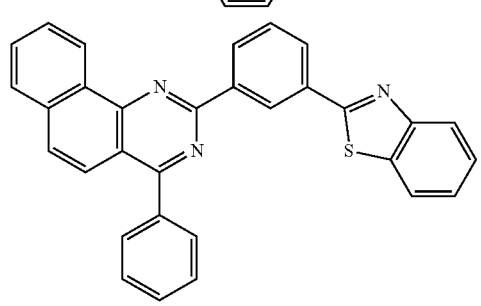
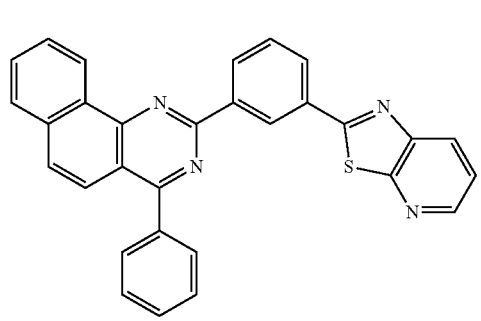
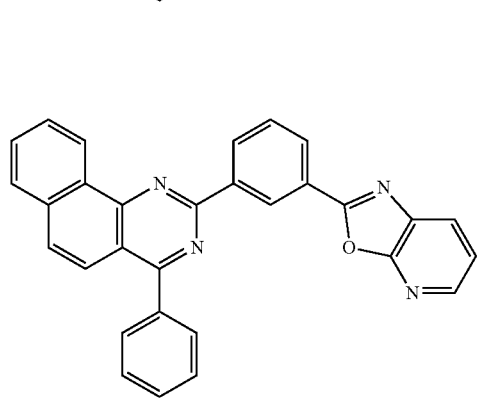
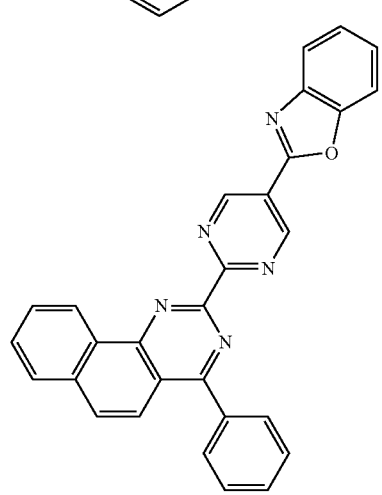

-continued
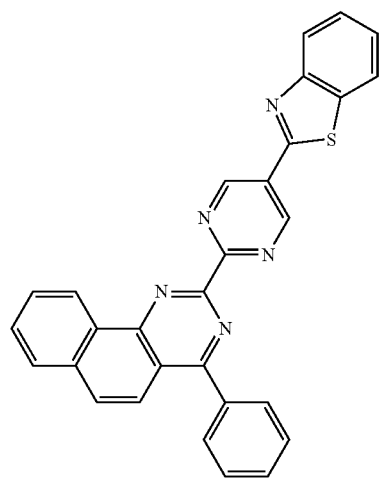
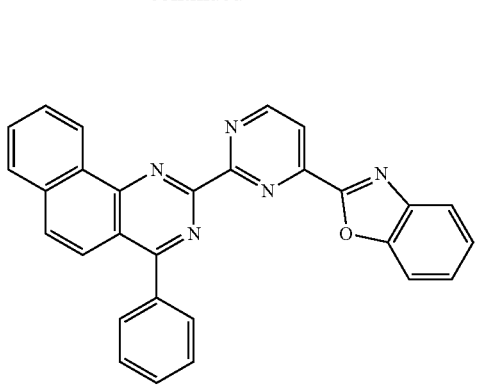
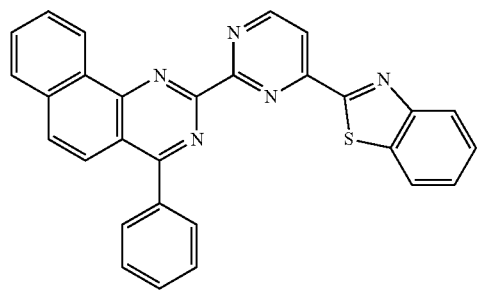
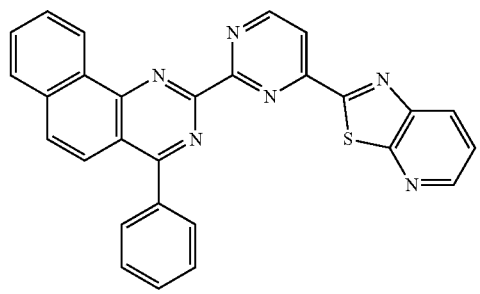
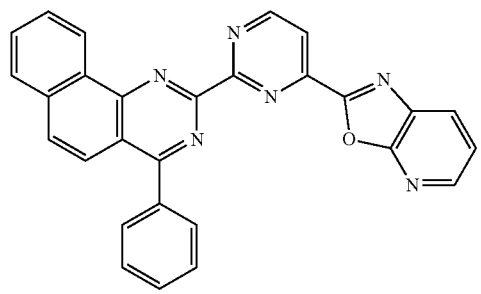
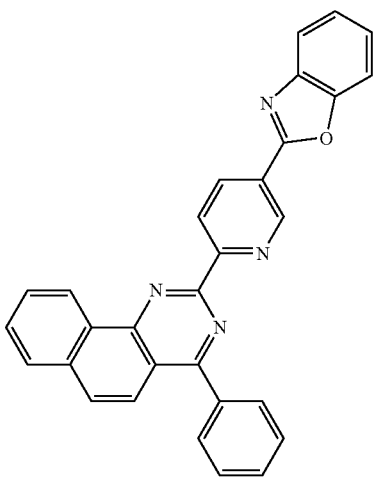
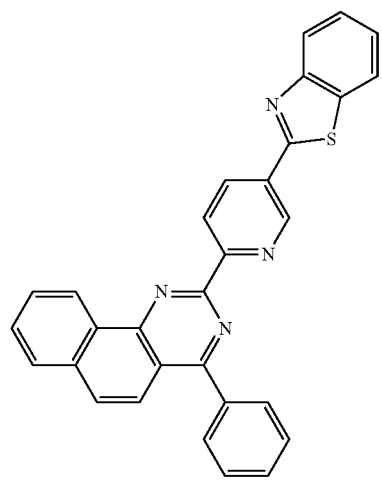
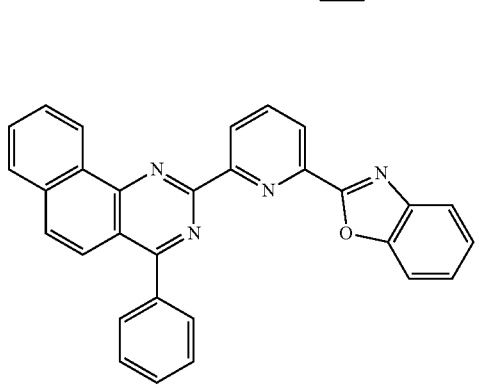

99
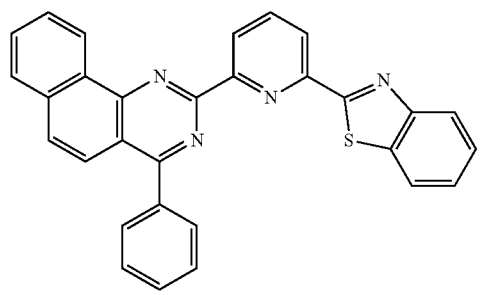
100
-continued
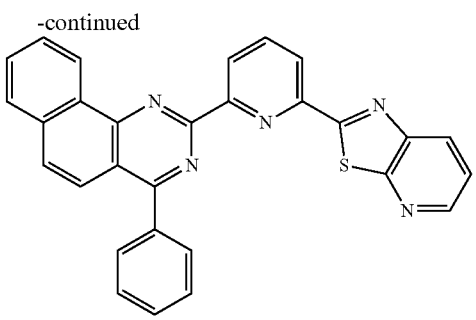
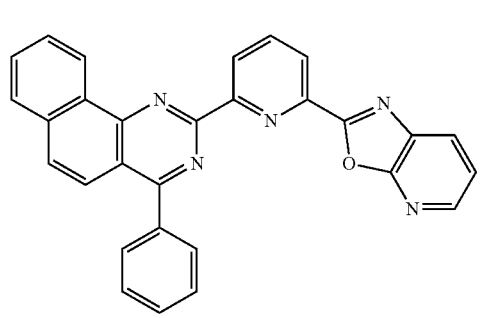
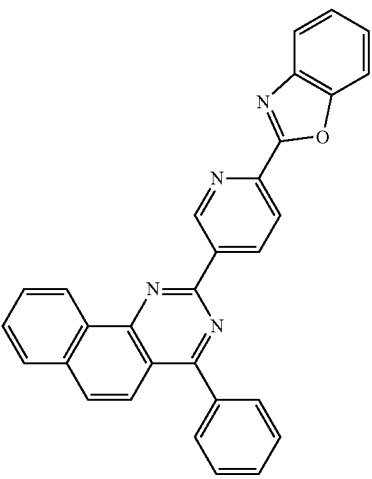
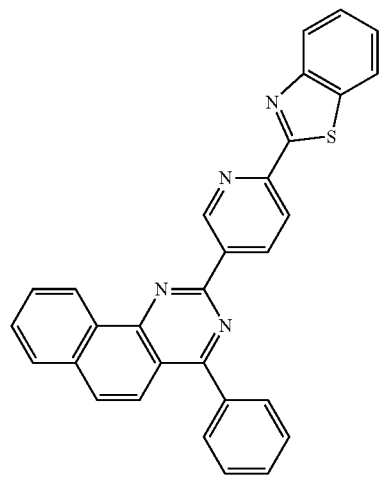
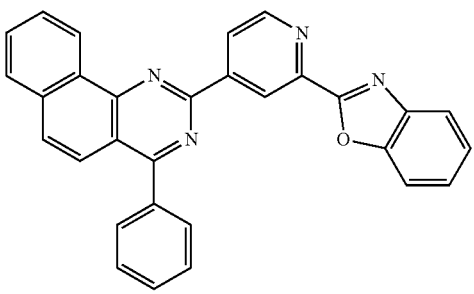
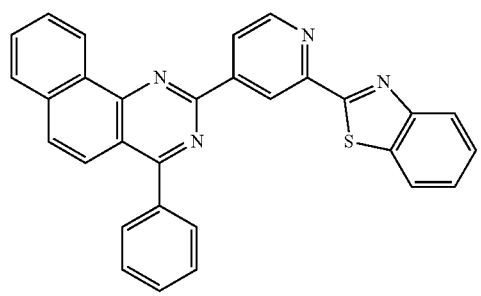
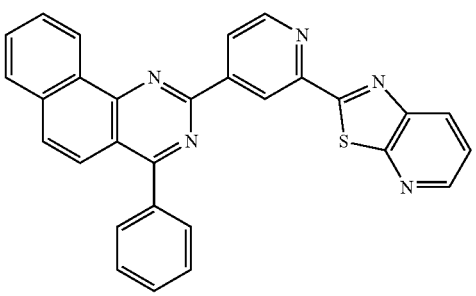

101 102
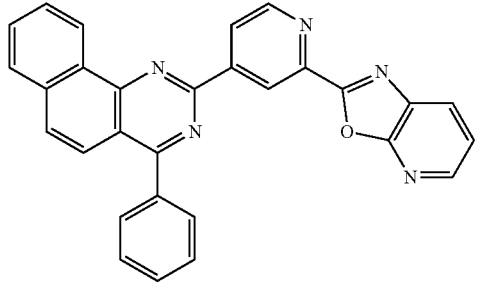 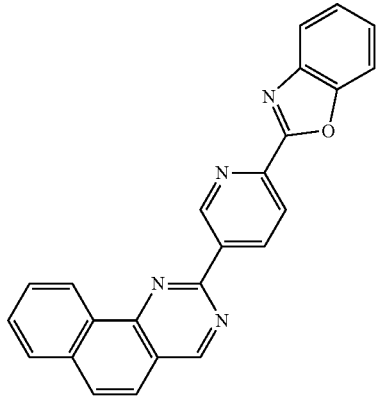
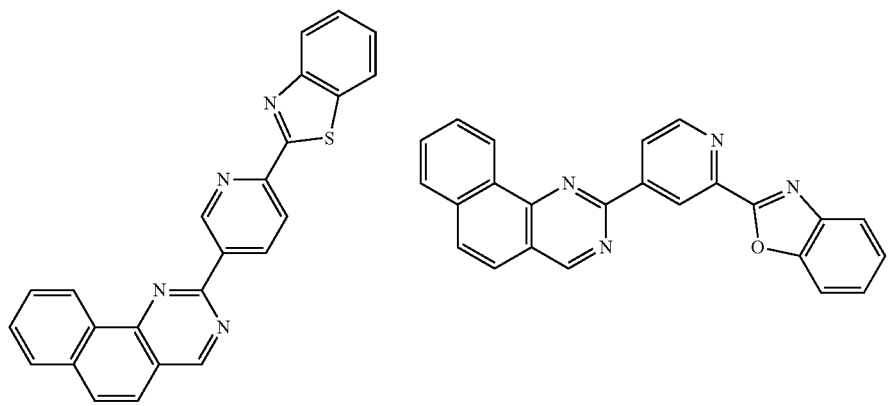
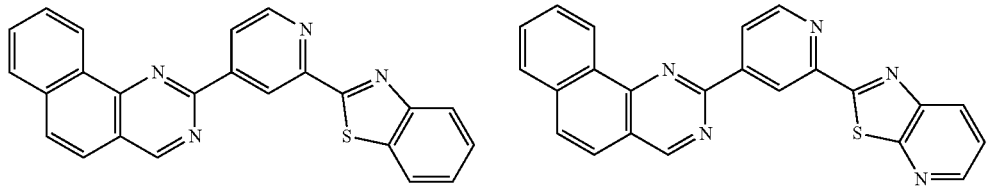
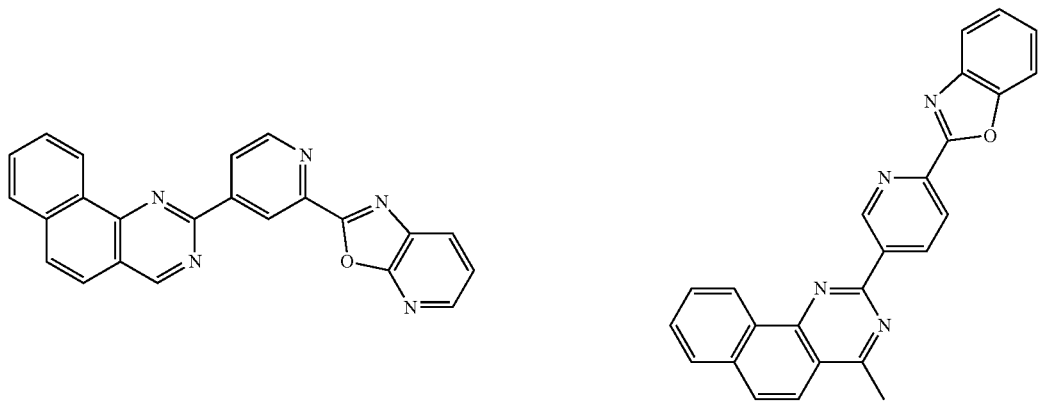

103
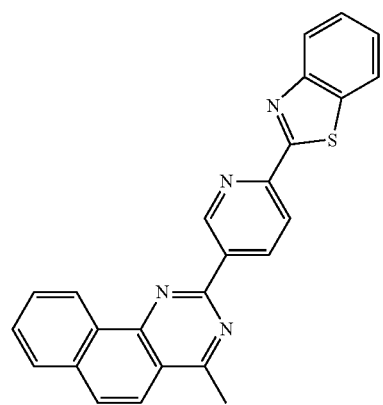
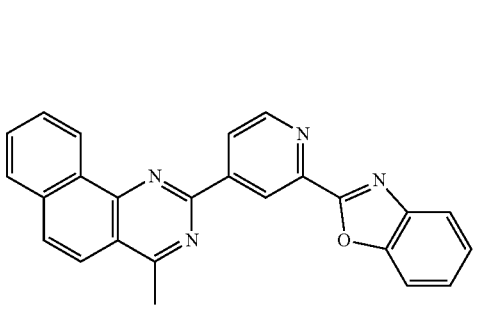
-continued
104
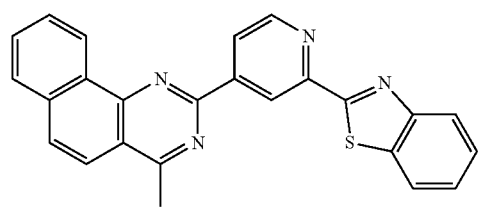
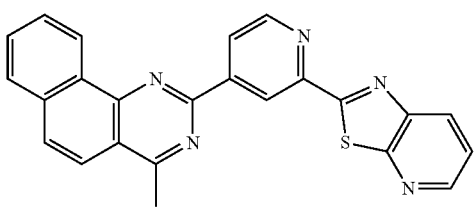
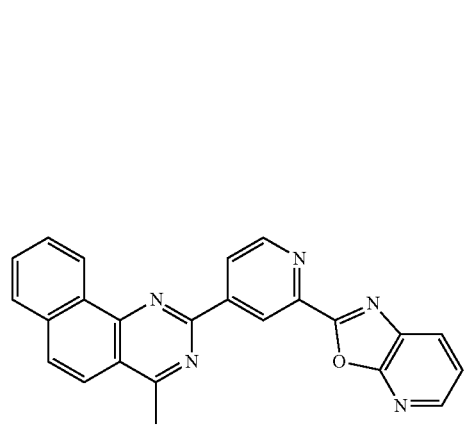
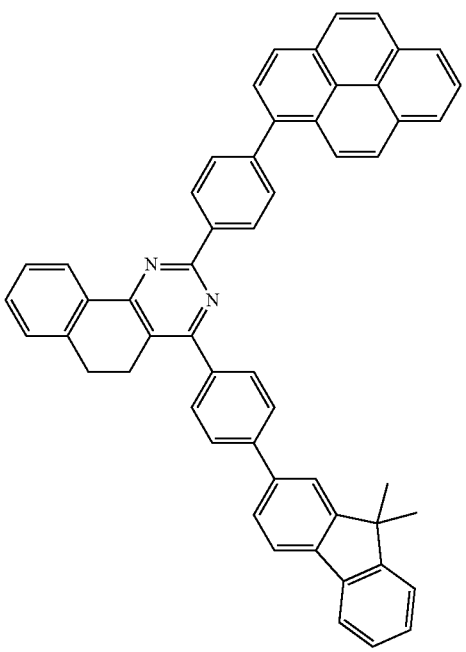
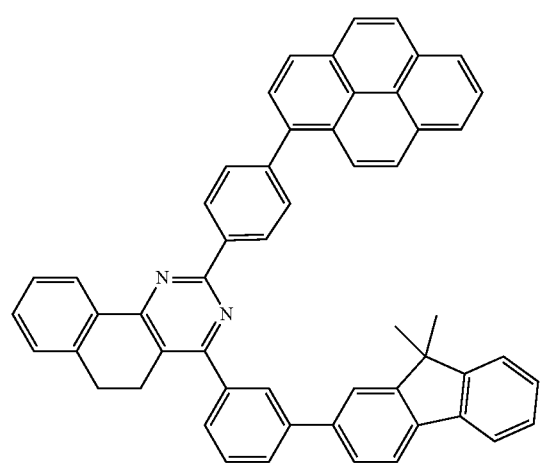
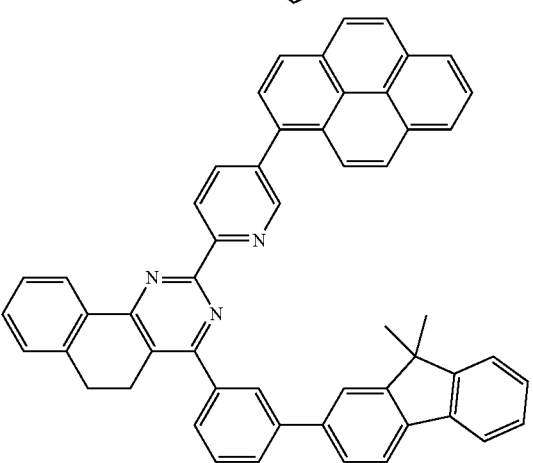

105
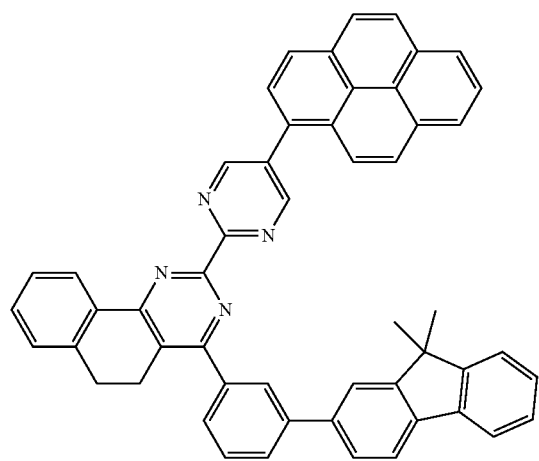
106
-continued
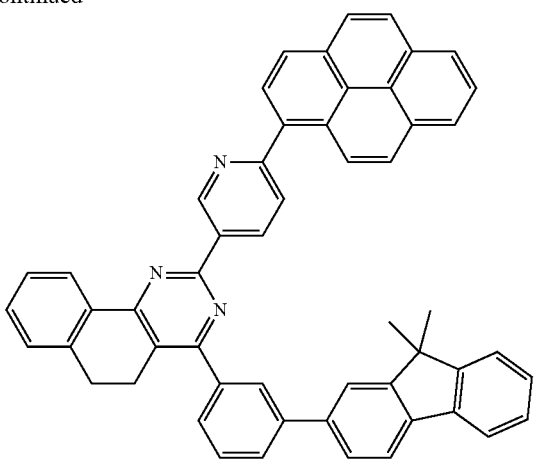
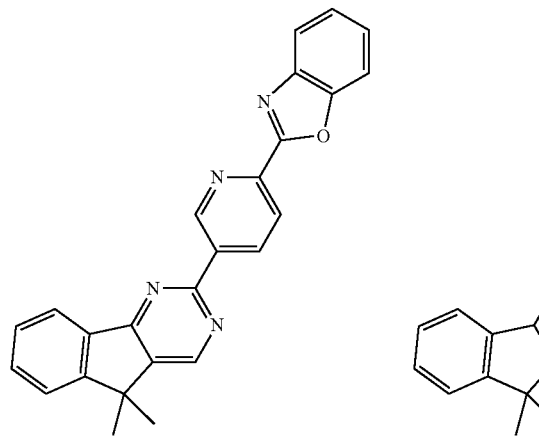
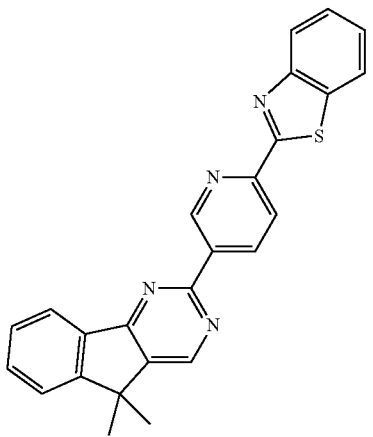
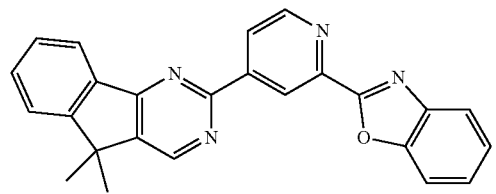
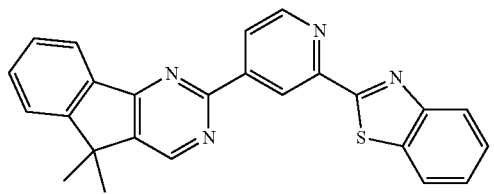
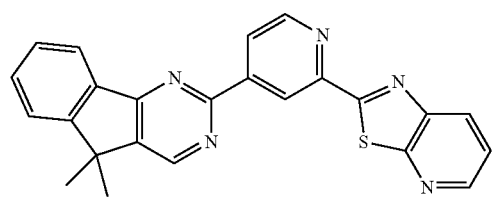
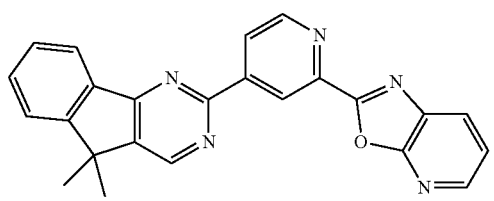
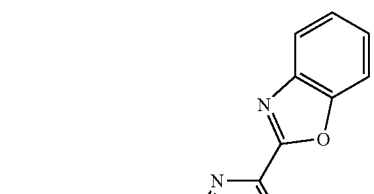
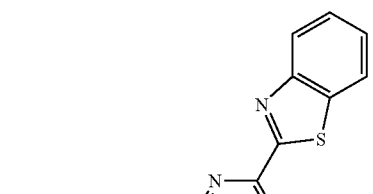
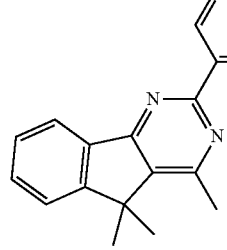
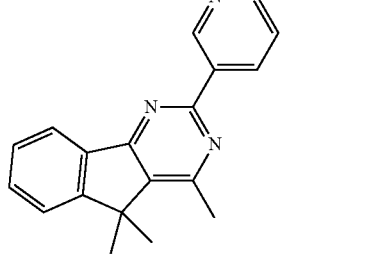

107
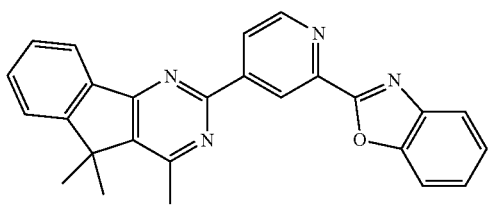
108
-continued
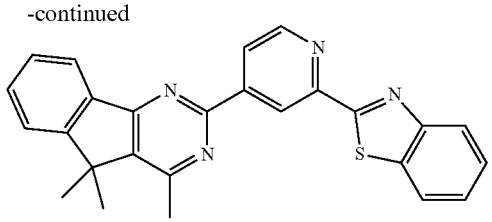
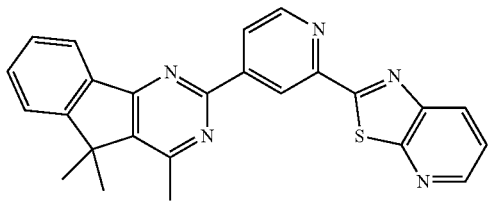
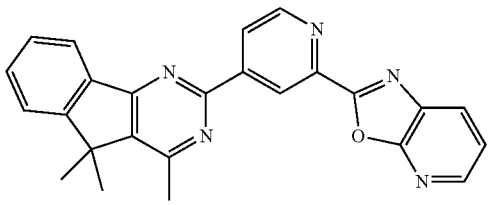
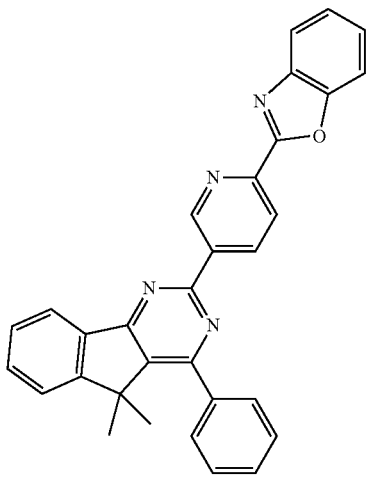
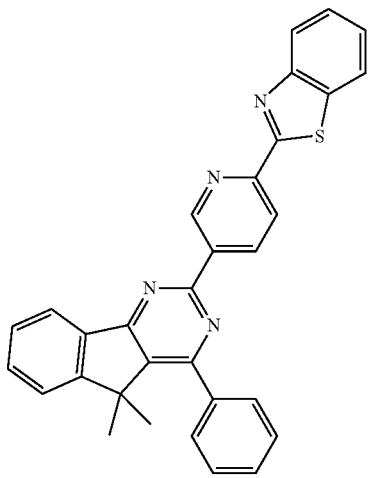
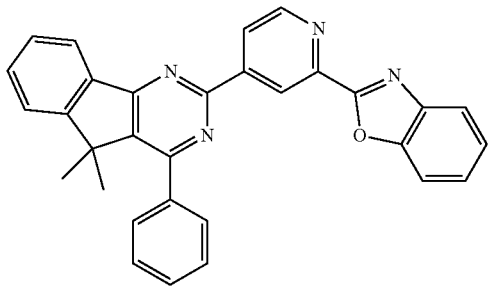
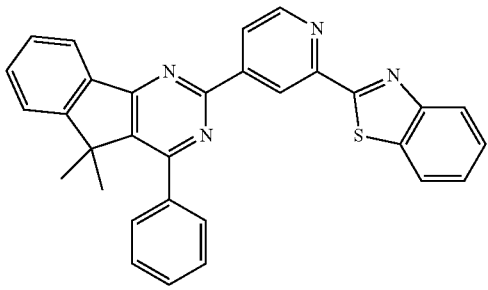
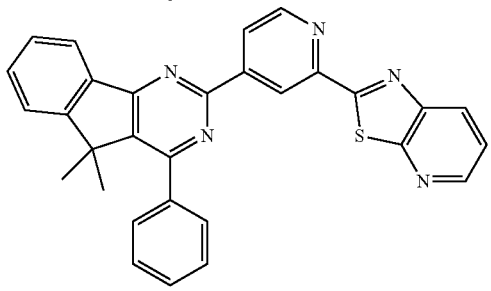
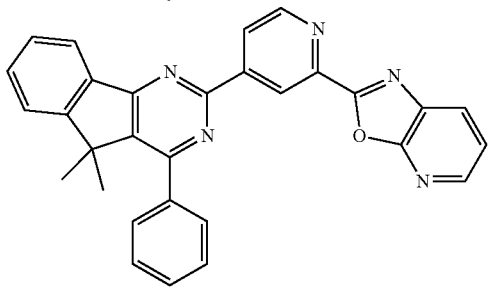

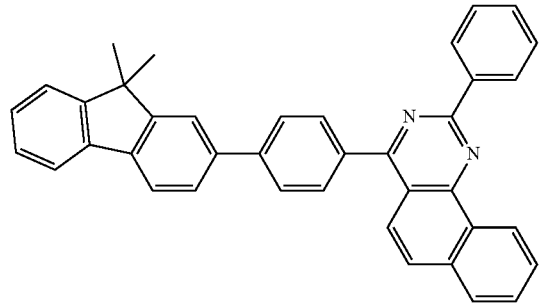
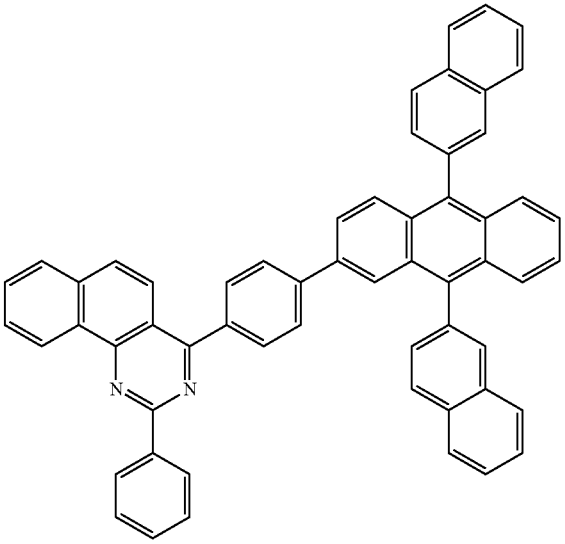
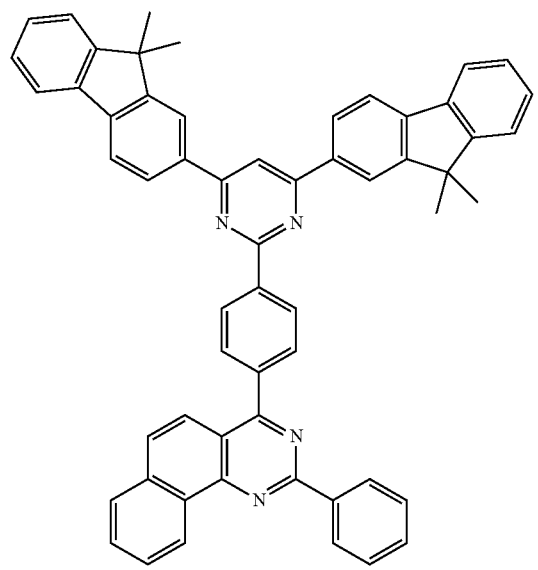
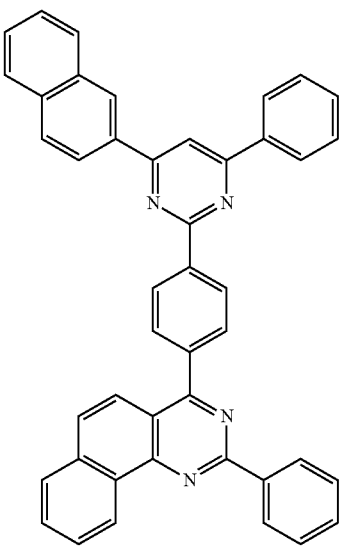
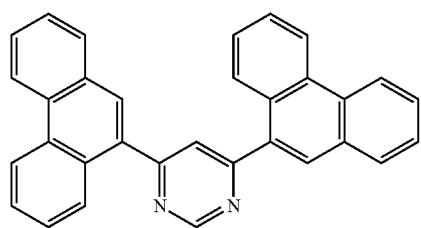
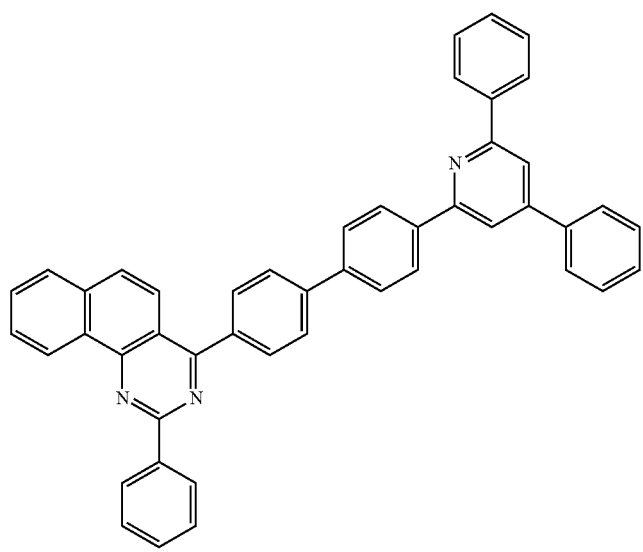

111 112
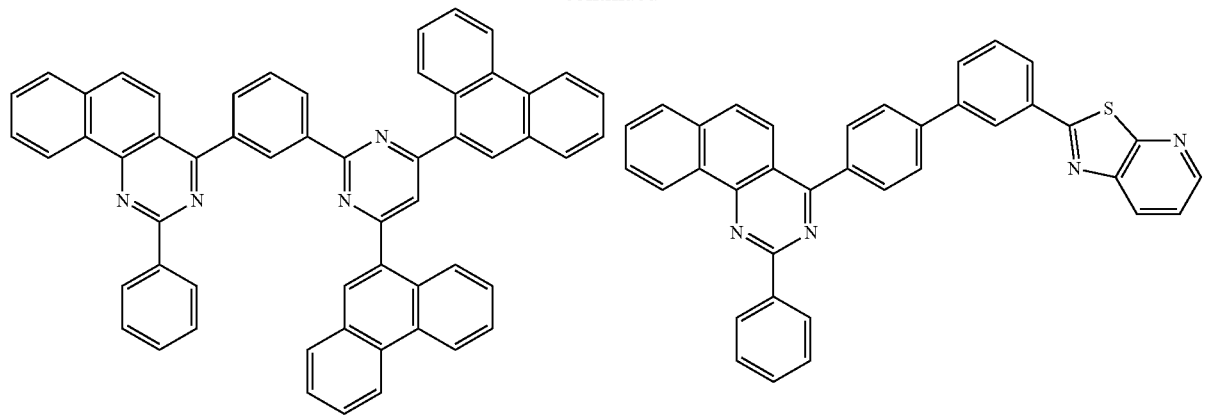
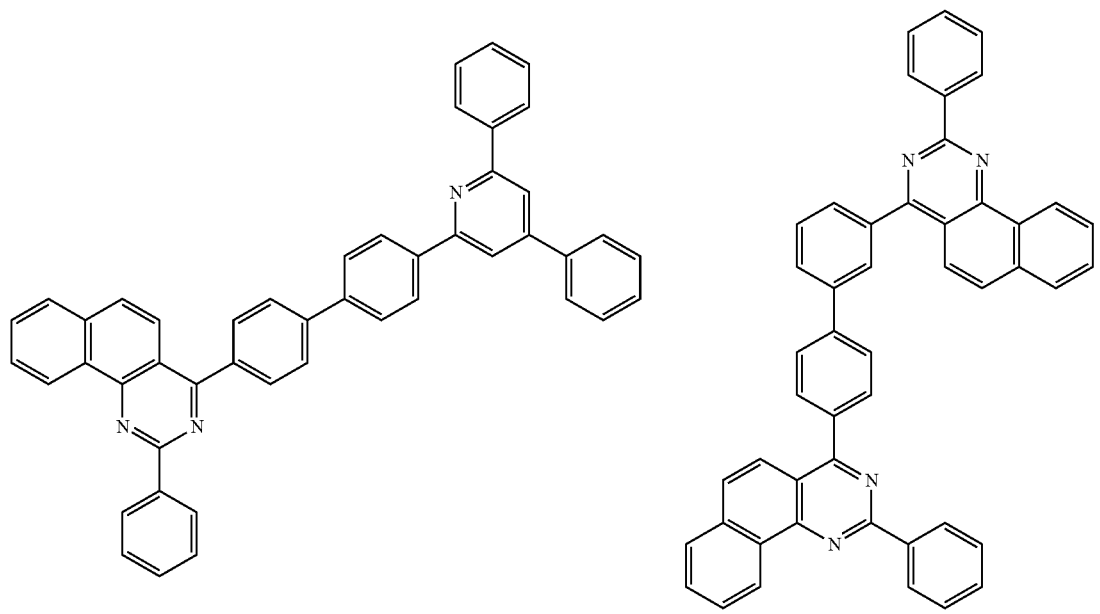
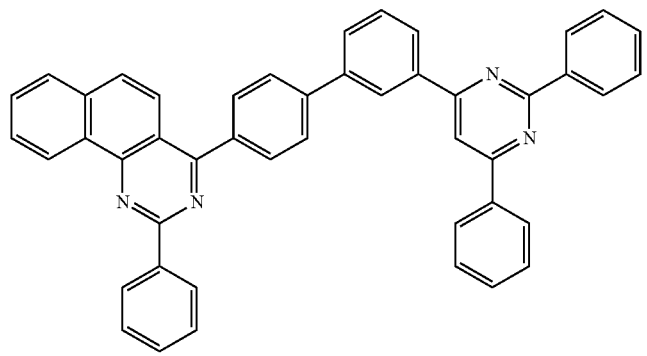

113
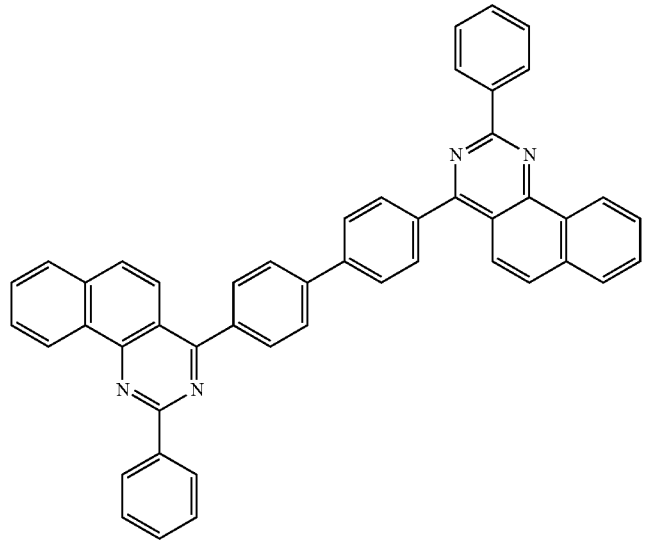
114
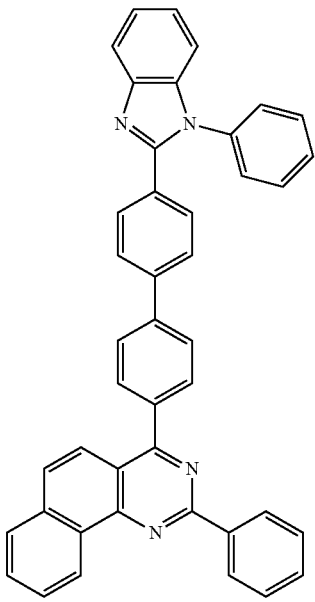
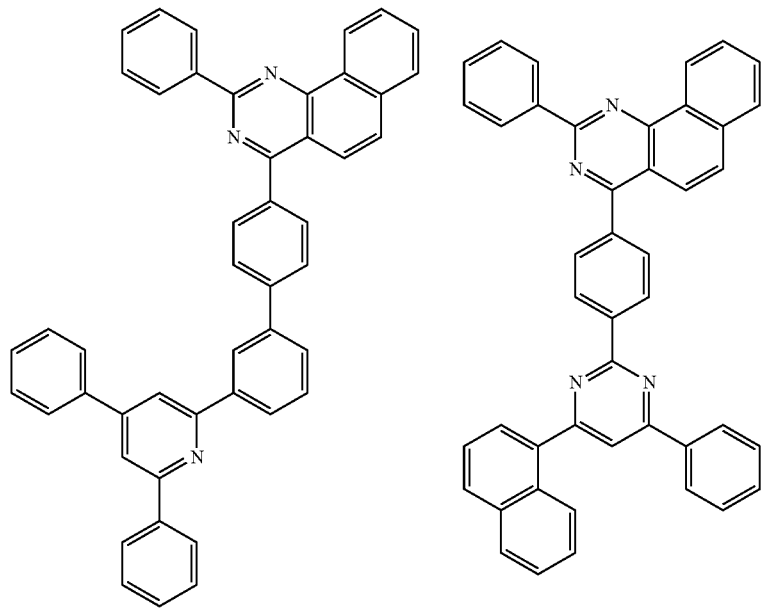
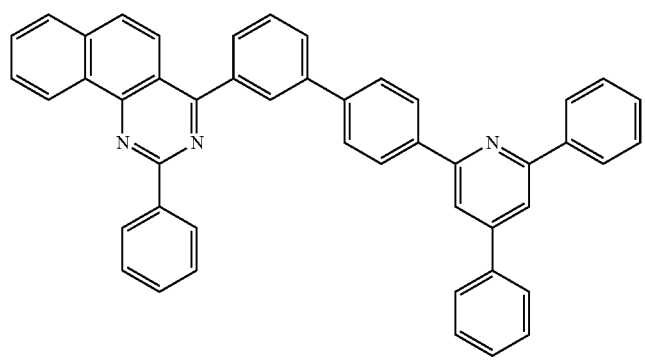

-continued
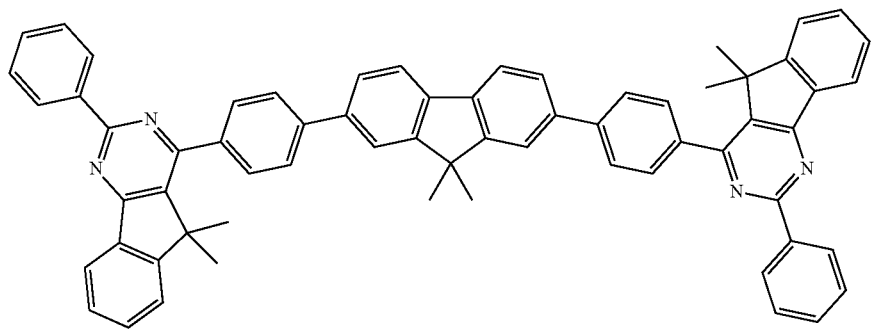
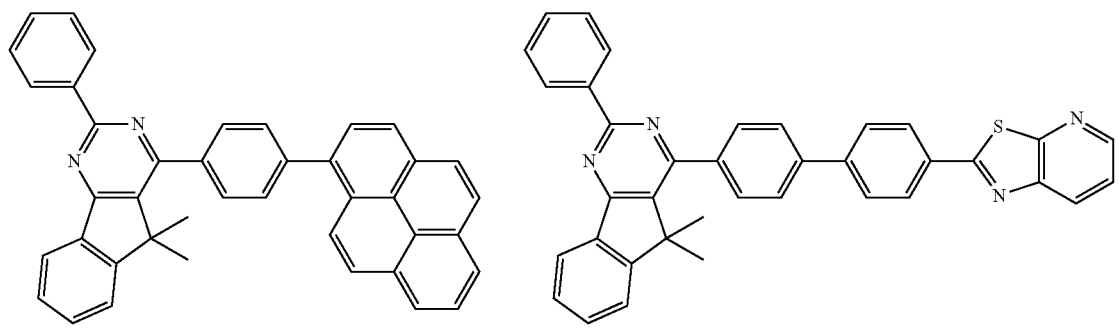
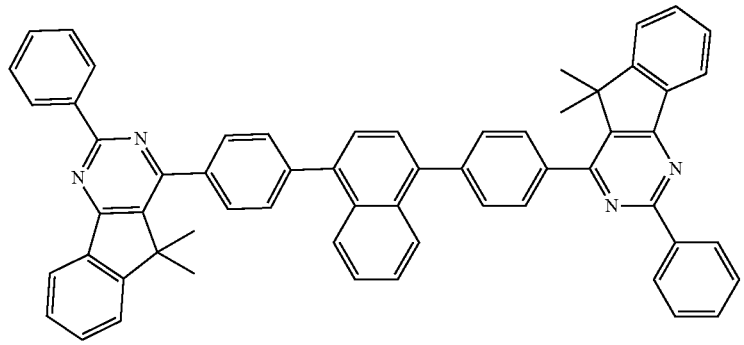
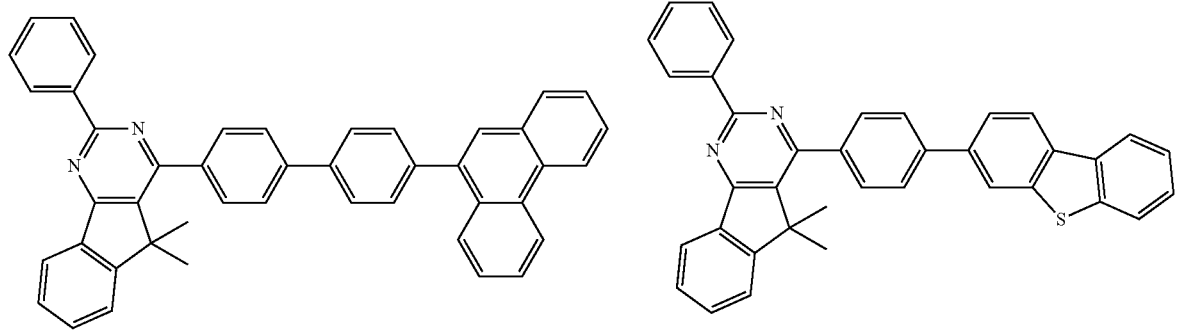
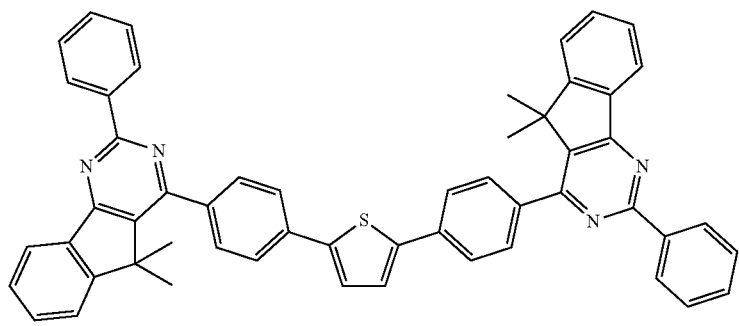

117 118
-continued
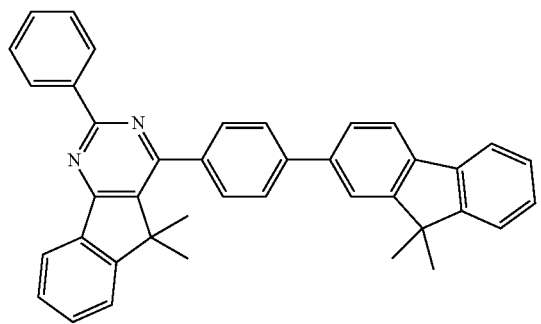
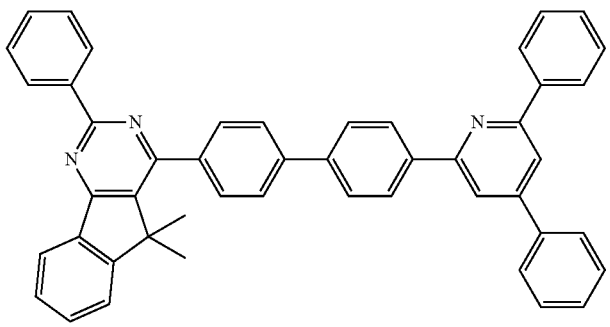
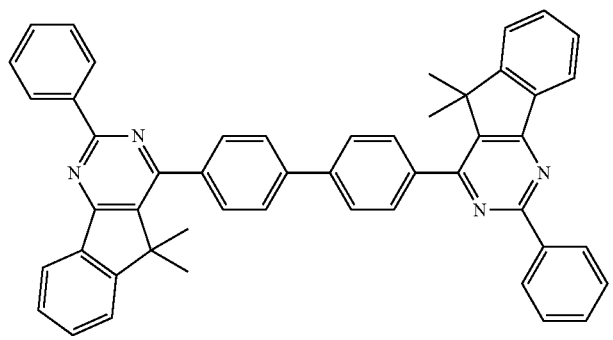
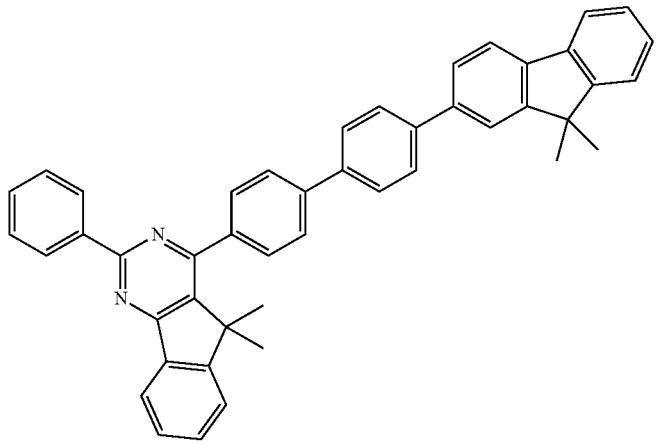
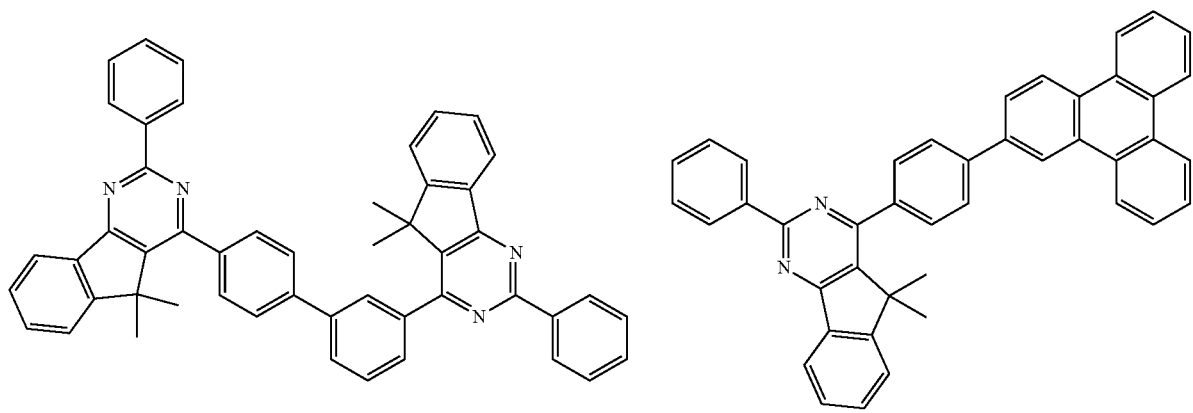

-continued
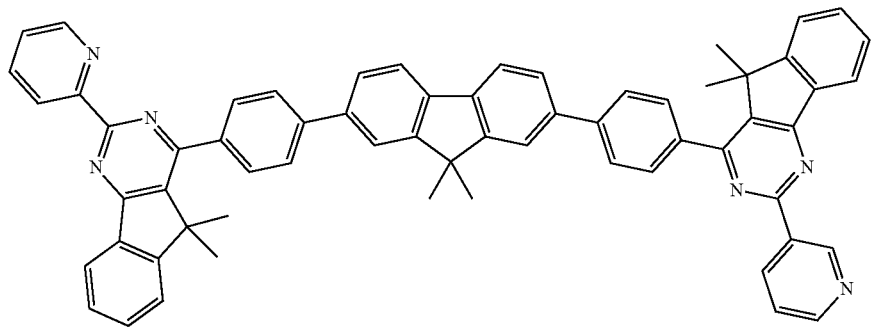
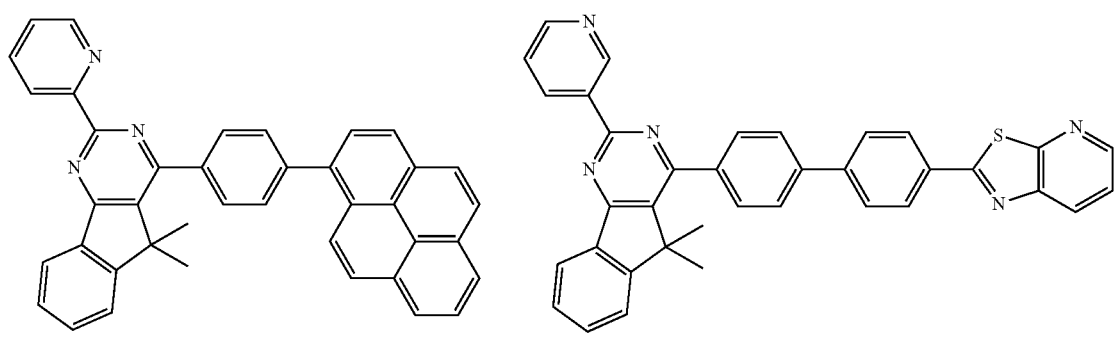
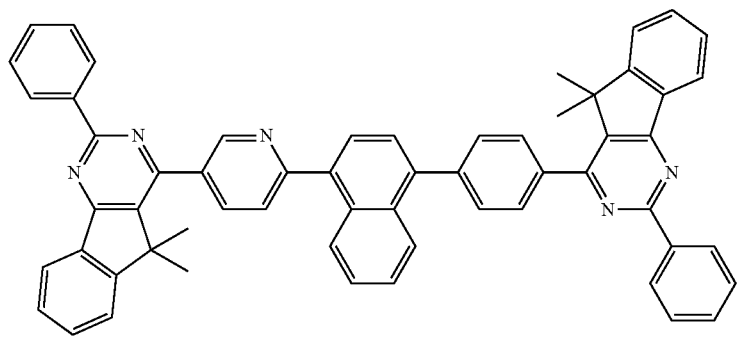
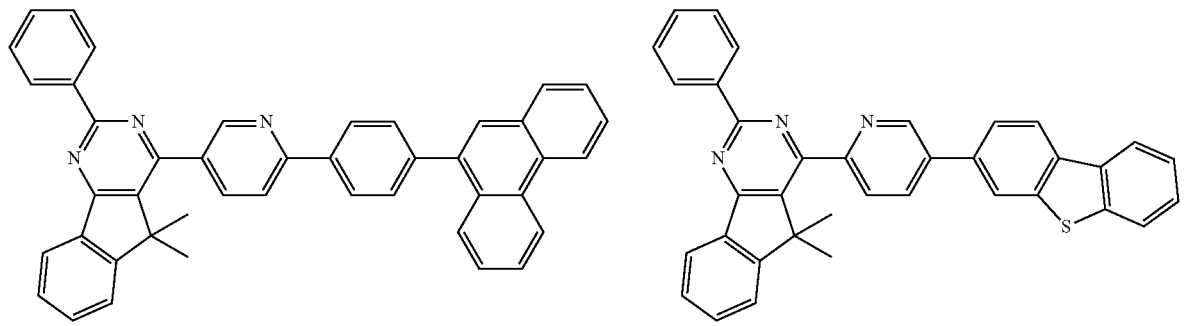
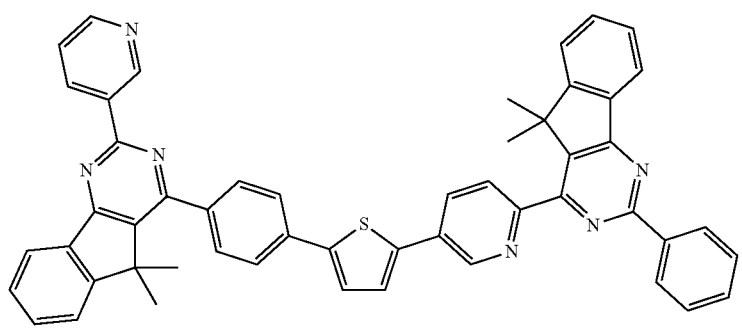

121
122
-continued
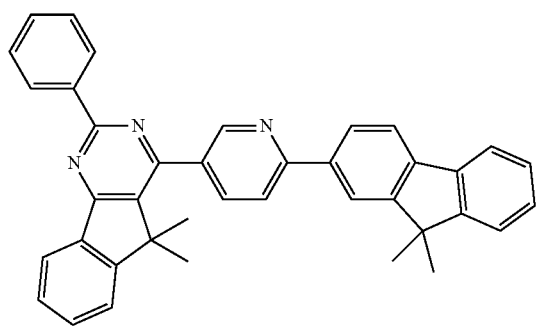
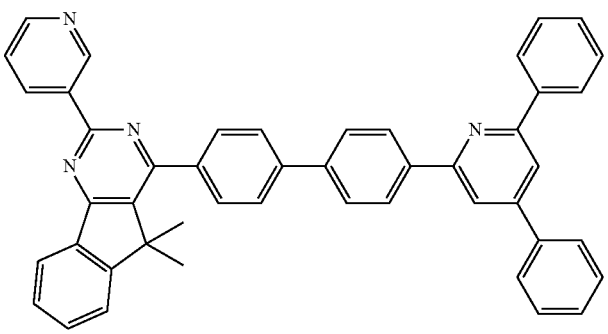
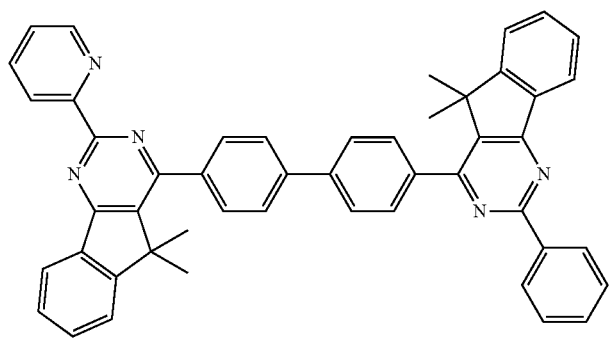
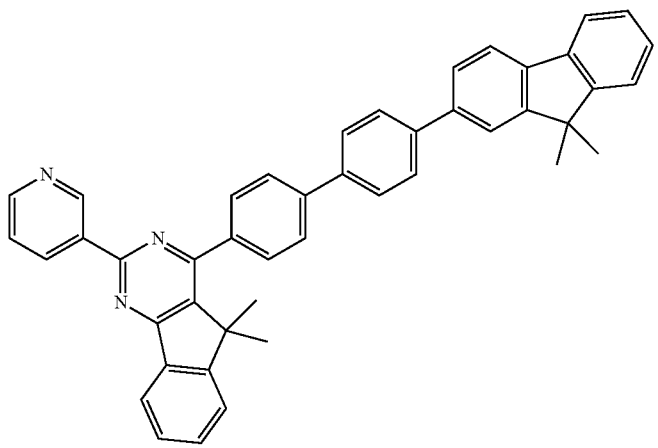
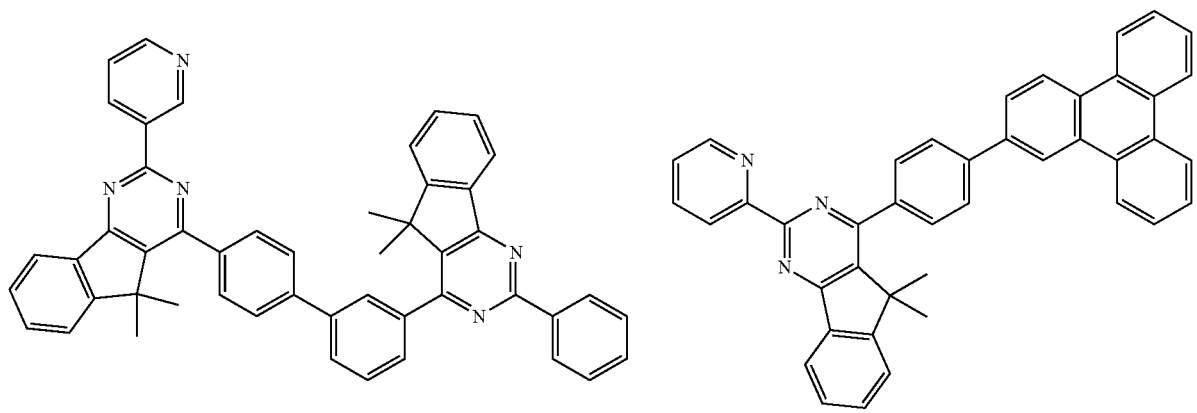 [SMILES: CC1(C)c2ccccc2-c2nc(-c3cccnc3)nc(-c3ccc(-c4cccc(-c5nc(-c6ccccc6)nc6c5C(C)(C)c5ccccc5-6)c4)cc3)c21 ; CC1(C)c2ccccc2-c2nc(-c3ccccn3)nc(-c3ccc(-c4ccc5c6ccccc6c6ccccc6c5c4)cc3)c21]

6. An organic electroluminescent device containing the electron transport material of claim 1.

7. The organic electroluminescent device of claim 6, wherein it includes:
- a first electrode; a second electrode; and at least one organic layer interposed between the first and second electrodes, the organic layer including an electron transport layer in which the electron transport material is contained.

* * * * *

UNITED STATES PATENT AND TRADEMARK OFFICE
CERTIFICATE OF CORRECTION

PATENT NO.         : 9,147,849 B2                               Page 1 of 1
APPLICATION NO.    : 13/772439
DATED              : September 29, 2015
INVENTOR(S)        : Hyun-Goog Nam et al.

It is certified that error appears in the above-identified patent and that said Letters Patent is hereby corrected as shown below:

Claims

Column 87, Line 47, Claim 1, delete "Art(s)" and insert -- $Ar_1(s)$ --

Signed and Sealed this
Twenty-second Day of March, 2016

Michelle K. Lee
*Director of the United States Patent and Trademark Office*